United States Patent
Kim et al.

(10) Patent No.: US 9,573,907 B2
(45) Date of Patent: Feb. 21, 2017

(54) 2, 4-PYRIMIDINE DERIVATIVES AND USE THEREOF

(75) Inventors: Sunghoon Kim, Seoul (KR); Jung Min Han, Seoul (KR); Hyeong Rae Kim, Daejeon (KR); Dong Ju Jeon, Daejeon (KR); Jong Hwan Song, Chungcheongbuk-do (KR); Kyung Eun Park, Daejeon (KR)

(73) Assignees: SNU R&DB FOUNDATION, Seoul (KR); KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 476 days.

(21) Appl. No.: 13/505,651

(22) PCT Filed: Nov. 2, 2010

(86) PCT No.: PCT/KR2010/007656
§ 371 (c)(1),
(2), (4) Date: Jul. 23, 2012

(87) PCT Pub. No.: WO2011/053090
PCT Pub. Date: May 5, 2011

(65) Prior Publication Data
US 2012/0322802 A1 Dec. 20, 2012

(30) Foreign Application Priority Data
Nov. 2, 2009 (KR) .................. 10-2009-0105153

(51) Int. Cl.
*A61K 31/506* (2006.01)
*A61K 31/5377* (2006.01)
*C07D 409/12* (2006.01)
*C07D 239/60* (2006.01)
*C07D 413/12* (2006.01)
*C07D 239/52* (2006.01)
*C07D 401/12* (2006.01)

(52) U.S. Cl.
CPC ........... *C07D 239/60* (2013.01); *C07D 239/52* (2013.01); *C07D 401/12* (2013.01)

(58) Field of Classification Search
CPC ... C07D 409/12; C07D 239/60; C07D 413/12; A61K 31/506; A61K 31/5377
USPC ..... 514/235.8, 274; 544/123, 300, 301, 302, 544/303; 506/9
See application file for complete search history.

(56) References Cited

FOREIGN PATENT DOCUMENTS

WO    WO 01/60816    8/2001

OTHER PUBLICATIONS

CDC, Centers for Disease Cntrol and Prevention, CDC 24/7.*
Bello, A., et al., (2008). "De novo design of nonpeptidic compounds targeting the interactions between interferon-α and its cognate cell surface receptor" *Journal of Medicinal Chemistry* 51(9):2734-2743.
Han, J., et al., (2007). "Aminoacyl-trna synthetase-interacting multifunctional protein 1/p43 controls endoplasmic reticulum retention of heat shock protein gp96 Its pathological implications in Ilupus-like autoimmune diseases" *The American Journal of Pathology: Molecular Pathogenesis of Gwnetic and Inherited Diseases.* 170(6):2042-2054.
Bello, A. M. et al., "De Novo Design of Nonpeptidic Compounds Targeting the Interactions between Interferon-a and its Cognate Cell Surface Receptor," Jrl. of Medicinal Chemistry, vol. 51, No. 9, pp. 2734-2743 (2008).
Han, J. M. et al., "Aminoacyl-tRNA Synthetase-Interacting Multifunctional Protein 1/p43 Controls Endoplasmic Reticulum Retention of Heat Shock Protein gp96; Its Pathological Implications in Lupus-Like Autoimmune Diseases," American Journal of Pathology, vol. 170, No. 6, pp. 2042-2054 (2007).

* cited by examiner

*Primary Examiner* — Alexander R Pagano
*Assistant Examiner* — Ebenezer O Sackey
(74) *Attorney, Agent, or Firm* — Harness, Dickey & Pierce, P.L.C.

(57) ABSTRACT

The present invention relates to novel 2,4-pyrimidine derivatives and a use thereof, and more particularly, to pyrimidine derivatives which are effective for systemic lupus erythematosus, a composition for preventing and treating systemic lupus erythematosus comprising the same as an active ingredient and a method for screening the same. The present inventors found novel materials inhibiting surface translocation of gp96 by mimicking a function of AIMP1 which is a molecular anchor for an intracellular residence of gp96, and identified in vitro and in vivo activity of the materials for preventing and treating SLE by alleviating SLE plasma in autoimmune diseases. Therefore, the present invention provides a novel method for screening a therapeutic agent for SLE, and preventing or treating SLE using the mechanism.

3 Claims, 35 Drawing Sheets

GPM1

NC1

2, 4-PYRIMIDINE DERIVATIVES AND USE THEREOF

CROSS REFERENCE TO RELATED APPLICATIONS

This application is a 371 national phase of International Application No. PCT/KR2010/007656 filed on Nov. 2, 2011, which claims the priority to Korean Application No. 10-2009-0105153 filed on Nov. 2, 2009, which applications are incorporated herein be reference.

TECHNICAL FIELD

This application claims priority rights based on Korean Patent Application No. 10-2009-0105153 filed on Nov. 2, 2009, the entire contents of which are incorporated herein by reference.

The present invention relates to novel 2,4-pyrimidine derivatives. More particularly, the present invention relates to 2,4-pyrimidine derivatives having an effect on an autoimmune disease such as systemic lupus erythematosus, a composition for preventing or treating a autoimmune disease (such as rheumatoid arthritis, systemic lupus erythematosus, and multiple sclerosis) comprising the same as an active ingredient, and a method of screening the same.

BACKGROUND ART

Systemic lupus erythematosus (SLE) is a kind of rheumatic disease, which is a cryptogenic autoimmune disease, shows a chronic progress through repetition of worsening and remission, accompanied by various symptoms in various organs such as skin and joints. In general, it occurs mainly in people between their twenties and forties, and more often in women than men. With respect to a population of 100,000, about 4~250 people are known to suffer from this disease.

Its exact cause is not proved, but is thought to be inherited, hormonal, caused by environment, certain viruses, extreme overwork, stress, certain drugs, or the like. Further, ultraviolet rays of sunlight are assumed to be one of the important causes. In a case of a genetic cause, even if both parents are patients suffering from the disease, not all of their children or siblings suffer from the disease, and the disease is not infectious to others.

There are highly various symptoms, which show different patterns and progress in patients. The patients show various symptoms such as macules on the skin, joint pain, chest pain, fever, or twinge of the whole body. In general, the first felt.symptoms may include general malaise and fatigue, body weight reduction or fever. In a case of rheumatoid arthritis, a symptom may occur in such a manner that a twinge in small joints of hands or feet gradually progresses into arthredema. Meanwhile, on a face, butterfly-shaped red spots may be found. They may also be found on other body parts, arms, or the back of the hand. Also, the disease may cause hair loss, or may cause the corresponding region to turn white or blue through sunlight exposure, accompanied by pain. It may cause pleurisy or pericarditis, resulting in chest ache during breathing. Also, it may cause inflammation in the kidneys, resulting in hematuria or proteinuria.

The disease is a chronic disease, and often requires continuous treatment. Thus, it may be accompanied by depressive disorder. In a case where the disease invades a central nervous system, a light symptom such as headache may be progressed into a serious symptom such as paralysis of arms and legs or a stroke causing corruption of consciousness. Further, an emotional disturbance or an attention disorder may occur. In many cases, anemia, thrombocytopenia, leucopenia or the like may occur. Especially, thrombocytopenia may cause cerebral hemorrhaging, and thus is required to be taken care of.

SLE causes various symptoms. Accordingly, according to symptoms of respective patients, suitable treatments have to be carried out in such a manner that symptoms can be minimized, inflammatory reactions can be reduced, and normal bodily functions can be maintained. In general, since long-time exposure to UV rays may worsen the disease, it is required to refrain from exposure to sunlight. In an unavoidable case, a UV blocking cream has to be applied. Further, since fatigue or overworking may worsen the disease, appropriate rest or relaxation is very important. The symptoms of SLE and other problems, such as mental stress, occurring during a treatment process may be relieved by talking about the symptoms and problems with friends and family.

At present, for treatment of SLE, a steroid-based therapeutic agent such as corticosteroids (cortisone) or prednisone, NSAIDS (Non Steroidal Anti-Inflammatory Drugs) such as aspirin, ibuprofen (Motrin, Advil), naproxen (Naprosyn), sulindac (Clinoril), diclofenac (Voltaren), piroxicam (Feldene), ketoprofen (Orudis), diflunisal (Dolobid), nabumetone (Relafen), etodolac (Lodine), oxaprozin (Daypro) or indomethacin (Indocin), an antimalarial agent such as hydroxychloroquine (Plaquenil) or chloroquine (Aralen), and an immunosupressive agent such as Azathiprine (Imuran) or cyclophosphamide (cytoxan) are administered alone or in combination. However, the steroid-based agent may not only cause weight gain, hypersensitivity reaction, excitement, euphoria, depressive disorder or insomnia but also cause predisone in diabetes mellitus, glaucoma or hypertension. Moreover, when used for a long term, it may cause side effects such as cataracts, muscle weakening, bone angionecrosis or osteoporosis. Also, NSAIDS may cause side effects such as gastrointestinal disorder, dyspepsia, enterohemorrhage, headaches, sleepiness, hypertension or renal failure, the antimalarial agent may cause side effects such as rash, pigmentation, alopecia, xeroderma, gastrointestinal injury, anorexia, abdominal distension, vomiting, convulsion, nausea or diarrhea, and the immunosuppressive drug may cause side effects such as anemia, leucopenia or infection possibility increase. Hence, it is urgently required to develop a novel therapeutic agent.

DISCLOSURE

Technical Problem

The present inventors have made intensive researches to develop novel materials effective in prevention or treatment of SLE. As a result, the present inventors found materials that inhibit surface translocation of gp96 by mimicking a function of AIMP1 that is a molecular anchor for an intracellular residence of gp96, and then identified that the materials in vitro and in vivo relieve an SLE character, and that gp69 is a potential target for regulating SLE. Then, based on this finding, the present inventors completed this invention.

Accordingly, it is an object of the present invention to provide novel 2,4-pyrimidine derivatives and its use.

Technical Solution

In accordance with an aspect of the present invention, there is provided a compound represented by Formula 1 or its pharmaceutically acceptable salt.

In accordance with another aspect of the present invention, there is provided a pharmaceutical composition for preventing or treating SLE comprising the inventive compound or its pharmaceutically acceptable salt.

In accordance with a further aspect of the present invention, there is provided a use of the inventive compound or its pharmaceutically acceptable salt in preparation of a systemic lupus erythematosus preventive or therapeutic agent.

In accordance with a still further aspect of the present invention, there is provided a method for preventing or treating systemic lupus erythematosus in a subject comprising administering to a subject in need thereof an effective dose of the compound or its pharmaceutically acceptable salt.

In accordance with a still yet further aspect of the present invention, there is provided a method of screening a therapeutic agent for systemic lupus erythematosus, comprising:

(a) contacting a testing agent with AIMP1-conjugated gp96 in the presence of the testing agent;

(b) selecting a testing agent changing AIMP1 and gp96 binding ability by measuring dissociation activity of AIMP1 and gp96; and (c) testing if the selected agent treats or relieves a symptom of systemic lupus erythematosus.

Hereinafter, the present invention will be described in detail.

The present inventors found materials that inhibit surface translocation of gp96 by mimicking a function of AIMP1 that is a molecular anchor for an intracellular residence of gp96, and then determined if the materials in vitro and in vivo relieve an SLE character. As a result, present inventors found that the inventive pyrimidine compound or its salt has an effect on preventing or treating a symptom of SLE, and gp69 may be a potential target for treating or relieving SLE.

Accordingly, the present invention provides, as a compound capable of being used for prevention or treatment of SLE, a pyrimidine compound represented by Formula 1 or its pharmaceutically acceptable salt.

[Formula 1]

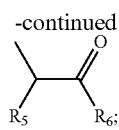

In Formula above, $R_1$ represents hydrogen, straight or branched saturated or unsaturated $(C_1-C_{10})$ alkyl, straight or branched saturated or unsaturated $(C_1-C_{10})$ alkyl substituted with halogen,

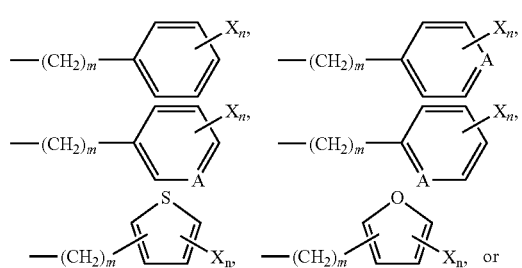

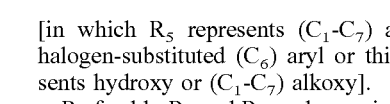

[A represents N or NO; m and n each independently represents an integer of 0 to 2; X may be the same or different, and each independently represents straight or branched saturated or unsaturated $(C_1-C_7)$ alkyl, straight or branched saturated or unsaturated $(C_1-C_7)$ alkyl substituted with halogen, $(C_1-C_7)$ alkoxy, $(C_1-C_7)$ alkylthio, $(C_1-C_7)$ alkoxycarbonyl, halogen, cyano, nitro, amino, aminocarbonyl, benzyloxy or carboxylic acid.]

$R_5$ represents hydrogen, straight or branched saturated or unsaturated $(C_1-C_{10})$ alkyl, straight or branched saturated or unsaturated $(C_1-C_{10})$ alkyl substituted with halogen,

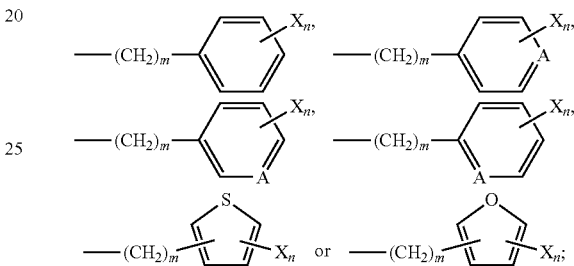

$R_6$ represents hydroxy, $(C_1-C_7)$ alkoxy, $(C_1-C_7)$ alkylthio, $(C_1-C_7)$ alkylamino substituted with single or multiple groups, morpholine, piperazine, piperidine, or $(C_1-C_4)$ hydroxyamide substituted with single or multiple groups;

$R_2$ and $R_3$ each independently represent hydrogen, $(C_1-C_7)$ alkyl, $(C_1-C_7)$ alkoxy, arylalkoxy or unsubstituted or halogen-substituted arylalkyl; and $R_4$ represents hydrogen, halogen, carboxyamide or pyridine.

Preferably, $R_1$ may represent hydrogen, unsubstituted or halogen-substituted $(C_7-C_{10})$ arylalkyl, unsubstituted or amine group-substituted pyridine, $(C_1-C_7)$ alkyl or

$R_5$ represents $(C_1-C_7)$ alkyl, unsubstituted or halogen-substituted $(C_6)$ aryl or thiophene, $R_6$ may represent hydroxy or $(C_1-C_7)$ alkoxy, and more preferably $R_1$ may represent hydrogen, benzyl, pyridine, aminopyridine, tert-butyl or

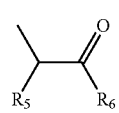

[in which $R_5$ represents $(C_1-C_7)$ alkyl, unsubstituted or halogen-substituted $(C_6)$ aryl or thiophene, and $R_6$ represents hydroxy or $(C_1-C_7)$ alkoxy].

Preferably $R_2$ and $R_3$ each may independently preferably represent hydrogen, $(C_1-C_7)$ alkyl, $(C_1-C_7)$ alkoxy or unsubstituted or halogen-substituted trihalomethylphenoxy, and more preferably represent hydrogen, methyl, methoxy, tert-butoxy, or fluoro-substituted trifluoromethylphenoxy.

Preferably, $R_4$ may represent hydrogen, chloro, carboxyamide or pyridine.

$R_1$, $R_2$, $R_3$, $R_4$, $R_5$, and $R_6$ each may denote one compound or structurally allowable plural compounds.

"alkyl" indicates a straight-chain or branched aliphatic hydrocarbon group having about 1 to 20 carbon atoms in the chain. Preferably, an alkyl group includes about 1 to 12 carbon atoms in the chain. More preferably, an alkyl group includes about 1, 2, 3, 4, 5 or 6 carbon atoms in the chain. A branched group indicates that at least one lower alkyl group, for example, methyl, ethyl or propyl is attached to a linear alkyl chain. The term "lower alkyl" indicates a straight-chain or branched group having about 1 to 6 carbon atoms. "alkyl" may be unsubstituted or optionally substituted with at least one same or different substituent, in which each substituent may be halogen, alkyl, aryl, cycloalkyl, cyano, hydroxy, alkoxy, alkylthio, amino, carboxy or the like. Preferably, alkyl may be butyl or isobutyl.

"Alkoxy" indicates an alkyl-O-group in which the alkyl group is as previously described. Appropriate examples of the alkoxy group include methoxy, ethoxy, n-propoxy, isopropoxy and n-butoxy. Alkoxy is bonded to a parental residue through oxygen. Preferably, alkoxy may be methoxy.

"aryl" means an aromatic hydrocarbon ring system, and its examples include phenyl, indenyl, indanyl, naphthyl, fluorenyl and the like. Preferably, it may be (6C) aryl.

"halogen" may include a fluorine atom, a chlorine atom, a bromine atom, or an iodine atom, and preferably may be a fluorine atom, a chlorine atom, or a bromine atom.

"alkyl substituted with halogen" means an alkyl group substituted with 1 to halogen atom(s), for example, may be fluoromethyl, chloromethyl, difluoromethyl, dichloromethyl, dibromomethyl, trifluoromethyl, trichloromethyl, fluoroethyl, chloroethyl, trifluoroethyl, trichloroethyl, fluoropropyl, fluorobutyl, fluorohexyl or the like. Preferably, it may be (C1-C6) alkyl substituted with halogen, and more preferably it may be (C1-C6) alkyl substituted with chlorine or fluorine.

"aryl substituted with halogen" means an aryl group substituted with 1 to 3 halogen atom(s), for example, may be fluorophenyl, difluorophenyl, trifluorophenyl, chlorophenyl, dichlorophenyl, trichlorophenyl, bromophenyl, dibromophenyl, tribromophenyl, difluorobenzyl, dichlorobenzyl, dibromobenzyl or the like. Preferably, it may be chlorophenyl.

"aryl substituted with alkyl" or "arylalkyl" means an aryl group substituted with 1 to 3 alkyl substituents, for example, may be benzyl, ethylphenyl, propylphenyl, dimethyl phenyl, diethylphenyl, trimethylphenyl, triethylphenyl or the like. Preferably it may be benzyl.

Pyridine means an aromatic heterocyclic organic compound with a 6-atom cyclic structure of 5 carbon atoms and 1 nitrogen atom.

Meanwhile, the inventive compound may be preferably (S)-methyl 2-(4,6-dimethoxypyrimidin-2-yloxy)-3-methylbutanoate of Formula 2 below, methyl 2-(5-chloro-4-methoxy-6-methylpyrimidin-2-yloxy)propanoate of Formula 3 below, methyl 2-(4-bromophenyl)-2-(4,6-dimethoxypyrimidin-2-yloxy)acetate of Formula 4 below, methyl 2-(4,6-dimethoxypyrimidin-2-yloxy)-3-methylbutanoate of Formula 5 below, methyl 2-(4,6-dimethoxypyrimidin-2-yloxy)-2-(thiophen-2-yl)acetate of Formula 6 below, 2-(4,6-dimethoxypyrimidin-2-yloxy)-2-phenylacetic acid of Formula 7 below, (R)-2-(4,6-dimethoxypyrimidin-2-yloxy)-2-phenylacetic acid of Formula 8 below, 2-(benzyloxy)-4,6-dimethoxypyrimidine-5-carboxamide of Formula 9 below, 2-(2-chlorobenzyloxy)-4,6-dimethoxypyrimidine of Formula 10 below, 4,6-dimethoxy-2-(pyridin-4-yloxy)pyrimidine of Formula 11 below, 4,6-di-tert-butoxy-2-(pyridin-3-yloxy)pyrimidine of Formula 12 below, 2,4-di-tert-butoxy-5-(pyridin-2-yl)pyrimidine of Formula 13 below, 4,6-bis(4-fluoro-3-(trifluoromethyl)phenoxy)pyrimidin-2-ol of Formula 14 below, 3-(4,6-dimethoxypyrimidin-2-yloxy)pyridin-2-amine of Formula 15 below, 2-(4,6-Dimethoxy-pyrimidin-2-yloxy)-N,N-diethyl-3-methyl-butyl amide of Formula 17 below, N-Butyl-2-(4,6-dimethoxy-pyrimidin-2-yloxy)-3-methyl-butyl amide of Formula 18, 2-(4,6-Dimethoxy-pyrimidin-2-yloxy)-3-methyl-N-phenyl-butyl amide of Formula 19, N-Benzyl-2-(4,6-dimethoxy-pyrimidin-2-yloxy)-3-methyl-butyl amide of Formula 20, 2-(4,6-dimethoxy-pyrimidin-2-yloxy)-N-isopropyl-3-methyl-butyl amide of Formula 21, 2-(4,6-dimethoxy-pyrimidin-2-yloxy)-N-methoxy-3,N-dimethyl-butyl amide of Formula 22, 2-(4,6-dimethoxy-pyrimidin-2-yloxy)-3-methyl-1-piperidin-1-yl-butan-1-one of Formula 23, 2-(4,6-dimethoxy-pyrimidin-2-yloxy)-3-methyl-1-morpholin-4-yl-butan-1-one of Formula 24, 2-(4,6-dimethoxy-pyrimidin-2-yloxy)-3-methyl-butyric acid of Formula 25, 2-(4,6-Dimethoxy-pyrimidin-2-yloxy)-3-methyl-butyric acid methyl ester of Formula 26, L-2-(4,6-Dimethoxy-pyrimidin-2-yloxy)-propionic acid methyl ester of Formula 27, D-2-(4,6-Dimethoxy-pyrimidin-2-yloxy)-propionic acid methyl ester of Formula 28, 2-(4,6-Dimethoxy-pyrimidin-2-yloxy)-2-methyl-propionic acid methyl ester of Formula 29, D-3-(4,6-Dimethoxy-pyrimidin-2-yloxy)-butyric acid methyl ester of Formula 30, L-2-(4,6-Dimethoxy-pyrimidin-2-yloxy)-3-methyl-butyric acid methyl ester of Formula 31, (4,6-Dimethoxy-pyrimidin-2-yloxy)-phenyl-acetic acid methyl ester of Formula 32, (4,6-Dimethoxy-pyrimidin-2-yloxy)-phenyl-acetic acid of Formula 33, 2-(4,6-Dimethoxy-pyrimidin-2-yloxy)-N-isopropyl-2-phenyl-acetamide of Formula 34, N-Benzyl-2-(4,6-dimethoxy-pyrimidin-2-yloxy)-2-phenyl-acetamide of Formula 35, N-Butyl-2-(4,6-dimethoxy-pyrimidin-2-yloxy)-2-phenyl-acetamide of Formula 36, 2-(4,6-Dimethoxy-pyrimidin-2-yloxy)-N,N-diethyl-2-phenyl-acetamide of Formula 37, L-2-(4,6-Dimethoxy-pyrimidin-2-yloxy)-3-methyl-butyric acid of Formula 38, D-2-(4,6-Dimethoxy-pyrimidin-2-yloxy)-propionic acid of Formula 39, or L-2-(4,6-Dimethoxy-pyrimidin-2-yloxy)-propionic acid of Formula 40.

Herein, in Formulas below, "Me" represents a methyl group.

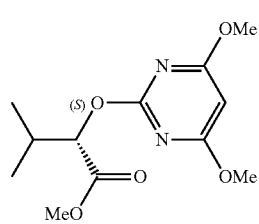

[Formula 2]

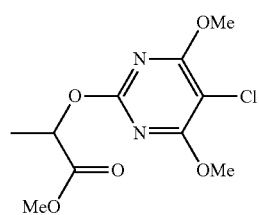

[Formula 3]

[Formula 4]
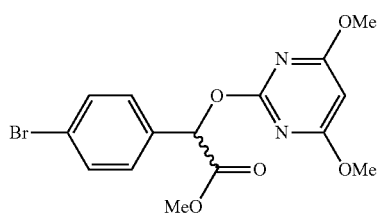
[Formula 5]
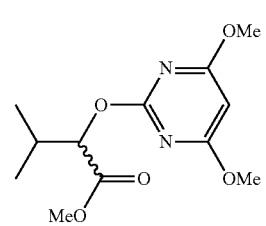
[Formula 6]
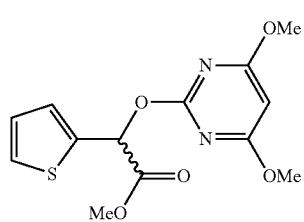
[Formula 7]
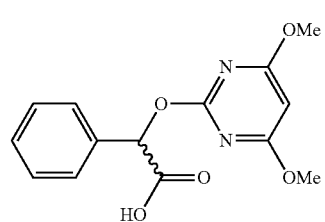
[Formula 8]
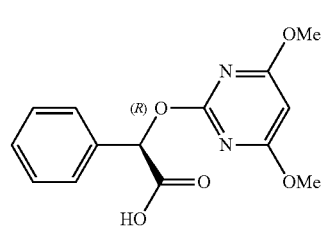
[Formula 9]
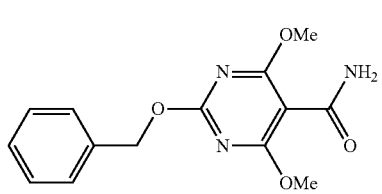
[Formula 10]
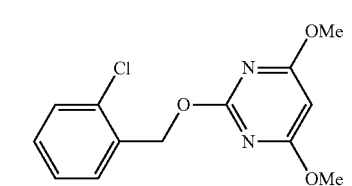
[Formula 11]
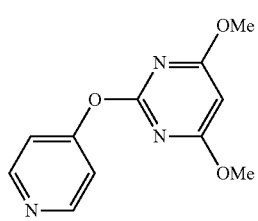
[Formula 12]
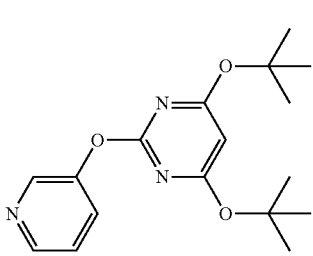
[Formula 13]
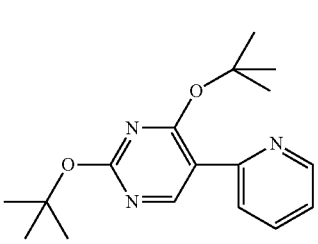
[Formula 14]
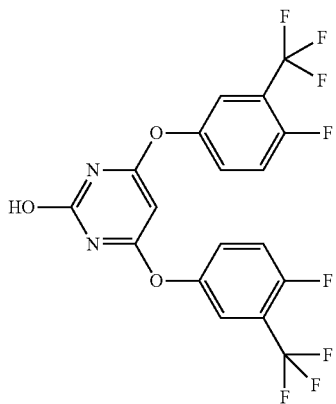
[Formula 15]
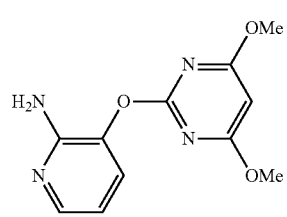
[Formula 17]
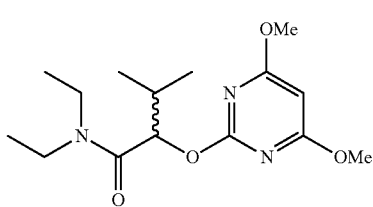

[Formula 18]
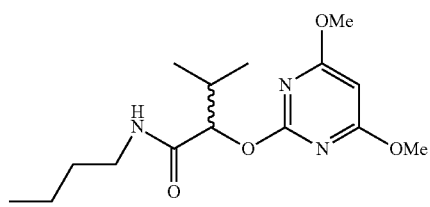
[Formula 19]
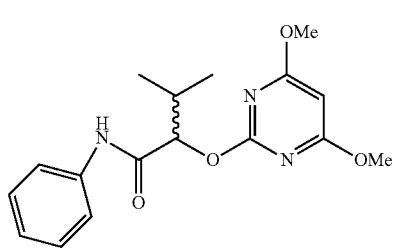
[Formula 20]
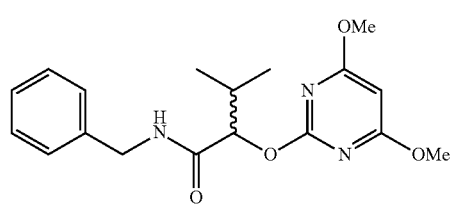
[Formula 21]
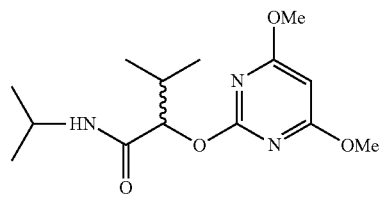
[Formula 22]
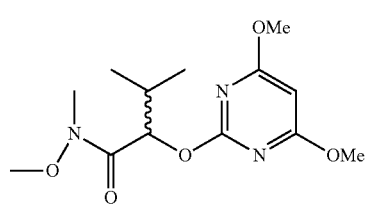
[Formula 23]
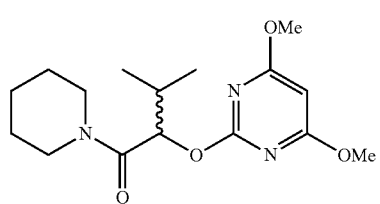
[Formula 24]
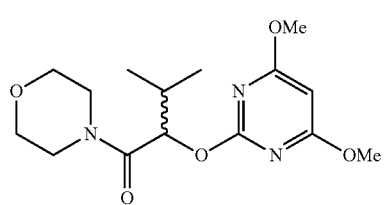
[Formula 25]
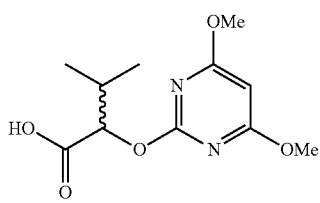
[Formula 26]
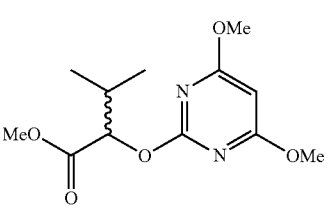
[Formula 27]
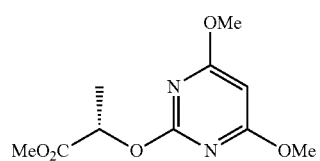
[Formula 28]
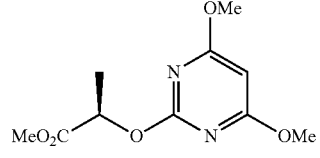
[Formula 29]
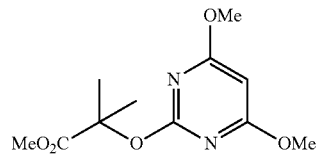
[Formula 30]
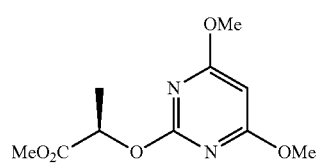
[Formula 31]
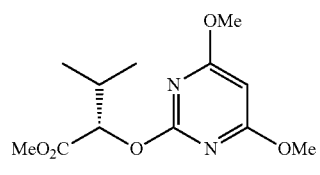
[Formula 32]
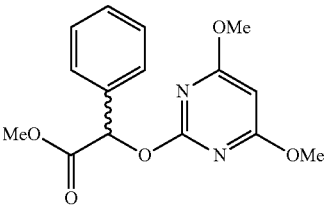

[Formula 33]

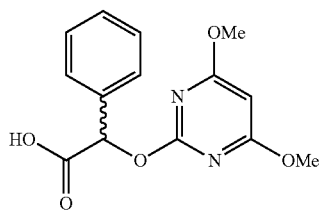

[Formula 34]

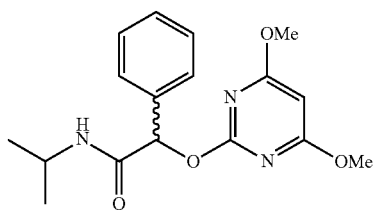

[Formula 35]

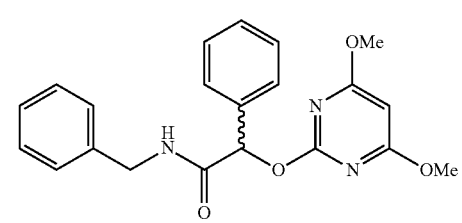

[Formula 36]

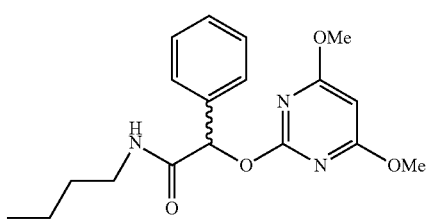

[Formula 37]

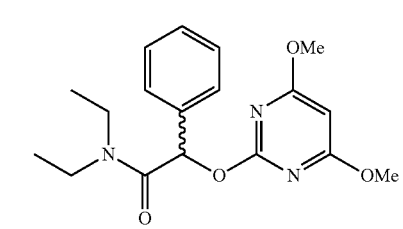

[Formula 38]

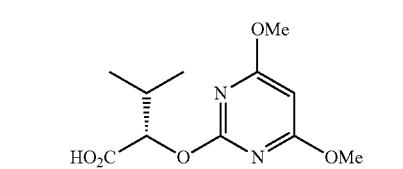

[Formula 39]

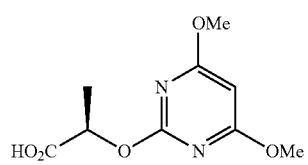

[Formula 40]

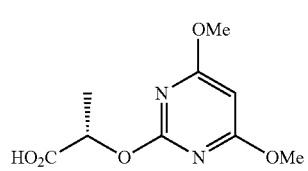

The preparation method according to the present invention is exemplified in Reaction Scheme 1, but the preparation method below is not intended to limit the inventive method of preparing a compound of Formula 1. It is natural to a person skilled in the art that the preparation method below can be changed. If not mentioned otherwise, the definition of the substitute in Reaction Scheme below is the same as that in Formula 1.

As represented by Reaction Scheme 1, the inventive 2,4-pyrimidine compound represented by Formula 1 may be prepared by reacting alcohol (compound 1) with 2,4-pyrimidine (compound 2) in a DMF medium through a base such as $K_2CO_3$, and also may be synthesized by other methods. Herein, X of compound 2 mainly represents alkyl sulfonyl (such as methanesulfonyl) alkyl sulfoxide, or halogen (such as chlorine, fluorine), and $R_1$, $R_2$, $R_3$ and $R_4$ are the same as defined in Formula 1.

[Reaction Scheme 1]

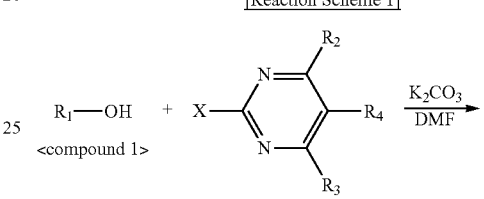

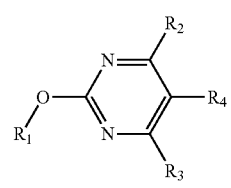

<Formula 1>

The inventive compound or its pharmaceutically acceptable salt inhibits surface translocation of gp96 by mimicking a function of AIMP1 within cells, and in vitro and in vivo shows an effect in preventing, relieving, or treating an SLE character or symptom. Accordingly, the inventive compound or its pharmaceutically acceptable salt has a preventive and therapeutic effect on SLE.

In the present invention, "gp96", "gp96 protein" or "gp96 polypeptide" is a kind of heat shock protein. The gp96 protein may be a gp96 protein known in the art, and preferably, a polypeptide having amino acid sequences represented by Genbank Accession Nos. NM_003299, AK025459, AJ890084, X15187, NM_003299.1, and M33716.1.

gp96 is a protein existing on ER-HSP90, and has a function of a chaperone by recycling between ER and Golgi (Li, Z., Dai, J., Zheng, H., Liu, B. & Caudill, M. Front. Biosci. 7, d731-751 (2002)). gp96 is known to be related to innate, adaptive imunity (Srivastava, P. K., Menoret, A., Basu, S., Binder, R. J. & McQuade, K. L. Immunity 8, 657-665 (1998)). When exposed on a cell surface, gp96 induces an immunoactivity action such as dendritic cell (DC) maturation (Hilf, N., Singh-Jasuja, H., Schwarzmaier, P., Gouttefangeas, C., Rammensee, H. G. & Schild, H. Blood 99, 3676-3682 (2002)). gp96 induces DC maturation by receptors CD91 and TLR2/4 and allows inflammatory cytokine TNF alpha to be secreted (Binder, R. J., Han, D. K. & Srivastava, P. K. Nat. Immunol. 1, 151-155 (2000)., Vabulas, R. M., Braedel, S., Hilf, N., Singh-Jasuja, H., Herter, S., Ahmad-Nejad, P., Kirschning, C. J., Da Costa, C., Rammensee, H. G., Wagner, H. & Schild, H. J. Biol. Chem. 277, 20847-20853 (2002)). It has been recently known that a gp96 transgenic mouse shows an autoimmune symptom such as lupus (Liu, B., Dai, J., Zheng, H., Stoilova, D., Sun, S. & Li, Z. Proc. Natl. Acad. Sci. USA 100, 15824-15829 (2003)) and a significant increase of expression at a rheumatoid arthritis site (Huang, Q. Q., Sobkoviak, R., Jockheck-Clark, A. R., Shi, B., Mandelin, A. M. 2nd, Tak, P. P., Haines, G. K. 3rd, Nicchitta, C. V. & Pope, R. M. J. Immunol. 182, 4965-4973 (2009)).

In the present invention, "AIMP1 (ARS-interacting multi-functional protein 1)", "AIMP1 protein" or "AIMP1 polypeptide", formerly known as p43 protein, was renamed by the inventors (Sang Gyu Park, et al., Trends in Biochemical Sciences, 30:569-574, 2005). The AIMP1 is a protein having 312 amino acids, which is bound to a mult-tRNA synthetase complex (Deutscher, M. P., Method Enzymol, 29, 577-583, 1974; Dang C. V. et al., Int. J. Biochem. 14, 539-543, 1982; Mirande, M. et al., EMBO J. 1, 733-736, 1982; Yang D. C. et al., Curr. Top Cell. Regul. 26, 325-335, 1985), thereby improving catalytic activity of the multi-tRNA synthetase (Park S. G. et al., J. Biol. Chem. 274, 16673-16676, 1999). AIMP1 is secreted from various types of cells, including prostate cancer cells, immune cells and transgenic cells, and the secretion is induced by various stimulations such as TNFα and heat shock (Park S. G. et al., Am. J. Pathol., 166, 387-398, 2005; Barnett G. et al., Cancer Res. 60, 2850-2857, 2000). The secreted AIMP1 is known to work on diverse target cells such as monocytes/macrophages, endothelial cells and fibroblast cells.

The inventive compound or its pharmaceutically acceptable salt can prevent, relieve, or treat in vitro and in vivo an SLE character or symptom, and thus can be applied to prevention and treatment of SLE. Accordingly, the present invention provides a pharmaceutical composition for prevention and treatment of SLE, which includes the inventive compound or its pharmaceutically acceptable salt as an active ingredient. The inventive composition may have a composition including 0.001 to 99.999 wt % of the inventive compound or its pharmaceutically acceptable salt, and balance carrier. The carrier may be a pharmaceutically acceptable carrier.

The inventive pharmaceutical composition may include the inventive compound or its pharmaceutically acceptable salt alone in a pharmaceutically effective dose or further include at least one pharmaceutically acceptable carrier. The "pharmaceutically effective dose" indicates the amount needed to achieve a better result than that in a negative control group, and preferably indicates the amount enough to treat or prevent systemic lupus erythematosus. According to the present invention, a pharmaceutically effective dose of the inventive compound ranges from 0.00001 to 100 mg/day/kg body weight. However, the pharmaceutically effective dose may appropriately vary according to many factors such as a disease or its severity, age, body weight, health condition, sex, administration route, administration period, etc.

Meanwhile, the present invention provides a use of the compound represented by Formula 1 or its pharmaceutically acceptable salt in the preparation of a preventive and therapeutic agent for systemic lupus erythematosus.

Also, the present invention provides a method for preventing and treating systemic lupus erythematosus comprising administering to a subject in need thereof an effective dose of the compound represented by Formula 1 or its pharmaceutically acceptable salt. The compound represented by Formula 1 may be any one selected from the group consisting of compounds represented by Formulas 2 to 15 and Formulas 17 to 40.

The inventive compound may be used as it is or as a salt, preferably a pharmaceutically acceptable salt. The term 'pharmaceutically acceptable' indicates that it is physiologically acceptable and its administration to humans does not generally cause an allergic reaction or its similar reaction. As the salt, an acid-added salt formed by a pharmaceutically acceptable free acid is preferred. As the free acid, an organic acid or an inorganic acid may be used. Examples of the organic acid include, but are not limited to, citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid and aspartic acid. Also, examples of the inorganic acid include, but are not limited thereto, hydrochloric acid, bromic acid, sulfuric acid and phosphoric acid.

The inventive compound or its pharmaceutically acceptable salt may be administered in an effective dose through various routes, such as oral, intracutaneous, subcutaneous, intravenous and intramuscular routes. The term 'effective dose' indicates that the dose has the ability to cause a preventive and therapeutic effect of systemic lupus erythematosus when the compound is administered to patients. The term 'subject' means mammals, preferably animals including human beings, and may be cells, tissues, organs, etc. derived from animals. Also, the subject may be patients in need of treatment.

The inventive compound or its pharmaceutically acceptable salt may be administered as it is, or may be prepared into various formulations as described above for administration. Preferably, it may be administered until a required effect, that is, a systemic lupus erythematosus prevention/treatment effect, is obtained. The inventive compound or its pharmaceutically acceptable salt may be administered by various routes according to a method known in the art. In other words, it may be administered orally or parenterally, for example, buccally, intramuscularly, intravenously, intracutaneously, intraarterially, intraosseously, intrathecally, intraperitoneally, intranasally, intravaginally, rectally, sublingually or subcutaneously, or may be administered by a gastrointestinal, transmucosal or respiratory route. For example, the inventive compound or its pharmaceutically acceptable salt may be directly applied to skin. Otherwise, the polypeptide may be prepared into an injectable formulation, and then injected in a predetermined amount into a subcutaneous layer with a 30 gauge thin injection needle, or administered by lightly pricking the skin with the injection needle. Preferably, it may be directly applied to skin. Also, the inventive compound or its pharmaceutically acceptable salt may be administered into target cells or tissues (e.g., skin cells or skin tissues) by binding to a molecule causing high affinity-binding or being capsulated within the molecule. The inventive compound or its pharmaceutically acceptable salt may be bound to a sterol (e.g., cholesterol), a lipid (e.g., cationic lipid, virosome or liposome) or a target cell specific binding agent (e.g., ligand recognized by a target cell specific receptor) through the technology known in the art. As a coupling agent or a cross-linking agent, for example, protein A, carbodiimide, N-succinimidyl-3-(2-pyridyldithio)propiotate (SPDP) or the like may be appropriately included.

When the inventive compound or a composition including the compound is clinically administered, the inventive composition may be formulated into a unit dosage form of pharmaceutical formulation appropriate for oral or parenteral administration. When the composition is formulated into a general medicine form, a conventionally used diluent or excipient, such as a filler, an extender, a binder, a wetting agent, a disintegrating agent, a surfactant, etc. is used for the preparation. Examples of a solid preparation for oral administration may include tablets, pills, powders, granules, capsules and the like, and such a solid preparation is prepared by mixing the inventive compound with at least one excipient, for example, starch, calcium carbonate, sucrose, lactose, gelatin, or the like. Also, besides a simple excipient, lubricants such as magnesium stearate talc are used. Examples of a liquid preparation for oral administration may include a suspension, a liquid for internal use, an emulsion, a syrup, and the like, and the liquid preparation may include not only a generally used simple diluent, such as water, and liquid paraffin, but also various excipients, for example, a wetting agent, a sweetening agent, an aromatic agent, a preservative, etc. Examples of a preparation for parenteral administration include a sterilized aqueous solution, a nonaqueous solvent, a suspension, an emulsion, a freeze-drying agent, an ointment, and a cream. As a nonaqueous solvent, or a suspension solvent, propylene glycol, polyethylene glycol, vegetable oil (such as olive oil), injectable ester (such as ethyloleate), or the like may be used.

Also, the inventive compound or the composition including the compound may be parenterally administered, and the parenteral administration is carried out by subcutaneous injection, intravenous injection, intramuscular injection or intrasternal injection. For formulation into a form for parenteral administration, the inventive compound represented by Formulas 1 to 15 or Formulas 17 to 40 is prepared into a solution or a suspension liquid in mixture with a stabilizing agent or a buffer in water, and then is formulated into a unit dosage form of an ample or a vial. The dosage units can contain, for example, 1, 2, 3 or 4 times of an individual dose or ½, ⅓ or ¼ times of an individual dose. The individual dose preferably contains the amount of an effective drug which is administered in one dosage and which generally corresponds to a whole, a half, a third or a quarter of a daily dose. The dosage may vary according to the body weight; age, sex, health condition, diet, administration duration, administration method, excretion rate, medicine-mixtures and disease severity for a certain patient.

The formulations are described in Remington's Pharmaceutical Science (15th Edition, 1975. Mack Publishing Company, Easton, Pa. 18042, Chapter 87: Blaug, Seymour), which is generally known in pharmaceutical chemistry.

Meanwhile, the present invention provides a method of screening a therapeutic agent for systemic lupus erythematosus, comprising:

(a) contacting a testing agent with AIMP1-conjugated gp96 in the presence of the testing agent;

(b) selecting a testing agent changing AIMP1 and gp96 binding ability by measuring dissociation activity of AIMP1 and gp96; and (c) testing if the selected agent treats or relieves a symptom of systemic lupus erythematosus.

When the screening method is carried out, various biochemical and molecular biological techniques known in the art may be used. The techniques are disclosed in the following literatures: Sambrook et al., Molecular Cloning: A Laboratory Manual, Cold Spring Harbor Press, N.Y., Second (1998) and Third (2000) Editions; and Ausubel et al., Current Protocols in Molecular Biology, John Wiley & Sons, Inc., New York (1987-1999).

Preferably, first, in order to determine if the testing agent has an ability to modulate binding of AIMP1 and gp96, an assay is performed (a first assay step). Specifically, in the first step, in the presence of the testing agent, surface translocation of gp96 is assayed to identify a modulating agent for modulating binding of AIMP1 and gp96. More preferably, the first step may include the following steps:

(a) contacting a testing agent with AIMP1-conjugated gp96 in the presence of the testing agent; and (b) selecting a testing agent changing AIMP1 and gp96 binding ability by measuring dissociation activity of AIMP1 and gp96.

In the first assay step, modulation on the binding ability of AIMP1 and gp96 may be assayed. For example, it may be assayed if the testing agent has an activity to modulate binding of AIMP1 and gp96 or indirectly modulate surface translocation of gp96.

Then, after through the first assay step, an agent modulating AIMP1 and gp96 binding ability is identified, it is tested if the testing agent shows effects for treating or relieving (reducing) on systemic lupus erythematosus (second test step).

As mentioned above, the agent identified by the inventive method, for modulating AIMP1 and gp96 binding ability, can treat or relive a symptom of systemic lupus erythematosus. If the testing agent identified in the first assay step modulates surface movement of gp96, it can treat, reduce or relieve of a symptom of systemic lupus erythematosus.

In both the first and second steps, intact gp96 protein or AIMP1 protein, or a fragment, an analogue, or a functional equivalent thereof may be used. A fragment that can be used in this assay generally contains at least one biological activity of each of gp96 protein and AIMP1 protein. Also, fusion protein including the fragment or the analogue may be used for screening a testing agent. The functional equivalents of gp96 protein or AIMP1 protein have amino acid deletions and/or insertions and/or substitutions. However, each of them has the same bioactivity as that of gp96 protein or AIMP1 protein, and thus may be used for performing the inventive screening method.

Various assays conventionally performed in the art may be used to identify an agent for modulating binding ability of gp96 protein and AIMP1 protein or surface translocation of gp96. Preferably, the agent may be screened by a cell based assay system. For example, in a typical cell based assay for screening (that is, in the second testing step), reporter gene activity (e.g., enzymatic activity) in the presence of a testing agent is measured, and is compared to that in the absence of the testing agent. The reporter gene can encode any detectable polypeptide known in the art (response or reporter polypeptide), for example, detectable by fluorescence or phosphorescence or by its possessive enzymatic activity. The detectable response polypeptide may be, e.g., luciferase, alpha-glucuronidase, alpha-galactosidase, chloramphenicol acetyl transferase, green fluorescent protein, enhanced green fluorescent protein and the human secreted alkaline phosphatase.

In addition to the cell-based assay as described above, non-cell based methods may be used for screening. These methods include, e.g., mobility shift DNA-binding assays, methylation and uracil interference assays, DNase and hydroxyl radical footprinting analysis, fluorescence polarization, and UV crosslinking or chemical cross-linkers. For a general overview, see Ausubel et al (Ausubel et al., supra, chapter 12, DNA-Protein Interaction). One technique for isolating co-associating proteins, including nucleic acid and DNA/RNA binding proteins, includes use of UV crosslinking or chemical cross-linkers, including e.g., cleavable cross-linkers dithiobis(succinimidylpropionate) and 3,3'-dithiobis(sulfosuccinimidyl-propionate) (McLaughlin, Am. J. Hum. Genet., 59:561-569, 1996; Tang, Biochemistry, 35:8216-8225, 1996; Lingner, Proc. Natl. Acad. Sci. U.S.A., 93:10712, 1996; and Chodosh, Mol. Cell. Biol., 6:4723-4733, 1986).

Further, modulation on binding ability of gp96 protein and AIMP1 protein or surface translocation of gp96 may be simply determined through a conventional protein-protein interaction detecting method. Such a method may be usefully used in the application of HTS (high-throughput screening). Herein, gp96 protein and AIMP1 protein, with which the testing agent contacts, each may be intracellularly expressed or injected, and may contact with the testing agent or its candidate in its in vitro unpurified, purified or partially purified state. Herein, the state of gp96 protein or AIMP1 protein may be appropriately selected according to an interaction inhibition measuring method.

The inhibition on the binding ability of gp96 protein and AIMP1 protein may be determined by a protein-protein interaction detection method known in the art, such as in vitro protein-protein binding assays (in vitro full-down assays), EMSA (electrophoretic mobility shift assays), immunoassays for protein binding, functional assays (phsophorylation assays, etc.), non-immunoprecipitation assays, immunoprecipitation western blotting assays, immuno-colocalization, cross-linking, affinity chromatography, immunoprecipitation (IP), yeast two-hybrid (Y2H), fluorescence resonance energy transfer (FRET), recombination of protein fragments (bimolecular fluorescence complementation, BiFC).

Further, by a protein chip, gp96 protein or AIMP1 protein may be microarrayed on a solid (such as metal, glass) surface, and then, another protein (e.g., AIMP1, in a case of fixation of gp96) and a candidate material together with the protein chip, may be cultured. Then, the inhibition of binding ability between gp96 protein and AIMP1 protein may be quickly analyzed in high throughput through a fluorescence analyzer, a SPR (Surface Plasmon Resonance), or a mass spectrometer such as MALDI (matrix assisted laser desorption/ionization)-TOF (time-of-flight)-MS (mass spectrometry), or SELDI (surface-enhanced laser desorption/ionization)-TOF-MS. Further, beside the protein chip, by using a compound chip fixed with a compound library, the binding ability between gp96 protein and AIMP1 protein may be analyzed in the same manner as described above.

The inventive analysis method, for example, yeast two hybrid analyses may be carried out using yeast expressing gp96 protein, AIMP1 protein, or parts or homologues of the proteins, fused with the DNA-binding domain of bacteria repressor LexA or yeast GAL4 and the transactivation domain of yeast GAL4 protein, respectively (KIM, M. J. et al., Nat. Gent., 34:330-336, 2003). The interaction between gp96 protein and AIMP1 protein reconstructs a transactivator inducing the expression of a reporter gene under the control by a promoter having a regulatory sequence binding to the DNA-binding domain of LexA protein or GAL4.

As described above, the reporter gene may be any gene known in the art encoding a detectable polypeptide (e.g., CAT (chloramphenicol acetyltransferase), luciferase, β-galactosidase, β-glucosidase, alkaline phosphatase, GFP (green fluorescent protein)). If the interaction (binding ability) between gp96 protein and AIMP1 protein, or parts or homologues of the proteins is facilitated or enhanced by a testing agent, the expression of the reporter gene increases more than under a normal condition. Conversely, if the interaction is inhibited or reduced by a testing agent, the reporter gene is not expressed or expressed less than under a normal condition.

Also, as a reporter gene, a reporter gene encoding a protein which enables growth of yeast (i.e., if the reporter gene is not expressed, the growth of yeast is inhibited) may be selected. For example, auxotropic genes encoding enzymes involved in biosynthesis for obtaining amino acids or nitrogenous bases (e.g., yeast genes such as ADE3, HISS, etc. or similar genes from other species) may be used. If the interaction of gp96 protein and AIMP1 protein expressed in this system, or parts or homologues of the proteins is inhibited or reduced by a testing agent, the reporter gene is not expressed or less expressed. Accordingly, under such a condition, the growth of yeast is stopped or retarded. Such an effect on the expression of the reporter gene may be observed with eyes or using devices (e.g., a microscope).

For the above mentioned operation on nucleotide and protein, see the following literatures: Maniatis et al., Molecular Cloning: A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press (1989); Deutscher, M., Guide to Protein Purification Methods Enzymology, vol. 182. Academic Press. Inc., San Diego, Calif. (1990).

For the synthesis of the inventive compound, a chemical synthesis method through an appropriate reaction using a raw material may be used. It should be understood that during the reaction process for the method, a specific substituent may require a protecting group in order to prevent an unwanted reaction from occurring. The person skilled in the art may know when such a protecting group is required, and how to dispose such a protecting group in the right position and then to remove it. The protecting group may be found in any one of general literatures, for example, ['Protective Groups in Organic Synthesis' Theodora Green, published by John Wiley & Sons]. The protecting group may be removed by methods appropriate for removal of a corresponding protecting group or any conventional methods known to the person skilled in the art. Herein, from among the methods for removing a protecting group, a method of which intramolecular interruption on a group at another position is minimized has to be selected.

Accordingly, when a reactant includes a group such as, amino, carboxyl or hydroxy, it is preferable to protect the group during a specific reaction mentioned in this specification. An example of a protecting group suitable for an amino or alkylamino group may be an acyl group, such as an alkanoyl group (e.g., acetyl), an alkoxycarbonyl group (e.g., methoxycarbonyl, ethoxycarbonyl, t-butoxycarbonyl groups), an arylmethoxycarbonyl group (e.g, benzyloxycarbonyl) or an aroyl group (e.g., benzoyl). Deprotection condition on the protecting group has to be changed according to the selection of a protecting group. Accordingly, for example, an acyl group, such as an alkanoyl group, an alkoxycarbonyl group or an aroyl group may be removed by hydrolysis using an appropriate base such as alkali metal hydroxide, e.g., lithium hydroxide or sodium hydroxide. Also, an acyl group, e.g., t-butoxycarbonyl group, may be removed by treatment with an appropriate acid such as hydrochloric acid, sulfuric acid, phosphoric acid or trifluoroacetic acid, and an arylmethoxycarbonyl group, e.g., a benzyloxycarbonyl group, may be removed by hydrogenation over catalyst, such as palladium on carbon, or treatment with Lewis acid such as boron tris (trifluoroacetate). An example of another protecting group suitable for a primary amino group may be a phthaloyl group, which may be removed by treatment with alkylamine, such as dimethyl aminopropylamine or treatment with hydrazine.

An Example of a protecting group suitable for a hydroxyl group may be an acyl group, such as an alkanoyl group (e.g., acetyl), an aroyl group (e.g., benzoyl), or an arylmethyl group (e.g., benzyl). Deprotection condition on the protecting group has to be changed according to the selection of a protecting group. Accordingly, for example, an acyl group, such as an alkanoyl or aroyl group, may be removed by hydrolysis using an appropriate base, such as alkali metal hydroxide (e.g., lithiuim, sodium hydroxide or ammonia). Also, an arylmethyl group, such as a benzyl group, may be removed by hydrogenation over catalyst, such as palladium on carbon.

Examples of a protecting group suitable for a carboxyl group, may include an esterified group, such as a methyl or ethyl group, that can be removed by hydrolysis using a base (e.g., sodium hydroxide), a t-butyl group that can be removed by treatment with acid (organic acid, e.g., trifluoroacetic acid), and a benzyl group that can be removed by hydrogenation over catalyst, such as palladium on carbon. A resin may be used as a protecting group.

The protecting group may be removed in any conventional step during synthesis by using a conventional technique known in the chemical field.

Meanwhile, hereinafter, Tables mentioned in the present invention will be described.

Table 1 shows chemicals inhibiting interaction of gp96 and AIMP1, which were obtained from a preliminary test.

Table 2 shows an inhibiting effect on interaction of gp96 and AIMP1 by the inventive compound.

Table 3 shows association rate constant ($K_a$), dissociation rate constant ($K_d$), and equilibrium dissociation constant ($K_D$) were determined for the interactions of GPM1 with various mutants of gp96 by the SPR experiments as described in Methods.

Table 4 shows numbers of total splenocytes isolated from vehicle- (n=9), GPM1- (n=9), and dexamethasone- (n=7) treated mice. Data represent the mean±S.D.

Meanwhile, NC1 used as a control in the present invention is the same as represented by Formula 16, which is 2-(4,6-dimethoxypyrimidin-2-yloxy)-3-phenylpropanoic acid.

[Formula 16]

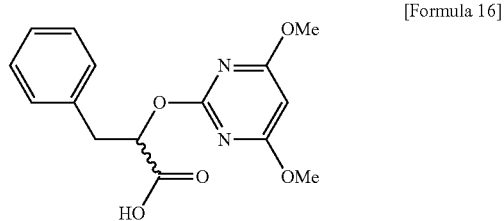 [SMILES: COc1cc(OC)nc(OC(Cc2ccccc2)C(=O)O)n1]

Hereinafter, the drawings of the present invention will be described.

FIGS. 1 to 9 represent suppression of cell surface gp96 by GPM1 reduces DC maturation and $B220^+$ population in gp96tm transgenic mice. (FIG. 1) Chemical structure of GPM1 (Formula 2) and negative control (NC1, Formula 16) used in this study. (FIG. 2) The dose-dependent effect of GPM1 or NC1 on the AIMP1-gp96 interaction using ELISA method as described. The indicated concentrations of the two compounds and biotin-conjugated murine gp96 were added to AIMP1 coated on the surface of microtiter wells, and gp96 bound to AIMP1 was detected with strepavidin-conjugated peroxidase. (FIG. 3) The binding of GPM1 to gp96 was examined by surface plasmon resonance (SPR). GPM1 at the indicated concentrations was injected to immobilized gp96 and the binding was measured using Biacore 3000. The response data were processed using data from a reference surface and buffer injections. Each concentration was tested in triplicate. (FIG. 4) RAW24.7 cells were treated with 10 μM GPM1 for 24 h. Cell lysates were immunoprecipitated with control IgG or anti-gp96 antibody and the immunoprecipitated proteins were immunoblotted with anti-KDELR1, antiAIMP1 and gp96 antibodies. WCL means whole cell lysate. (FIG. 5) Splenocytes isolated from C57BL/6 mice were treated with vehicle (5% DMSO in PBS), GPM1, or NC1 (10 μM, 24 h), stained for cell surface gp96, and followed by flow cytometry. (FIG. 6) $AIMP1^{+/+}$ or $AIMP1^{-/-}$ mouse splenocytes ($2\times10^5$ cells) were treated with vehicle, GPM1, or NC1 (10 μM, 24 h), fixed, and then co-cultured with WT bone marrow-derived DCs ($1\times10^4$ cells) for 16 h. TNFα secreted from BMDCs was quantified by ELISA. (FIG. 7) Percentage of $gp96^+$ MHC class $II^+$ cell population in splenocytes from gp96tm transgenic female mice treated with vehicle (control) (n=9), GPM1 (n=9), and dexamethasone (n=7) at 30 mg/kg. (FIG. 8) Cell surface ICOSL of $CD11b^+CD11c^+$ (myeloid DCs), $CD11b^-CD11c^+$ (lymphoid DCs), and $CD11b^+CD11c^-$ (macrophages) cell populations in splenocytes from gp96tm transgenic female mice treated with vehicle (n=9) and GPM1 (n=9) at 30 mg/kg. (FIG. 9) Percentage of $B220^+$, MHC class $II^+$, $CD4^+$, $CD8^+$, CD4 and CD8 double negative cell populations in splenocytes from gp96tm transgenic female mice treated with vehicle (n=9), GPM1 (n=9), and dexamethasone (n=7) at 30 mg/kg. Student t-test P values comparing GPM1-treated mice with control are indicated.

FIGS. 10 to 18 represent suppression of cell surface gp96 by GPM1 reduces renal disease and mature B cells, memory T cells, and activated T cells in gp96tm transgenic mice. Serum levels of nuclear antigen-specific (FIG. 10) and double strand DNA-specific antibody (FIG. 11) were compared between control (n=9), GPM1-(n=9) and dexamethasone (Dex)-treated (n=7) groups. Arbitrary units represent autoantibody absorbance at $OD_{450nm}$ at 1:101 serum dilution. (FIG. 12) Protein concentrations (mg/ml) in the urines of the three different groups. (FIG. 13) Representative kidney sections stained with hematoxylin and eosin from the three groups. (FIG. 14) Glomerular immunoglobulin deposition is shown by green fluorescence with FITC-conjugated goat anti-mouse Ig antibody in vehicle and GPM1-treated kidney. Percentage of $CD4^+CD44^{high}$ (memory T cells), $CD4^+CD62L^{low}$ (effector T cells), and $CD4^+CD69^+$ (activated T cells) in splenocytes (FIG. 15), $B220^+IgM^+IgD^+$ (mature B cells) population in splenocytes (FIG. 16), and $CD4^+CD25^+Foxp3^+$ regulatory T cells (FIG. 17) isolated from the three groups. (FIG. 18) Serum Ig levels from control (n=9), GPM1-(n=9), and Dex-treated (n=7) groups by ELISA. Total IgG1, IgG2a, IgG2b, IgG3, IgM, and IgA levels were determined using sandwich ELISA kits from Southern Biotechnology Associates (Birmingham, Ala.). Data represent the mean±S.D. Student t-test P values comparing GPM1-treated mice with control are shown.

FIG. 19 represents heat map of primary screening data. Inhibitory effects of 6,482 chemicals on the interaction of gp96 and AIMP1 were monitored by modified ELISA method as described. Taking the value of DMSO as 0%, the inhibition of each chemical was indicated as relative percentage and the degree of the inhibition was represented by a heat map in a 10% scale from 0 (green) to 100% (red).

FIG. 20 represents effect of the derivatives of the primary hits on surface expression of gp96. RAW264.7 cells were treated with 77 compounds (10 μM, 24 h) and the effects on surface expression of gp96 were analyzed by flow cytometry. The present inventors took over 5% changes compared to the control group as cut-off values. Out of 77 compounds, 8 compounds showed suppressive effect on surface expression of gp96 below 10% whereas 12 compounds showed increased gp96+ cells more than 20%.

FIG. 21 represents Synthesis of GPM1, (S)-methyl 2-(4, 6-dimethoxypyrimidin-2-yloxy)-3-methylbutanoate. (S)-Methyl 2-hydroxy-3-methylbutanoate (2). The α-hydroxy acid (409 mg, 3.46 mmol) was dissolved in toluene (28 ml) and methanol (17 ml). Concentrated hydrochloric acid (0.7 ml) was added and the reaction mixture was heated under reflux overnight. The reaction mixture was cooled to room temperature and concentrated in vacuo. The resulting residue was neutralized with saturated sodium hydrogen carbonate solution (35 ml) and extracted with ethyl acetate (3×35 ml). The combined organic layers were dried (MgSO$_4$), filtered and concentrated. Purification by Kugelrohr distillation gave the α-hydroxy esters as colorless oils. Hydroxy ester 2 (409 mg, 89% yield) became a white solid on standing: $^1$H NMR (300 MHz, CDCl$_3$): 4.05 (1H, d, J=3.7 Hz), 3.78 (3H, s), 3.13 (1H, br, OH), 2.07 (1H, m), 1.02 (3H, d, J=6.8 Hz), 0.88 (3H, d, J=6.8 Hz); m/z (LC) 133.11 (M$^+$).

(S)-Methyl 2-(4,6-dimethoxypyrimidin-2-yloxy)-3-methylbutanoate (4). Under argon, a well stirred suspension of (S)-methyl 2-hydroxy-3-methylbutanoate (409 mg, 3.09 mmol), 2-chloro-4,6-dimethoxypyrimidine (540 mg, 3.09 mmol), sodium ptoluenesulfinate (79 mg, 0.77 mmol) and potassium carbonate (641 mg, 4.64 mmol) in N,N-dimethylformamide (5 ml) was heated to 120° C. for 3 h (the conversion was followed by TLC). The reaction mixture was then concentrated in vacuo and the residue partitioned between water (5 ml) and dichloromethane (5 ml). The organic phase was separated and the aqueous phase extracted with dichloromethane (3 ml). The combined organic phase was washed with water (2 ml), dried (MgSO$_4$), filtered and concentrated. The desired product crysyallised and was dried under vacuum giving 676 mg (4, 81% yield) of white crystals: $^1$H NMR (300 MHz, CDCl$_3$): 5.70 (1H, s), 4.92 (1H, d, J=5.5 Hz), 3.93 (6H, t, J=9.2, 7.3 Hz), 3.72 (3H, s), 2.30 (1H, m), 1.11 (3H, d, J=6.8 Hz), 1.08 (3H, d, J=6.8 Hz); m/z (LC) 271.18 (M$^+$).

FIG. 22 represents the effect of point mutations on the ATPase activity of gp96. (a) The effect of gp96 point mutations on its ATPase activity was examined using ATPase assay kit (Innova Biosciences, Cambridge, UK). One unit is the amount of enzyme that catalyzes the reaction of 1 μmol of substrate per minute. The enzymatic activity was calculated according to manufacturer's instruction.

FIG. 23 represents the effect of GPM1 on the ATPase activity gp96. (a) The dose-dependent effect of GPM1 on the ATPase activity. The gp96 activity alone was 0.02066±0.00334 unit/ml and GPM1 showed little effect on the gp96 ATPase activity within the range of the tested concentration (0 vs. 100 μM, p=0.071).

FIG. 24 represents survival rate of gp96tm transgenic female mice treated with vehicle (n=9), GPM1 (n=9), and dexamethasone (n=9) at 30 mg/kg/day.

FIGS. 25 to 30 represent suppression of cell surface gp96 by GPM1 reduces DC maturation, B220+ and MHC class II$^+$ cells, memory T cells, and activated T cells in the lymph nodes of gp96tm transgenic mice. (FIG. 25) Percentages of ICOSL$^+$CD11b$^+$CD11c$^+$ cell population in lymph node cells from gp96tm transgenic female mice treated with vehicle (n=9), GPM1 (n=9), and dexamethasone (n=7) at 30 mg/kg. Percentages of B220$^+$ (FIG. 26), MHC class II$^+$ (FIG. 27), and CD4$^+$, CD8$^+$, CD4 and CD8 double negative (FIG. 28) cell populations in lymph nodes from gp96tm transgenic female mice treated with vehicle (n=9), GPM1 (n=9), and dexamethasone (n=7) at 30 mg/kg. (FIG. 29) Percentages of CD4$^+$CD44$^{high}$, CD4$^+$CD62L$^{low}$%, and CD4$^+$CD69$^+$ lymph node cells in vehicle- (n=9), GPM1- (n=9), and dexamethasone- (n=7) treated mice. (FIG. 30) Percentages of CD4$^+$CD25$^+$Foxp3$^+$ regulatory T cell population in lymph node cells from vehicle- (n=9), GPM1- (n=9), and dexamethasone- (n=7) treated mice. Student t-test P values comparing GPM1-treated mice with control are indicated.

FIGS. 31 to 33 represent increased cell surface expression of gp96 and serum level of gp96 antibody in human SLE patients. (FIG. 31) PBMCs of healthy control (n=6) or SLE patients (n=12) were analyzed for the surface presentation of gp96 and HLA-DR by flow cytometry. The numbers indicate the percentages of cells in the double positive quadrant. Shown is a representative data from each group. (FIG. 32) gp96+ HLADR+ population in PBMCs in control (n=6) or SLE patients (n=12) was statically analyzed (p=0.0005). (FIG. 33) Serum levels of total anti-gp96 autoantibody in healthy control (n=10) or SLE patients (n=10). Arbitrary units represent autoantibody absorbance at OD450 nm at 1:100 serum dilution. Student t-test P values comparing SLE patients with healthy control are indicated.

FIG. 34 is a graph showing a test result on a lupus symptom relieving effect of the inventive 2,4-pyrimidine derivatives in a lupus animal model. An NZB/W F1 mouse is a lupus animal model showing a voluntary lupus symptom. On the animal model, the effect of a 2,4-pyrimidine derivative was tested. Each group included 10 of 25-week aged male NZB/W F1 mouse. Each group was intraperiotneally administered with a control (5% DMSO solution) or a testing agent (2,4-pyrimidine derivative in a dose of 30 mg/kg) once a day. Except for mice which died by worsening of lupus symptoms, the ratio of surviving mice was analyzed. As a result, in a group administered with (S)-methyl 2-(4,6-dimethoxypyrimidin-2-yloxy)-3-methylbutanoate, the ratio of mice which died by lupus was significantly reduced. Accordingly, it was verified that in a generally used animal model, the 2,4-pyrimidine derivative has an effect in relieving the symptoms of lupus.

FIG. 35 is a graph showing an FACS analysis result using gp96 antibody, on the amount of gp96 protein existing on a cell surface, when HL-60 cell lines were treated with a 2,4-pyrimidine derivatives at a concentration of 1 mM for 24 hours. A compound of KR-S-015 is methyl 2-(4,6-dimethoxypyrimidin-2-yloxy)-3-methylbutanoate, and there are 15 kinds of compounds showing better effects than KR-S-015 (KR-S-008, KR-S-012, KR-S-001, KR-S-024, KR-S-023, KR-S-017, KR-S-011, KR-S-007, KR-S-013, KR-S-005, KR-S-009, KR-S-006, KR-S-020, KR-S-014, KR-S-022). It was determined that amide-type compounds (KR-S-001, KR-S-005, KR-S-006, KR-S-007, and KR-S-008) are better than ester (KR-S-010) or acid (KR-S-009). Meanwhile, it was determined that in ester-type compounds, as an intermediate substitute, methyl (KR-S-011, KR-S-012, KR-S-023, and KR-S-024) is better than isopropyl (KR-S-009, KR-S-010).

Advantageous Effects

The present inventors found novel materials that inhibit surface translocation of gp96 by mimicking a function of AIMP1 that is a molecular anchor for an intracellular residence of gp96, and then verified that the materials in vitro and in vivo relieve an SLE character, and have an effect on preventing and treating SLE. Accordingly, the present invention provides a novel method of screening a therapeutic agent for SLE, and for preventing or treating SLE by using the mechanism.

DESCRIPTION OF DRAWINGS

FIG. 1 shows chemical structures of GPM1 (Formula 2) and a negative control (NC1, Formula 16) used in the present research.

FIG. 2 shows a dose-dependent effect of GPM1 or NC1 on interaction between AIMP1-gp96, which was obtained by measurement using ELISA. To AIMP1 coated on a microtiter well, rodent gp96 bound to two materials and biotin was added according to the indicated concentration, and gp96 bound to AIMP1 was measured by peroxidase bound to streptavidin.

FIG. 3 shows a test result on binding GPM1 to gp96, which was obtained using Surface Plasmon Resonance (SPR). GPM1 at indicated concentrations was administered to fixed gp96, and the binding was measured by Biocore 3000. Response data were corrected by using data obtained from reference surface and buffer administration. For each concentration, 3 measurements were performed.

FIG. 4 shows a result when RAW24.7 cells were treated with 10 uM GPM1 for 24 hours and ruptured, and then immunoprecipitated with control IgG or anti-gp96 antibody. The immunoprecipitated protein was immunoblotted with anti-KDELR1, anti-AIMP1 and gp96 antibodies. WCL means whole cell lysate.

FIG. 5 shows a result when splenocytes C57BL/6 mice were separated, treated with an excipient (PBS containing 5% DMSO), GPM1 or NC1 at 10 uM for 24 hours, and flow cytometry of gp96 on cell surface was performed through staining.

FIG. 6 shows an ELISA measurement result on TNFα secretion in BMDC when AIMP1$^{+/+}$ or AIMP1$^{-/-}$ mouse splenocytes (2×10$^5$ cells) were fixed by treatment with an excipient, GPM1 or NC1 (10 uM, 24 h), and co-cultured with wild-type bone marrow-derived dendritic cells (1×10$^4$ cells, BMDC) for 16 hours.

FIG. 7 shows a measurement result of the ratio (percentage) of gp96$^+$ MHC class II$^+$ cells in splenocytes extracted from gp96tm transgenic female mice treated with excipient (control) (n=9), GPM1 (n=9) or dexamethasone (n=7) in a dose of 30 mg/kg.

FIG. 8 shows a measurement result of cell surface ICOSL distribution of CD11b$^+$CD11c$^+$ (myeloid dendritic cells), CD11b$^-$CD11c$^+$ (lymphoid dendritic cells) and CD11b$^+$CD11c$^-$ (macrophages) cell groups in splenocytes extracted from gp96tm transgenic female mice treated with excipient (control) (n=9) or GPM1 (n=9) in a dose of 30 mg/kg.

FIG. 9 shows a measurement result of the percentage of B220$^+$, MHC class II$^+$, CD4$^+$, CD8$^+$ cells and CD4-CD8 double negative cells in splenocytes extracted from gp96tm transgenic female mice treated with excipient (n=9), GPM1 (n=9) or dexamethasone (n=7) in a dose of 30 mg/kg.

FIG. 10 shows a measurement result of a level of nuclear antigen-specific antibody within serum, in which groups treated with control (n=9), GPM1 (n=9) and dexamethasone (n=7) are compared to each other. Arbitrary units indicate the absorbency of autoantibody, measured at OD$_{450\ nm}$ by serum diluted at 1:101.

FIG. 11 shows a measurement result of a level of double-stranded DNA-specific antibody within serum, in which groups treated with control (n=9), GPM1 (n=9) and dexamethasone (n=7) are compared to each other. Arbitrary units indicate the absorbency of autoantibody, measured at OD$_{450\ nm}$ by serum diluted at 1:101.

FIG. 12 shows protein levels (mg/ml) of urine in 3 different groups.

FIG. 13 shows representative kidney fragments of 3 groups stained with hematoxylin and eosin.

FIG. 14 shows photographs of glomerulus immunoglobulin deposition which occurs in kidneys treated with excipient and GPM1 by goat-anti-mouse Ig antibody bound to FITC.

FIG. 15 shows a measurement result of the number of CD4$^+$CD44$^{high}$ (memory T cells), CD4$^+$CD62L$^{low}$ (effective T cells) and CD4$^+$CD69$^+$ (active T cells) in splenocytes separated from three groups.

FIG. 16 shows a measurement result of the ratio of B220$^+$IgM$^+$IgD$^+$ (matured B cells) in splenocytes.

FIG. 17 shows a measurement result of the ratio of CD4$^+$CD25$^+$Foxp3$^+$ regulator T cells in splenocytes.

FIG. 18 shows a measurement result of serum Ig levels, such as total IgG1, IgG2a, IgG2b, IgG3, IgM and IgA levels, in groups treated with control (n=9), GPM1 (n=9) and dex (n=7), through sandwich ELISA kit of Southern Biotechnology Associates (Birmingham, Ala.). The value indicates an average±standard deviation.

FIG. 25 shows a percentage of ICOSL$^+$CD11b$^+$CD11c$^+$ cells in lymph node cells of gp96tm transgenic female mice treated with excipient (n=9), GPM1 (n=9) and dexamethasone (n=7) in a dose of 30 mg/kg.

FIG. 26 shows a percentage of B220$^+$ cells in lymph node cells of gp96tm transgenic female mice treated with excipient (n=9), GPM1 (n=9) and dexamethasone (n=7) in a dose of 30 mg/kg.

FIG. 27 shows a percentage of MHC class II$^+$ cells in lymph node cells of gp96tm transgenic female mice treated with excipient (n=9), GPM1 (n=9) and dexamethasone (n=7) in a dose of 30 mg/kg.

FIG. 28 shows a percentage of CD4+, CD8+ and CD4-CD8 double negative cells in lymph node cells of gp96tm transgenic female mice treated with excipient (n=9), GPM1 (n=9) and dexamethasone (n=7) in a dose of 30 mg/kg.

FIG. 29 shows a percentage of CD4+CD44$^{high}$, CD4+ CD62L$^{low}$ and CD4+CD69+ in lymph node cells of mice treated with excipient (n=9), GPM1 (n=9) and dexamethasone (n=7).

FIG. 30 shows a percentage of CD4+CD25+Foxp3+ regulator T cells in lymph node cells of mice treated with excipient (n=9), GPM1 (n=9) and dexamethasone (n=7).

FIG. 31 shows a flow cytometry result, which was performed to determine if gp96 and HLA-DR occurred on the surface of peripheral blood mononuclear cells (PBMC) of healthy control group (n=6) or SLE patient group (n=12). The number indicates a percentage of cells positioned at the double positive quadrant.

FIG. 32 shows an analysis result on the number of gp96+ HLA-DR+ in peripheral blood mononuclear cells of healthy control group (n=6) or SLE patient group (n=12) (p=0.0005).

FIG. 33 shows a measurement result of a serum level of total anti-gp96 autoantibody in healthy control group (n=10) or SLE patient group (n=10). Arbitrary units indicate the absorbency of autoantibody, measured at OD$_{450\ nm}$ by serum diluted at 1:100. P values of student t-test are shown, by which SLE patient group are compared to healthy control group.

MODE FOR INVENTION

Figure 1:
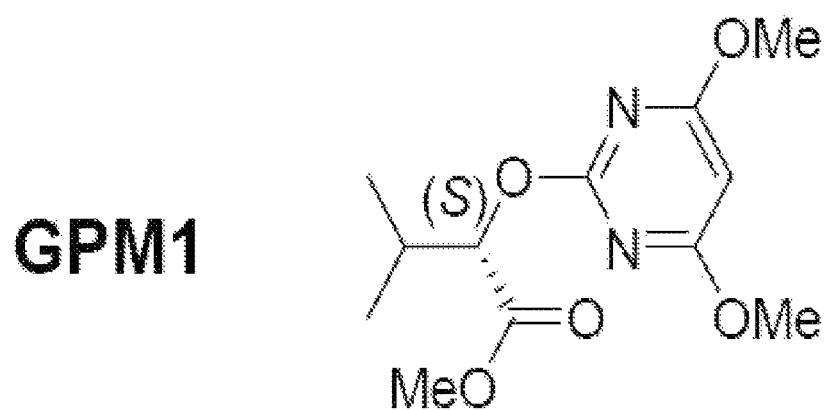
FIGS. 1 to 9 show that inhibition of gp96 on a cell surface by GPM1 causes a reduction in a maturing of dendritic cells (DC) and the number of B220$^+$ in a gp96tm transgenic mouse. P values of student t-test are shown, by which GPM1-treated mice are compared to control mice.
Figure 1:
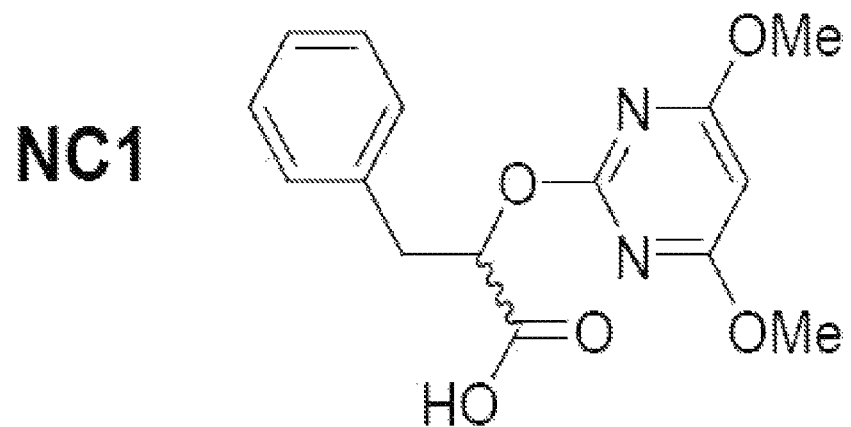

Hereinafter, the present invention will be described in detail with reference to following Examples.

However, the following Examples are only for illustrative purposes and are not intended to limit the scope of the invention.

Example 1

Preparation of the Inventive Organic Compounds

<1-1> Synthesis of 2-(2-chlobenzyloxy)-4,6-dimethoxypyrimidine 2-chlorobenzyl alcohol 2.85 g (0.02 mol) and 4,6-dimethoxypyrimidin-2-yl methyl sulfone 4.36 g (0.02 mol) were dissolved in DMF (N,N-dimethylformamide) 100 ml, and K$_2$CO$_3$ 3.3 g (1.2 eq) was added thereto. Then, the temperature was maintained at 95° C. while the mixture was stirred over night. The reacted solution was added to water 100 ml, extracted with diethyl ether, dried with MgSO$_4$, and distilled under reduced pressure to obtain residue. Through purification with Silica gel column chromatography, a yellow solid material 4.7 g (81%) was obtained: $^1$H NMR (CDCl$_3$); 3.73 (s, 6H), 5.20 (s, 2H), 6.22 (s, 1H), 7.07-7.20 (m, 4H).

<1-2> Synthesis of 2-(4,6-Dimethoxypyrimidin-2-yloxy)-2-phenylacetic acid

2-Phenylacetic acid methyl ester 3.30 g (0.02 mol) and 4,6-dimethoxypyrimidine-2-yl methyl sulfone 4.36 g (0.02 mol) were dissolved in DMF 100 ml, and K$_2$CO$_3$ 3.3 g (1.2 eq) was added thereto. Then, the temperature was maintained at 95° C. while the mixture was stirred over night. The reacted solution was added to water 100 ml, extracted with diethyl ether, dried with MgSO$_4$, and distilled under reduced pressure to obtain residue. Through purification with silica gel column chromatography, a solid material 4.87 g (80%) of 2-(4,6-Dimethoxypyrimidin-2-yloxy)-2-phenylacetic acid methyl ester was obtained. The obtained compound was dissolved in a mixed solvent of methanol and water (about 3:1), cooled with an ice bath, and added with LiOH.H$_2$O 0.96 g, followed by stirring for 30 minutes. After the ice bath was removed, the resultant product was reacted at room temperature for 2 hours, distilled under reduced pressure to remove methanol, and extracted with a small amount of diethyl ester. The water layer was neutralized with dilute hydrochloric acid to about PH 7, and then a solid was produced. Through filtration and drying, 2-(4,6-dimethoxypyrimidine-2-yloxy)-2-phenylacetic acid (4.41 g, 95%) was obtained: $^1$H NMR (CDCl$_3$); 3.73 (s, 6H), 5.85 (s, 1H), 6.22 (s, 1H), 7.19-7.37 (m, 5H), 12.34 (s, 1H).

<1-3> Synthesis of (R)-2-(4,6-dimethyoxypyrimidin-2-yloxy)-2-phenylacetic acid (R)-2-phenylacetic acid methyl ester 3.30 g (0.02 mol) and 4,6-dimethoxypyrimidine-2-yl methyl sulfone 4.36 g (0.02 mol) were dissolved in DMF 100 ml, and K$_2$CO$_3$ 3.3 g (1.2 eq) was added thereto. Then, the temperature was maintained at 95° C. while the mixture was stirred over night. The reacted solution was added to water 100 ml, extracted with diethyl ether, dried with MgSO$_4$, and distilled under reduced pressure to obtain residue. Through purification with silica gel column chromatography, a solid material 4.81 g (79%) of (R)-2-(4,6-dimethyoxypyrimidin-2-yloxy)-2-phenylacetic acid methyl ester was obtained. The obtained compound was dissolved in a mixed solvent of methanol and water (about 3:1), cooled with an ice bath, and added with LiOH.H$_2$O 0.96 g, followed by stirring for 30 minutes. After the ice bath was removed, the resultant product was reacted at room temperature for 2 hours, distilled under reduced pressure to remove methanol, and extracted with a small amount of diethyl ester. The water layer was neutralized with dilute hydrochloric acid to about PH 7, and then a solid was produced. Through filtration and drying, (R)-2-(4,6-dimethyoxypyrimidin-2-yloxy)-2-phenylacetic acid (4.45 g, 96%) was obtained: $^1$H NMR (CDCl$_3$); 3.73 (s, 6H), 5.85 (s, 1H), 6.22 (s, 1H), 7.19-7.37 (m, 5H), 12.34 (s, 1H).

<1-4> Synthesis of 2-(Benzyloxy)-4,6-dimethyoxypyrimidine-5-carboxamide benzyl alcohol 2.16 g (0.02 mol) and 5-carboxamide-4,6-dimethoxypyrimidin-2-yl methyl sulfone 5.52 g (0.02 mol) were dissolved in DMF 100 ml, and K$_2$CO$_3$ 3.3 g (1.2 eq) was added thereto. Then, the temperature was maintained at 95° C. while the mixture was stirred over night. The reacted solution was added to water 100 ml, extracted with diethyl ether, dried with MgSO$_4$, and distilled under reduced pressure to obtain residue. Through purification with silica gel column chromatography, a yellow solid material 4.34 g (75%) was obtained: $^1$H NMR (CDCl$_3$); 3.73 (s, 6H), 5.20 (s, 2H), 7.37-7.48 (m, 5H), 7.85 (s, 2H).

<1-5> Synthesis of 4,6-Dimethoxy-2-(pyridin-4-yloxy)pyrimidine

4-Hydroxypyridine 1.88 g (0.02 mol) and 4,6-dimethoxypyrimidine-2-yl methyl sulfone 4.36 g (0.02 mol) were dissolved in DMF 100 ml, and K$_2$CO$_3$ 3.3 g (1.2 eq) was added thereto. Then, the temperature was maintained at 95° C. while the mixture was stirred over night. The reacted solution was added to water 100 ml, extracted with diethyl ether, dried with MgSO$_4$, and distilled under reduced pressure to obtain residue. Through purification with silica gel column chromatography, a solid material 3.73 g (80%) was obtained: $^1$H NMR (CDCl$_3$); 3.73 (s, 6H), 5.49 (s, 1H), 6.85-8.42 (m, 4H).

<1-6> Synthesis of 3-(4,6-Dimethoxypyrimidin-2-yloxy)pyridin-2-amine 3-amino-4-hydroxypyridine 2.18 g (0.02 mol) and 4,6-dimethoxypyrimidine-2-yl methyl sulfone g (0.02 mol) were dissolved in DMF 100 ml, and K$_2$CO$_3$ 3.3 g (1.2 eq) was added thereto. Then, the temperature was maintained at 95° C. while the mixture was stirred over night. The reacted solution was added to water 100 ml, extracted with diethyl ether, dried with MgSO$_4$, and distilled under reduced pressure to obtain residue. Through purification with silica gel column chromatography, a solid material 4.02 g (81%) was obtained: $^1$H NMR (CDCl$_3$); 3.73° (s, 6H), 5.49 (s, 1H), 6.51 (s, 2H), 6.75-7.50 (m, 3H).

<1-7> Synthesis of (S)-methyl 2-(4,6-dimethoxypyrimidin-2-yloxy)-3-methylbutanoate (S)-methyl 2-hydrtoxy-3-methylbutanoate 2.62 g (0.02 mol) and 4,6-dimethoxypyrimidine-2-yl methyl sulfone 4.36 g (0.02 mol) were dissolved in DMF 100 ml, and K$_2$CO$_3$ 3.3 g (1.2 eq) was added thereto. Then, the temperature was maintained at 95° C. while the mixture was stirred over night. The reacted solution was added to water 100 ml, extracted with diethyl ether, dried with MgSO$_4$, and distilled under reduced pressure to obtain residue. Through purification with silica gel column chromatography, a colorless solid material 3.51 g (65%) was obtained: $^1$H NMR (CDCl$_3$); 1.01 (d, 6H), 2.97 (m, 1H), 3.67 (s, 3H), 3.73 (s, 6H), 4.51 (d, 1H), 6.13 (s, 1H).

<1-8> Synthesis of methyl 2-(4-bromophenyl)-2-(4,6-dimethoxypyrimidin-2-yloxy)acetate 2-(4-Bromophenyl)-2-(4,6-dimethoxypyrimidin-2-yloxy) acetate 4.88 g (0.02 mol) and 4,6-dimethoxypyrimidine-2-yl methyl sulfone 4.36 g (0.02 mol) were dissolved in DMF 100 ml, and K$_2$CO$_3$ 3.3 g (1.2 eq) was added thereto. Then, the temperature was maintained at 95° C. while the mixture was stirred over night. The reacted solution was added to water 100 ml, extracted with diethyl ether, dried with MgSO$_4$, and distilled under reduced pressure to obtain residue. Through purification with silica gel column chromatography, a solid material 5.59 g (73%): $^1$H NMR (CDCl$_3$); 3.67 (s, 3H), 3.73 (s, 6H), 5.81 (s, 1H), 6.22 (s, 1H), 7.08-7.36 (m, 4H).

<1-9> Synthesis of methyl 2-(4,6-dimethoxypyrimidin-2-yloxy)-3-methylbutanoate methyl 2-hydrtoxy-3-methylbutanoate 2.62 g (0.02 mol) and 4,6-dimethoxypyrimidine-2-yl methyl sulfone 4.36 g (0.02 mol) were dissolved in DMF 100 ml, and K$_2$CO$_3$ 3.3 g (1.2 eq) was added thereto. Then, the temperature was maintained at 95° C. while the mixture was stirred over night. The reacted solution was added to water 100 ml, extracted with diethyl ether, dried with MgSO$_4$, and distilled under reduced pressure to obtain residue. Through purification with silica gel column chromatography, a solid material 3.40 g (63%) was obtained: $^1$H NMR (CDCl$_3$); 1.01 (d, 6H), 2.97 (m, 1H), 3.67 (s, 3H), 3.73 (s, 6H), 4.51 (d, 1H), 6.13 (s, 1H).

<1-10> Synthesis of methyl 2-(4,6-dimethoxypyrimidin-2-yloxy)-2-(thiophen-2-yl)acetate methyl 2-(thiophen-2-yl)acetate 3.70 g (0.02 mol) and 4,6-dimethoxypyrimidine-2-yl methyl sulfone 4.36 g (0.02 mol) were dissolved in DMF 100 ml, and K$_2$CO$_3$ 3.3 g (1.2 eq) was added thereto. Then, the temperature was maintained at 95° C. while the mixture was stirred over night. The reacted solution was added to water 100 ml, extracted with diethyl ether, dried with MgSO$_4$, and distilled under reduced pressure to obtain residue. Through purification with silica gel column chromatography, a solid material 4.28 g (66%) was obtained: $^1$H NMR (CDCl$_3$); 1.30 (d, 3H), 3.73 (s, 6H), 4.12 (d, 2H), 5.81 (s, 1H), 6.22 (s, 1H), 6.60-6.91 (m, 3H).

<1-11> Synthesis of 4,6-Di-tert-butoxy-2-(pyridin-3-yloxy)pyrimidine 3-hydroxypyridine 1.90 g (0.02 mol) and 4,6-di-tert-butoxypyrimidin-2-yl methyl sulfone 6.05 g (0.02 mol) were dissolved in DMF 100 ml, and K$_2$CO$_3$ 3.3 g (1.2 eq) was added thereto. Then, the temperature was maintained at 95° C. while the mixture was stirred over night. The reacted solution was added to water 100 ml, extracted with diethyl ether, dried with MgSO$_4$, and distilled under reduced pressure to obtain residue. Through purification with silica gel column chromatography, a solid material 4.51 g (71%) was obtained: $^1$H NMR (CDCl$_3$); 1.43 (s, 18H), 5.49 (s, 1H), 7.38-8.56 (m, 4H).

<1-12> Synthesis of 2-(4,6-Dimethoxy-pyrimidin-2-yloxy)-N,N-diethyl-3-methyl-butyl amide (KR-S-001)

2-(4,6-Dimethoxy-pyrimidin-2-yloxy)-3-methyl-butyric acid 0.02 g (0.078 mmol) was charged, and Hydroxybenzotriazole (HOBT) 0.15 g (0.101 mmol) and diethyl amine 0.0085 g (0.117 mmol) were dissolved in methylene chloride (MC) 10 ml. In an ice bath, the resultant product was stirred for 10 minutes while the temperature was maintained at 0° C. After the stirring, EDCI (1-ethyl-3-(3-dimethylaminopropyl) carbodiimide) HCl 0.019 g (0.101 mmol) was slowly added thereto. The resultant mixture was stirred at a maintained temperature for 20 minutes. Then, after the temperature was raised up to room temperature, the resultant mixture was stirred for 3 hours. The reacted solution was distilled under reduced pressure to remove the solvent and obtain residue. Through purification with silica gel column chromatography, a target material 0.012 g (49%) was obtained:

¹H NMR (300 MHz, CDCl₃) δ: 1.15 (m, 12H), 2.31 (m, 1H), 3.41 (m, 2H), 3.45 (m, 2H), 3.93 (s, 6H), 5.22 (d, 1H), 5.71 (s, 1H).

<1-13> Synthesis of N-Butyl-2-(4,6-dimethoxy-pyrimidin-2-yloxy)-3-methyl-butyl amide (KR-S-002)

2-(4,6-Dimethoxy-pyrimidin-2-yloxy)-3-methyl-butyric acid 0.02 g (0.078 mmol) was charged, and HOBT 0.15 g (0.101 mmol) and butyl amine 0.0085 g (0.117 mmol) were dissolved in MC 10 ml. In an ice-bath, the resultant product was stirred for 10 minutes while the temperature was maintained at 0° C. After the stirring, EDCI HCl 0.019 g (0.101 mmol) was slowly added thereto. The resultant mixture was stirred at a maintained temperature for 20 minutes. Then, after the temperature was raised up to room temperature, the resultant mixture was stirred for 3 hours. The reacted solution was distilled under reduced pressure to remove solvent and obtain residue. Through purification with silica gel column chromatography, a target material 0.015 g (62%) was obtained: ¹H NMR (300 MHz, CDCl₃) δ: 1.08 (m, 3H), 1.23 (m, 6H), 1.30 (m, 2H), 1.43 (m, 2H), 2.34 (m, 1H), 3.26 (m, 2H), 3.91 (s, 6H), 5.33 (d, 2H), 5.74 (s, 1H), 6.27 (s, 1H).

<1-14> Synthesis of 2-(4,6-Dimethoxy-pyrimidin-2-yloxy)-3-methyl-N-phenyl-butyl amide (KR-S-003)

2-(4,6-Dimethoxy-pyrimidin-2-yloxy)-3-methyl-butyric acid 0.02 g (0.078 mmol) was charged, and HOBT 0.15 g (0.101 mmol) and aniline 0.011 g (0.117 mmol) were dissolved in MC 10 ml. In an ice-bath, the resultant product was stirred for 10 minutes while the temperature was maintained at 0° C. After the stirring, EDCI HCl 0.019 g (0.101 mmol) was slowly added thereto. The resultant mixture was stirred at a maintained temperature for 20 minutes. Then, after the temperature was raised up to room temperature, the resultant mixture was stirred for 3 hours. The reacted solution was distilled under reduced pressure to remove solvent and obtain residue. Through purification with silica gel column chromatography, a target material 0.017 g (66%) was obtained: ¹H NMR (300 MHz, CDCl₃) δ: 1.13 (m, 6H), 2.45 (m, 1H), 3.92 (s, 6H), 5.38 (d, 1H), 5.76 (s, 1H), 7.11 (t, 1H), 7.32 (t, 2H), 7.52 (d, 2H), 7.98 (s, 1H).

<1-15> Synthesis of N-Benzyl-2-(4,6-dimethoxy-pyrimidin-2-yloxy)-3-methyl-butyl amide (KR-S-004)

2-(4,6-Dimethoxy-pyrimidin-2-yloxy)-3-methyl-butyric acid 0.02 g (0.078 mmol) was charged, and HOBT 0.15 g (0.101 mmol) and benzyl amine 0.0125 g (0.117 mmol) were dissolved in MC 10 ml. In an ice-bath, the resultant product was stirred for 10 minutes while the temperature was maintained at 0° C. After the stirring, EDCI HCl 0.019 g (0.101 mmol) was slowly added thereto. The resultant mixture was stirred at a maintained temperature for 20 minutes. Then, after the temperature was raised up to room temperature, the resultant mixture was stirred for 3 hours. The reacted solution was distilled under reduced pressure to remove solvent and obtain residue. Through purification with silica gel column chromatography, a target material 0.02 g (74%) was obtained: ¹H NMR (300 MHz, CDCl₃) δ: 1.10 (m, 6H), 2.42 (m, 1H), 3.89 (s, 6H), 4.45 (d, 2H), 5.34 (d, 1H), 5.76 (s, 1H), 7.15 (s, 1H), 7.25 (m, 6H).

<1-16> Synthesis of 2-(4,6-dimethoxy-pyrimidin-2-yloxy)-N-isopropyl-3-methyl-butyl amide (KR-S-005)

2-(4,6-Dimethoxy-pyrimidin-2-yloxy)-3-methyl-butyric acid 0.02 g (0.078 mmol) was charged, and HOBT 0.15 g (0.101 mmol) and isopropyl amine 0.006 g (0.117 mmol) were dissolved in MC 10 ml. In an ice-bath, the resultant product was stirred for 10 minutes while the temperature was maintained at 0° C. After the stirring, EDCI HCl 0.019 g (0.101 mmol) was slowly added thereto. The resultant mixture was stirred at a maintained temperature for 20 minutes. Then, after the temperature was raised up to room temperature, the resultant mixture was stirred for 3 hours. The reacted solution was distilled under reduced pressure to remove solvent and obtain residue. Through purification with silica gel column chromatography, a target material 0.01 g (43%) was obtained: ¹H NMR (300 MHz, CDCl₃) δ: 1.07 (m, 9H), 1.12 (m, 3H), 2.37 (m, 1H), 4.07 (s, 6H), 4.11 (m, 1H), 5.28 (d, 1H), 5.74 (s, 1H), 6.07 (d, 1H).

<1-17> Synthesis of 2-(4,6-dimethoxy-pyrimidin-2-yloxy)-N-methoxy-3,N-dimethyl-butyl amide (KR-S-006)

2-(4,6-Dimethoxy-pyrimidin-2-yloxy)-3-methyl-butyric acid 0.02 g (0.078 mmol) was charged, and HOBT 0.15 g (0.101 mmol) and N,O-Dimethylhydroxylamine hydrochloride 0.0098 g (0.117 mmol) were dissolved in MC 10 ml. In an ice-bath, the resultant product was stirred for 10 minutes while the temperature was maintained at 0° C. After the stirring, EDCI HCl 0.019 g (0.101 mmol) was slowly added thereto. The resultant mixture was stirred at a maintained temperature for 20 minutes. Then, after the temperature was raised up to room temperature, the resultant mixture was stirred for 3 hours. The reacted solution was distilled under reduced pressure to remove solvent and obtain residue. Through purification with silica gel column chromatography, a target material 0.011 g (47%) was obtained: ¹H NMR (300 MHz, CDCl₃) δ: 1.11 (d, 6H), 1.68 (s, 1H), 2.34 (m, 1H), 3.89 (d, 6H), 5.39 (s, 1H), 5.68 (s, 1H).

<1-18> Synthesis of 2-(4,6-dimethoxy-pyrimidin-2-yloxy)-3-methyl-1-piperidin-1-yl-butan-1-one (KR-S-007)

2-(4,6-Dimethoxy-pyrimidin-2-yloxy)-3-methyl-butyric acid 0.02 g (0.078 mmol) was charged, and HOBT 0.15 g (0.101 mmol) and piperidine 0.0125 g (0.117 mmol) were dissolved in MC 10 ml. In an ice-bath, the resultant product was stirred for 10 minutes while the temperature was maintained at 0° C. After the stirring, EDCI HCl 0.019 g (0.101 mmol) was slowly added thereto. The resultant mixture was stirred at a maintained temperature for 20 minutes. Then, after the temperature was raised up to room temperature, the resultant mixture was stirred for 3 hours. The reacted solution was distilled under reduced pressure to remove solvent and obtain residue. Through purification with silica gel column chromatography, a target material 0.011 g (43%) was obtained: ¹H NMR (300 MHz, CDCl₃) δ: 1.11 (d, 6H), 1.52 (m, 6H), 2.34 (m, 1H), 3.34 (m, 4H), 3.89 (s, 6H), 4.62 (s, 1H), 6.08 (s, 1H).

<1-19> Synthesis of 2-(4,6-dimethoxy-pyrimidin-2-yloxy)-3-methyl-1-morpholin-4-yl-butan-1-one (KR-S-008)

2-(4,6-Dimethoxy-pyrimidin-2-yloxy)-3-methyl-butyric acid 0.02 g (0.078 mmol) was charged, and HOBT 0.15 g (0.101 mmol) and morpholine 0.0125 g (0.117 mmol) were dissolved in MC 10 ml. In an ice-bath, the resultant product was stirred for 10 minutes while the temperature was maintained at 0° C. After the stirring, EDCI HCl 0.019 g (0.101 mmol) was slowly added thereto. The resultant mixture was stirred at a maintained temperature for 20 minutes. Then, after the temperature was raised up to room temperature, the resultant mixture was stirred for 3 hours. The reacted solution was distilled under reduced pressure to remove solvent and obtain residue. Through purification with silica gel column chromatography, a target material 0.013 g (51%) was obtained: $^1$H NMR (300 MHz, CDCl$_3$) δ: 1.11 (d, 6H), 1.68 (s, 1H), 2.34 (m, 1H), 3.89 (d, 6H), 5.39 (s, 1H), 5.68 (s, 1H).

<1-20> Synthesis of 2-(4,6-dimethoxy-pyrimidin-2-yloxy)-3-methyl-butyric acid (KR-S-009)

2-(4,6-Dimethoxy-pyrimidin-2-yloxy)-3-methyl-butyric acid methyl ester 1 g (3.7 mmol) was dissolved in MeOH/H$_2$O (3:1) 40 ml, and LiOH 0.233 g (5.55 mmol) was added thereto, followed by stirring at room temperature for 5 hours. The reacted solution was distilled under reduced pressure, and acidified with 2N HCl solution to pH 3 to 4. The resultant product was extracted with EA and water three times, the organic layer was dried with MgSO$_4$, and the solvent was removed under reduced-pressure. Through purification with silica gel column chromatography, a target material 0.66 g (70%) was obtained: $^1$H NMR (300 MHz, CDCl$_3$) δ: 1.13 (m, 6H), 2.56 (s, 1H), 347 (m, 4H), 3.67 (m, 4H), 3.89 (s, 6H), 4.62 (s, 1H) 6.08 (s, 1H).

<1-21> Synthesis of 2-(4,6-Dimethoxy-pyrimidin-2-yloxy)-3-methyl-butyric acid methyl ester (KR-S-010)

2-Hydroxy-3-methyl-1-butyric acid methyl ester 1.4 g (0.01 mol) and 2-Chloro-4,6-dimethoxy-pyrimidine 1.74 g (0.01 mol) were dissolved in DMF (Dimethyl fumarate) 20 ml, K$_2$CO$_3$ 2 g (1.5 eq) was added thereto, and sodium methane sulfinate 0.26 g (0.25 eq) was added thereto, followed by stirring at 120° C. for 5 hours. The reacted solution was cooled to room temperature, and distilled under reduced pressure to obtain residue. The residue was extracted with cold water and MC three times, the MC layer was dried with MgSO$_4$, and the solvent was removed under reduced-pressure. Through purification with silica gel column chromatography, a target material 1.7 g (63%) was obtained: $^1$H NMR (300 MHz, CDCl$_3$) δ: 1.08 (m, 6H), 2.28 (m, 1H), 3.71 (s, 3H), 3.89 (s, 6H), 4.89 (d, 1H), 5.71 (s, 1H).

<1-22> Synthesis of L-2-(4,6-Dimethoxy-pyrimidin-2-yloxy)-propionic acid methyl ester (KR-S-011)

L-methyl lactate 0.46 g (0.005 mol) and 2-Chloro-4,6-dimethoxy-pyrimidine 0.88 g (0.005 mol) were dissolved in DMF 20 ml, K$_2$CO$_3$ 0.52 g (0.75 eq) was added thereto, and sodium methane sulfate 0.1 g was added thereto, followed by stirring at 120° C. for 5 hours. The reacted solution was cooled to room temperature, and distilled under reduced pressure to obtain residue. The residue was extracted with cold water and ethylacetate (EA) three times, and washed with brine twice, the organic layer was dried with MgSO$_4$, and the solvent was removed under reduced-pressure. Through purification with silica gel column chromatography, a target material 0.66 g (54%) was obtained: $^1$H NMR (300 MHz, CDCl$_3$) δ: 1.63 (d, 3H), 3.73 (s, 3H), 3.89 (s, 6H), 5.22 (q, 1H), 5.72 (s, 1H).

<1-23> Synthesis of D-2-(4,6-Dimethoxy-pyrimidin-2-yloxy)-propionic acid methyl ester (KR-S-012)

D-methyl lactate 0.46 g (0.005 mol) and 2-Chloro-4,6-dimethoxy-pyrimidine 0.88 g (0.005 mol) were dissolved in DMF 20 ml, K$_2$CO$_3$ 0.52 g (0.75 eq) was added thereto, and sodium methane sulfate 0.1 g was added thereto, followed by stirring at 120° C. for 5 hours. The reacted solution was cooled to room temperature, and distilled under reduced pressure to obtain residue. The residue was extracted with cold water and ethylacetate three times, and washed with brine twice, the organic layer was dried with MgSO$_4$, and the solvent was removed under reduced-pressure. Through purification with silica gel column chromatography, a target material 0.56 g (46%) was obtained: $^1$H NMR (300 MHz, CDCl$_3$) δ: 1.63 (d, 3H), 3.73 (s, 3H), 3.89 (s, 6H), 5.22 (q, 1H), 5.72 (s, 1H).

<1-24> Synthesis of 2-(4,6-Dimethoxy-pyrimidin-2-yloxy)-2-methyl-propionic acid methyl ester (KR-S-013)

Methyl 2-hydroxy isobutyrate 0.52 g (0.005 mol) and 2-chloro-4,6-dimethoxy-pyrimidine 0.88 g (0.005 mol) were dissolved in DMF 20 ml, K$_2$CO$_3$ 0.52 g (0.75 eq) was added thereto, and sodium methane sulfate 0.1 g was added thereto, followed by stirring at 120° C. for 5 hours. The reacted solution was cooled to room temperature, and distilled under reduced pressure to obtain residue. The residue was extracted with cold water and ethylacetate three times, and washed with brine twice, the organic layer was dried with MgSO$_4$, and the solvent was removed under reduced-pressure. Through purification with silica gel column chromatography, a target material 0.14 g (12%) was obtained: $^1$H NMR (300 MHz, CDCl$_3$) δ: 1.72 (s, 6H), 3.66 (s, 3H), 3.93 (s, 6H), 5.7 (s, 1H).

<1-25> Synthesis of D-3-(4,6-Dimethoxy-pyrimidin-2-yloxy)-butyric acid methyl ester (KR-S-014)

D-Methyl 3-hydroxy butyrate 0.52 g (0.005 mol) and 2-Chloro-4,6-dimethoxy-pyrimidine 0.88 g (0.005 mol) were dissolved in DMF 20 ml, K$_2$CO$_3$ 0.52 g (0.75 eq) was added thereto, and sodium methane sulfate 0.1 g was added thereto, followed by stirring at 120° C. for 5 hours. The reacted solution was cooled to room temperature, and distilled under reduced pressure to obtain residue. The residue was extracted with cold water and ethylacetate three times, and washed with brine twice, the organic layer was dried with MgSO$_4$, and the solvent was removed under reduced-pressure. Through purification with silica gel column chromatography, a target material 0.15 g (12%) was obtained: $^1$H NMR (300 MHz, CDCl$_3$) δ: 1.43 (d, 2H), 1.63 (d, 3H), 3.73 (s, 3H), 3.89 (s, 6H), 5.22 (q, 1H), 5.72 (s, 1H).

<1-26> Synthesis of L-2-(4,6-Dimethoxy-pyrimidin-2-yloxy)-3-methyl-butyric acid methyl ester (KR-S-015)

L-2-hydroxy-3-methyl-butyric acid methyl ester 0.7 g (0.0053 mol) and 2-Chloro-4,6-dimethoxy-pyrimidine 0.9 g (0.0053 mol) were dissolved in DMF 20 ml, K$_2$CO$_3$ 0.6 g was added thereto, and sodium methane sulfate 0.1 g was added thereto, followed by stirring at 120° C. for 5 hours. The reacted solution was cooled to room temperature, and distilled under reduced pressure to obtain residue. The residue was extracted with cold water and ethylacetate three times, and washed with brine twice, the organic layer was dried with MgSO$_4$, and the solvent was removed under reduced-pressure. Through purification with silica gel column chromatography, a target material 0.5 g (33%) was obtained: $^1$H NMR (300 MHz, CDCl$_3$) δ: 1.11 (m, 7H), 3.71 (s, 3H), 3.89 (s, 6H), 4.91 (d, 1H), 5.71 (s, 1H).

<1-27> Synthesis of 4,6-Dimethoxy-pyrimidin-2-yloxy)-phenyl-acetic acid methyl ester (KR-S-016)

Hydroxyphenyl acetic acid methyl ester 2.3 g (0.0138 mol) and 2-Chloro-4,6-dimethoxy-pyrimidine 2.4 g (0.0138 mol) were dissolved in DMF 30 ml, K$_2$CO$_3$ 2.9 g (1.5 eq) was added thereto, and sodium methane sulfinate 0.36 g (0.25 eq) was added thereto, followed by stirring at 120° C. for 5 hours. The reacted solution was cooled to room temperature, and distilled under reduced pressure to obtain residue. The residue was extracted with cold water and MC three times, and the MC layer was dried with MgSO$_4$, and the solvent was removed under reduced-pressure. Through purification with silica gel column chromatography, a target material 2.4 g (57%) was obtained: $^1$H NMR (300 MHz, CDCl$_3$) δ: 3.72 (s, 3H), 3.87 (s, 6H), 5.75 (s, 1H), 6.06 (s, 1H), 7.35 (m, 3H), 7.59 (m, 2H).

<1-28> Synthesis of 4,6-Dimethoxy-pyrimidin-2-yloxy)-phenyl-acetic acid (KR-S-017)

To MeOH/H$_2$O (3:1) 40 ml, 4,6-Dimethoxy-pyrimidin-2-yloxy)-phenyl-acetic acid methyl ester 1 g (3.7 mmol) was added, and LiOH 0.233 g (5.55 mmol) was added, followed by stirring at room temperature for 5 hours. The reacted solution was distilled under reduced pressure, and acidified with 2N HCl solution to pH 3 to 4. The resultant product was extracted with Ethyl acetate and H$_2$O three times, and was dried with MgSO$_4$, and the solvent was removed under reduced-pressure. Through purification with silica gel column chromatography, a target material 0.66 g (54%) was obtained: $^1$H NMR (300 MHz, CDCl$_3$) δ: 3.45 (s, 1H), 3.79 (s, 6H), 5.65 (s, 1H), 6.01 (s, 1H), 7.24 (m, 5H).

<1-29> Synthesis of 2-(4,6-Dimethoxy-pyrimidin-2-yloxy)-N-isopropyl-2-phenyl-acetamide (KR-S-018)

4,6-Dimethoxy-pyrimidin-2-yloxy)-phenyl-acetic acid 0.02 g (0.069 mmol) was charged, and HOBT 0.15 g (0.090 mmol) and isopropyl amine 0.006 g (0.104 mmol) were dissolved in MC 10 ml. In an ice-bath, the resultant product was stirred for 10 minutes while the temperature was maintained at 0° C. EDCI HCl 0.017 g (0.090 mmol) was slowly added thereto. The resultant mixture was stirred at a maintained temperature for 20 minutes. Then, after the temperature was raised up to room temperature, the resultant mixture was stirred for 3 hours. The reacted solution was distilled under reduced pressure to remove solvent and obtain residue. Through purification with silica gel column chromatography, a target material 0.003 g (13%) was obtained: $^1$H NMR (300 MHz, CDCl$_3$) δ: 1.25 (m, 6H), 1.60 (m, 6H), 4.07 (s, 6H), 4.11 (m, 1H), 5.2 (s, 1H), 5.74 (s, 1H), 6.37 (s, 1H), 6.53 (s, 1H), 7.37 (m, 3H), 7.56 (m, 2H).

<1-30> Synthesis of N-Benzyl-2-(4,6-dimethoxy-pyrimidin-2-yloxy)-2-phenyl-acetamide (KR-S-019)

4,6-Dimethoxy-pyrimidin-2-yloxy)-phenyl-acetic acid 0.02 g (0.069 mmol) was charged, and HOBT 0.15 g (0.090 mmol) and benzyl amine 0.0111 g (0.104 mmol) were dissolved in MC 10 ml. In an ice-bath, the resultant product was stirred for 10 minutes while the temperature was maintained at 0° C. EDCI HCl 0.017 g (0.090 mmol) was slowly added thereto. The resultant mixture was stirred at a maintained temperature for 20 minutes. Then, after the temperature was raised up to room temperature, the resultant mixture was stirred for 3 hours. The reacted solution was distilled under reduced pressure to remove solvent and obtain residue. Through purification with silica gel column chromatography, a target material 0.010 g (38%) was obtained: $^1$H NMR (300 MHz, CDCl$_3$) δ: 1.25 (s, 1H), 1.60 (s, 2H), 3.86 (s, 6H), 4.47 (m, 1H), 5.12 (s, 1H), 5.74 (s, 1H), 6.37 (s, 1H), 6.53 (s, 1H), 7.00 (t, 1H) 7.37 (m, 8H), 7.56 (m, 2H).

<1-31> Synthesis of N-Butyl-2-(4,6-dimethoxy-pyrimidin-2-yloxy)-2-phenyl-acetamide (KR-S-020)

4,6-Dimethoxy-pyrimidin-2-yloxy)-phenyl-acetic acid 0.02 g (0.069 mmol) was charged, and HOBT 0.15 g (0.090 mmol) and butyl amine 0.0076 g (0.104 mmol) were dissolved in MC 10 ml. In an ice-bath, the resultant product was stirred for 10 minutes while the temperature was maintained at 0° C. EDCI HCl 0.017 g (0.090 mmol) was slowly added thereto. The resultant mixture was stirred at a maintained temperature for 20 minutes. Then, after the temperature was raised up to room temperature, the resultant mixture was stirred for 3 hours. The reacted solution was distilled under reduced pressure to remove solvent and obtain residue. Through purification with silica gel column chromatography, a target material 0.023 g (96%) was obtained: $^1$H NMR (300 MHz, CDCl$_3$) δ: 1.08 (m, 3H), 1.30 (m, 2H), 1.43 (m, 2H) 2.34 (m, 1H), 3.26 (m, 2H) 3.86 (s, 6H), 4.47 (m, 1H), 5.12 (s, 1H), 5.74 (s, 1H), 6.37 (s, 1H), 6.53 (s, 1H), 7.37 (m, 3H), 7.56 (m, 2H).

<1-32> Synthesis of 2-(4,6-Dimethoxy-pyrimidin-2-yloxy)-N,N-diethyl-2-phenyl-acetamide (KR-S-021)

(4,6-Dimethoxy-pyrimidin-2-yloxy)-phenyl-acetic acid 0.02 g (0.069 mmol) was charged, and HOBT 0.15 g (0.090 mmol) and Diethyl amine 0.0076 g (0.104 mmol) were dissolved in MC 10 ml. In an ice-bath, the resultant product was stirred for 10 minutes while the temperature was maintained at 0° C. EDCI HCl 0.017 g (0.090 mmol) was slowly added thereto. The resultant mixture was stirred at a maintained temperature for 20 minutes. Then, after the temperature was raised up to room temperature, the resultant mixture was stirred for 3 hours. The reacted solution was distilled under reduced pressure to remove solvent and obtain residue. Through purification with silica gel column chromatography, a target material 0.010 g (42%) was

<1-33> Synthesis of L-2-(4,6-Dimethoxy-pyrimidin-2-yloxy)-3-methyl-butyric acid (KR-S-022)

L-2-(4,6-dimethoxy-pyrimidine-2-yloxy)-3-methyl-butyric acid methyl ester 0.06 g (0.00025 mol) was dissolved in about 3 ml of MeOH, and 20% NaOH 0.5 ml was added thereto. The resultant solution was heated at 50-60° C. for 2 hours. The solution was cooled to room temperature, and added with 10 ml of water. The organic layer was separated with n-hexane 15 ml, and the aqueous solution was added with 0.5 ml of concentrated HCl, extracted with ethylacetate 30 ml, and washed with brine three times. The ethylacetate layer was separated, and dried with $MgSO_4$, and the solvent was removed under reduced-pressure. Then, a target material 0.04 g (71%) was obtained: $^1$H NMR (300 MHz, $CDCl_3$) δ: 1.11 (m, 6H), 3.84 (s, 6H), 4.89 (d, 1H), 5.73 (s, 1H), 10.19 (s, 1H).

<1-34> Synthesis of D-2-(4,6-Dimethoxy-pyrimidin-2-yloxy)-propionic acid (KR-S-023)

D-2-(4,6-dimethoxy-pyrimidine-2-yloxy)-propionic acid methyl ester 0.06 g (0.00025 mol) was dissolved in about 3 ml of MeOH, and 20% NaOH 0.5 ml was added thereto. The resultant solution was heated at 50-60° C. for 2 hours. The solution was cooled to room temperature, and added with 10 ml of water. The organic layer was separated with n-hexane 15 ml, and the aqueous solution was added with 0.5 ml of concentrated HCl, extracted with ethylacetate 30 ml, and washed with brine three times. The ethylacetate layer was dried with $MgSO_4$, and the solvent was removed under reduced-pressure. Then, a target material 0.04 g (71%) was obtained: $^1$H NMR (300 MHz, $CDCl_3$) δ: 1.63 (d, 3H), 3.89 (s, 6H), 5.22 (q, 1H), 5.72 (s, 1H), 10.19 (s, 1H).

<1-35> Synthesis of L-2-(4,6-Dimethoxy-pyrimidin-2-yloxy)-propionic acid (KR-S-024)

L-2-(4,6-dimethoxy-pyrimidine-2-yloxy)-propionic acid methyl ester 0.08 g (0.0003 mol) was dissolved in about 3 ml of MeOH, and 20% NaOH 0.5 ml was added thereto. The resultant solution was heated at 50-60° C. for 2 hours. The solution was cooled to room temperature, and added with 10 ml of water. The organic layer was separated with n-hexane 15 ml, and the aqueous solution was added with 0.5 ml of concentrated HCl, extracted with ethylacetate 30 ml, and washed with brine three times. The ethylacetate layer was dried with $MgSO_4$, and the solvent was removed under reduced-pressure. Then, a target material 0.06 g (87%) was obtained: $^1$H NMR (300 MHz, $CDCl_3$) δ: 1.63 (d, 3H), 3.89 (s, 6H), 5.22 (q, 1H), 5.72 (s, 1H), 10.19 (s, 1H).

Comparative Example 1

Synthesis of 2-(4,6-Dimethoxypyrimidin-2-yloxy)-3-phenylpropionic acid 2-(4,6-Dimethoxypyrimidin-2-yloxy)-3-phenylpropionic acid methyl ester 3.58 g (0.02 mol) and 4,6-dimethoxypyrimidine-2-yl methyl sulfone 4.36 g (0.02 mol) were dissolved in DMF 100 ml, and $K_2CO_3$ 3.3 g (1.2 eq) was added thereto. Then, the temperature was maintained at 95° C. while the mixture was stirred over night. The reacted solution was added to water 100 ml, extracted with diethyl ether, dried with $MgSO_4$, and distilled under reduced pressure to obtain residue. Through purification with silica gel column chromatography, a solid material 5.16 g (81%) of 2-(4,6-dimethoxypyrimidin-2-yloxy)-2-phenylpropionic acid methyl ester was obtained. The obtained compound was dissolved in a mixed solvent of methanol and water (about 3:1), cooled with an ice bath, and added with LION. $H_2O$ 0.96 g, followed by stirring for 30 minutes. After the ice bath was removed, the resultant product was reacted at room temperature for 2 hours, distilled under reduced pressure to remove methanol, and extracted with a small amount of diethyl ester. The water layer was neutralized with dilute hydrochloric acid to about PH 7, and then a solid was produced. Through filtration and drying, 2-(4,6-dimethoxy-pyrimidine-2-yloxy)-2-phenylpropionic acid 4.35 g (88%) was obtained: $^1$H NMR ($CDCl_3$); 3.08 (dd, 1H) 3.33 (dd, 1H), 3.73 (s, 6H), 4.95 (d, 1H), 6.13 (s, 1H) 7.12-7.26 (m, 5H), 12.34 (s, 1H).

Example 2

Analysis for Effects of the Inventive Compounds

<Experimental Methods>
1. Human Blood

The patients involved in this study were enrolled at the Rheumatology Clinic, Department of Internal Medicine at Seoul National University Hospital. Human blood was obtained from 22 patients with SLE, and 16 healthy individuals. PBMCs (Peripheral Blood Mononuclear Cells) were isolated using Ficoll-Paque Plus (GE healthcare). Patients met the following criteria for their diseases: the 1997 update of the American College of Rheumatology revised criteria for the classification of SLE. This study was approved by Institutional Review Board of Seoul National University Hospital.

2. Drug Administration

Female gp96tm transgenic mice (Proc Natl Acad Sci USA. 2003 December 23; 100(26): 15824-15829) were bred and maintained at the animal center for pharmaceutical research, Seoul National University. We used age-matched, 12-26 weeks old mice in each experimental group. To suppress cell surface gp96 we used GPM1 compound. Dexamethasone and GPM1 were dissolved in 5% DMSO in phosphate-buffered saline (PBS) and control vehicle was 5% DMSO in PBS. Compounds were administered i.p. every 24 h for 2 months (30 mg/kg/day). Three groups of each 9 mice were examined. All procedures were conducted in accordance with the Guide for the Care and Use of Laboratory Animals, published by the Korean National Institute of Health.

3. Flow Cytometry

Spleen and lymph node cell suspensions were prepared by grindling tissue through sterile mesh and erythrocytes were lysed with RBC lysis buffer (eBioscience, CA). For surface staining, antibodies were fluoresceinisothiocyanate (FITC)-, phycoerythrin (PE)-, PerCP-, or APC-conjugated. Antibodies used were CD4 (RM4-5, H129.12), CD8 (53-6,7), B220 (RA3-6B2), CD11b (M1/70), CD11c (HL3), CD44 (IM7), CD62L (MEL-14), CD69 (H1.2F3), CD25 (PC61.5), IgM (11/41), IgD (11-26C.2a) (BD Pharmingen, CA), MHC class II (M5/114.15.2), Foxp3 (FJK-16s) (eBioscience, CA), and gp96 (Santacruz, Calif.). After staining, cells were washed and analyzed on a FACS can flow cytometer using CellQuest software (BD Bioscience, Mountain View, Calif.).

4. DC Maturation Assay

Bone marrow-derived immature dendritic cells ($1 \times 10^4$) from WT mice were stimulated with fixed, GPM1 or NC-1-treated splenocytes ($2 \times 10^5$) from wild type or AIMP1$^{-/-}$ mice for 16 h. Culture supernatants were collected for TNFα assay using ELISA kit from Pierce Biotechnology Inc. (Rockford, Ill.).

5. ELISA Assay for Chemical Screening 96-well plates (Maxisorp., F96; Nunc) were coated with 500 ng/well AIMP1 in PBS (pH 7.4). After washing, the remaining sites were blocked with PBS containing 1% BSA for 1 h. Binding of 10 ng/well biotin-conjugated gp96 was performed in Tris buffer (25 mM Tris, 10 mM NaCl and 0.4% Triton X-100). Each of the 6,580 compounds was added to the well at 100 nM and the plates were washed and incubated with HRP conjugated streptavidin in PBS containing 0.1% BSA and 0.1% Tween 20 for 30 min. The plates were washed, and then substrate was added to each well. The absorbance was monitored at 450 nm.

6. Histology

Kidney tissue sections of gp96tm transgenic mice were fixed in 10% formaldehyde in PBS and dehydrated using an alcohol gradient. After paraffin infiltration, the tissues were sectioned using a microtome, stained with hematoxylin and eosin (H&E) and analyzed by light microscopy. For immunofluorescent staining, kidneys were sectioned with a cryostat. These cryosections were blocked with normal goat serum, stained with FITC-conjugated goat anti-mouse Ig (BD pharmingen, CA), and then observed by fluorescent microscopy.

7. Surface Plasmon Resonance (SPR)

Human gp96 was expressed as His tag fusion protein in *Escherichia coli* BL21 (DE3) and purified by nickel affinity chromatography. His-tagged human gp96 was immobilized onto CM5 sensor chips using standard amine coupling2. PBS was used as a running buffer. The carboxymethyl dextran surface within one side of the flow cell was activated with a 7-min injection of a 1:1 ratio of 0.4M EDC and 0.1M NHS. The protein was coupled to the surface with a 7-min injection of gp96 diluted in 10 mM sodium acetate, pH 3.7. Remaining activated groups were blocked with a 7-min injection of 1.0M ethanolamine, pH 8.5. GPM1 compound was dissolved directly in the PBS running buffer containing 1% DMSO and injected at a flow rate of 20 μl/min at 25° C. and the binding was determined by the change in resonance units (RU). The compound concentration varied from 10 nM to 25 μM and each concentration was tested at least three times. All of the bound complexes dissociated back to baseline within a reasonable time frame. Therefore, no regeneration was required. Sensorgram was processed by subtracting the binding response recorded from the control surface, followed by subtracting an average of the buffer blank injections from the reaction spot. To determine kinetic rate constants, all data sets were fit to a simple 1:1 binding with drifting baseline model using BIAevaluation program.

8. Measuring Survival Rate of a Lupus Animal Model

An NZB/W F1 mouse is a lupus animal model showing a voluntary lupus symptom. On the animal model, the effect of 2,4-pyrimidine derivatives was tested.

Each group included 10, 25-week aged male NZB/W F1 mice. Each group was intraperiotneally administered with a control (5% DMSO solution) or a testing agent (2,4-pyrimidine derivative in a dose of 30 mg/kg) once a day. Except for mice which died by worsening of lupus symptoms, the ratio of surviving mice was analyzed.

9. Statistical Analysis

The student's t-test was used for statistical analysis. P values of <0.05 were considered to represent statistically significant differences.

<Experimantal Results>

Figure 19:
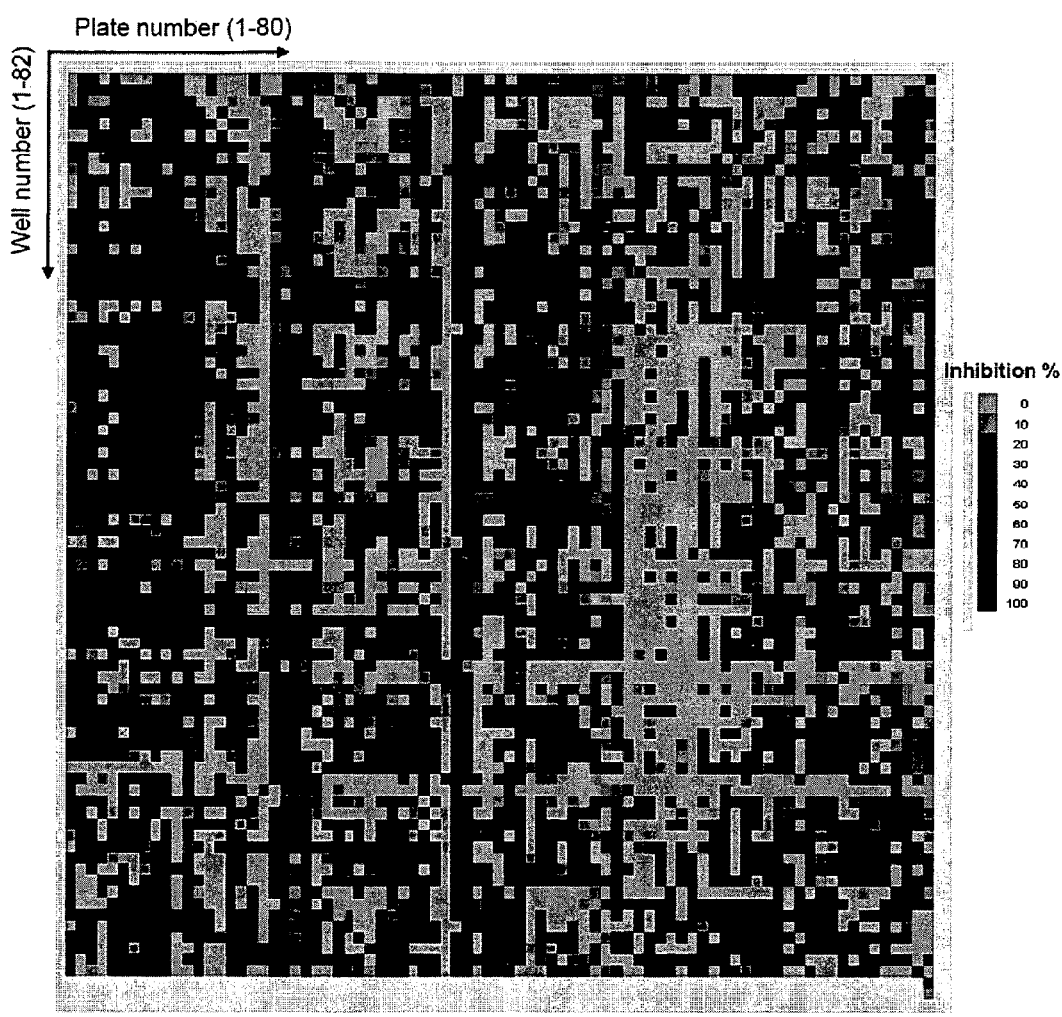
FIG. 19 shows a heat map of preliminary screening data.

To identify chemicals that can affect membrane translocation of gp96, the present inventors employed the interaction of gp96 with AIMP1 as the screening target. For this screening, the present inventors chose 6,482 chemicals with different pharmacophore representing 150,000 different chemicals deposited in Korea Chemical Bank and identified the compounds that can inhibit the interaction of the two proteins. For the screening, the present inventors set up a modified ELISA method using recombinant AIMP1 and gp96 proteins as described in Experimental methods. Each of the tested compounds gave different effect on the interaction of the two proteins (FIG. 19). And the present inventors have selected 12 compounds that inhibited the interaction more than 95% of the control at 0.1 μM (Table 1). The present inventors obtained 1251 additional compounds derived from these 12 initial hits and tested them again for their activities against the gp96-AIMP1 interaction. Among them, 77 compounds showed inhibiting effect while 1174 compounds gave no effect (Table 1).

TABLE 1

| Primary hits ID | derivatives | Effect on gp96-AIMP1 interaction | | Effect on cell surface gp96 levels | | |
|---|---|---|---|---|---|---|
| | | inhibition | no effect | increase | decrease | no effect |
| 16850 | 160 | 14 | 146 | 1 | 2 | 11 |
| 7529 | 160 | 17 | 143 | 3 | 3 | 11 |
| 89456 | 80 | 7 | 73 | 4 | 1 | 2 |
| 100979 | 80 | 4 | 76 | 1 | 0 | 3 |
| 45884 | 80 | 4 | 76 | 0 | 0 | 4 |
| 39410 | 241 | 20 | 221 | 2 | 0 | 18 |
| 97982 | 80 | 8 | 72 | 1 | 0 | 7 |
| 46373 | 80 | 3 | 77 | 0 | 2 | 1 |
| 16810 | 80 | 0 | 80 | — | — | — |
| 46014 | 19 | 0 | 19 | — | — | — |
| 45881 | 160 | 0 | 160 | — | — | — |
| 41847 | 32 | 0 | 32 | — | — | — |
| Total number | 1251 | 77 | 1174 | 12 | 8 | 57 |

In the Table 1, the term "primary hits ID" means ID of compound library, and the term "derivatives" represent derivatives related to the ID. The term "effect on gp96-

AIMP1 interaction" refers to inhibition activity of the derivatives or no effect thereof, and the term "effect on cell surface gp96 levels" represents results of the derivatives showing inhibition activity.

Figure 20:
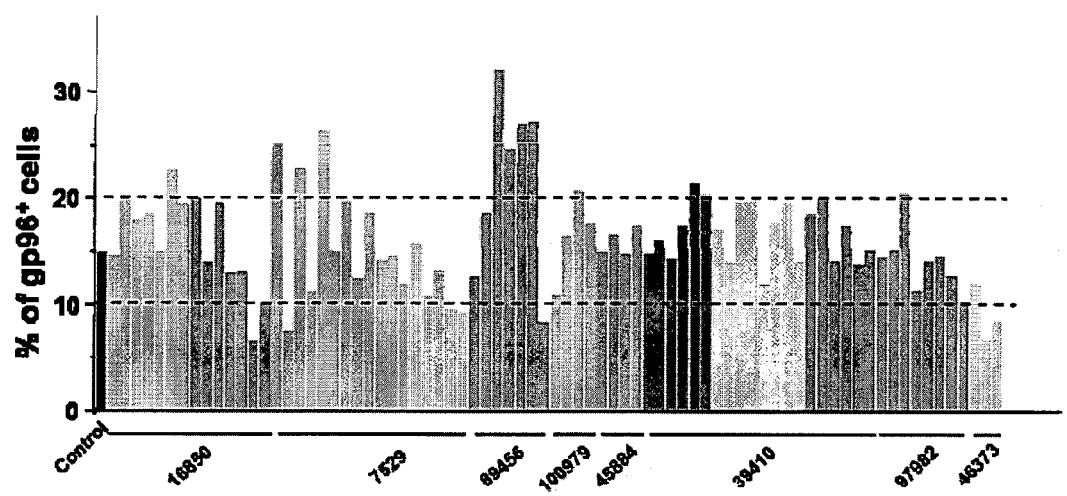
FIG. 20 shows an effect of a derivative on gp96 surface expression in a preliminary test selection group.
Figure 21:
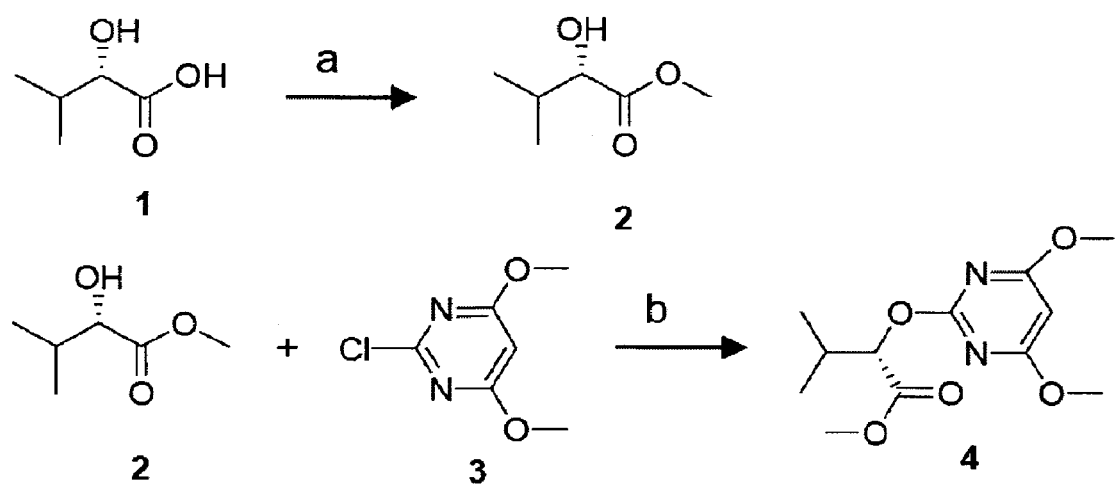
FIG. 21 shows a synthesis of GPM1, (S)-methyl 2-(4,6-dimethoxypyrimidin-2-yloxy)-3-methylbutanoate.

The chemicals that would block the interaction of gp96 and AIMP1 are expected to either enhance or suppress the surface localization of gp96 depending on their binding sites. The present inventors thus examined the effects of the 77 compounds on the surface expression of gp96 as described in Experimental methods. Out of 77 compounds, 8 decreased gp96+ cells below 10% of the whole examined cell population whereas 12 compounds increased gp96+ cells more than 20%, and the rest 57 compounds gave the effects within the range between them (FIG. 20 and Table 1). Among them, only one compound, [(S)-methyl 2-(4,6-dimethoxypyrimidine-2-yloxy)-3-methylbutanoate] (designated as GPM1, FIG. 1a; Teague, S. J., Davis, A. M., Leeson, P. D. & Oprea, T. Angew. Chem. Int. Ed. 38, 3743-3748 (1999)), is selected and synthesized following the procedure shown in FIG. 21, and compounds having pyrimidine backbone is selected as its derivative. Among the tested chemicals, numerous compounds contained 4,6-dimethoxypyrimidine backbone although they showed different suppressive effect on the surface expression of gp96 level (Table 2), suggesting that this backbone may be important for the activity.

TABLE 2

| Compound | Inhibition rate (at 100 nM; %) |
|---|---|
| Formula 2 | 95 |
| Formula 3 | 97 |
| Formula 4 | 94 |
| Formula 5 | 82 |
| Formula 6 | 71 |
| Formula 7 | 99 |
| Formula 8 | 30 |
| Formula 9 | 90 |
| Formula 10 | 76 |
| Formula 11 | 95 |
| Formula 12 | 86 |
| Formula 13 | 86 |
| Formula 14 | 84 |
| Formula 15 | 54 |

In the meantime, 2-(4,6-dimethoxypyrimidin-2-yloxy)-3-phenylpropanoic acid represented by Formula 16 showed only 4% inhibition on the interaction of gp96 and AIMP1, implying that the chemical moiety attached to 4,6-dimethoxypyrimidine backbone is also important. The present inventors thus used it as a negative control (NC1) (FIG. 1 lower).

Figure 2:
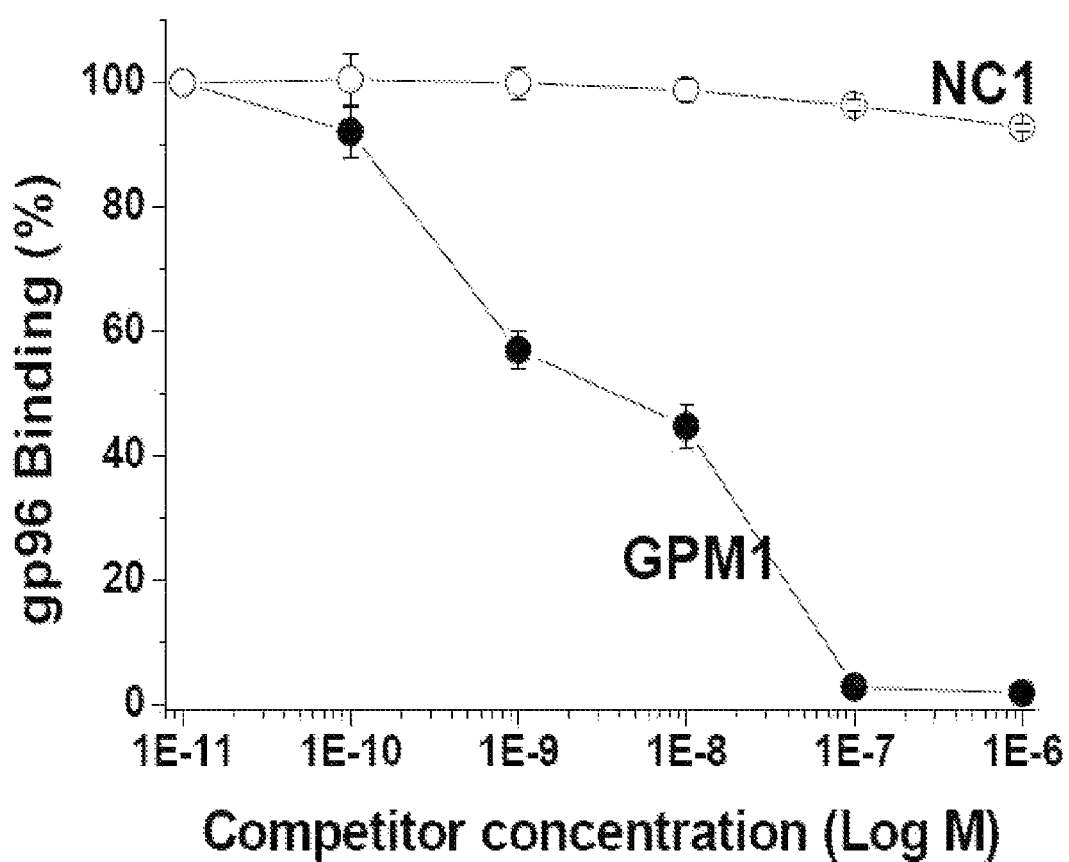
Figure 3:
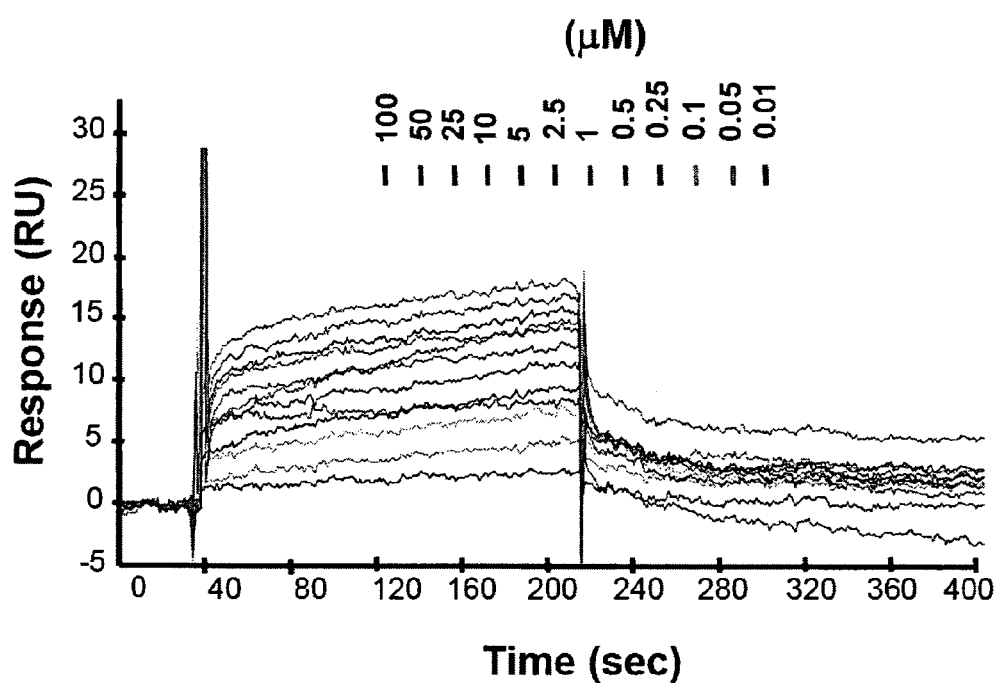
Figure 22:
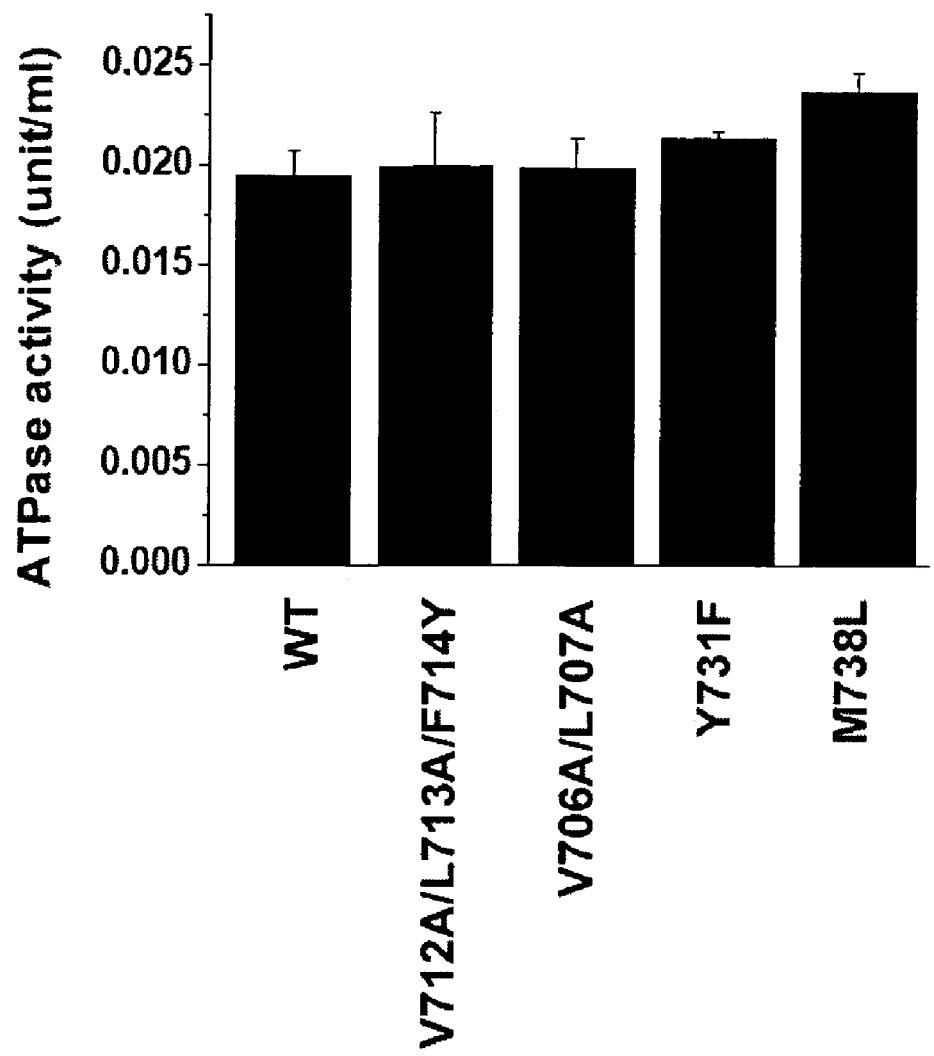
FIG. 22 shows an effect of point mutation on ATPase activity of gp96.

The present inventors compared the dose-dependent effect of GPM1 and NC1 on the interaction of gp96 and AIMP1 using ELISA. GPM1 showed 50% inhibition at around 30 nM whereas NC1 gave no effect (FIG. 2). The present inventors monitored the binding kinetics of GPM1 to gp96 or AIMP1 by surface plasmon resonance (SPR) using BIAcore 3000. GPM1 showed the binding to gp96 with $K_D$ of 87.9 nM (FIG. 3 and Table 3) but no apparent binding to AIMP1, implying its preferential affinity to gp96. To further define the GPM1 binding region of gp96 (Han, J. M., Park, S. G., Liu, B., Park, B. J., Kim, J. Y., Jin, C. H., Song, Y. W., Li, Z. & Kim, S. Am. J. Pathol. 170, 2042-2054 (2007)), the present inventors introduced point mutations at L707, V706, V712, L713, F714, Y731 and M738 that are located within AIMP1 binding region of gp96 and monitored how the mutations at these sites would affect the binding of GPM1 to gp96 using SPR method. Except for V706A/L707A mutant, all the mutants showed decreased affinity to GPM1 to different degree (Table 3) although they retained the normal ATPase activity of gp96 (FIG. 22), suggesting that the C-terminal region of gp96 should be involved in the interaction with GPM1.

TABLE 3

| | gp96 | | |
|---|---|---|---|
| | $K_a$ (M$^{-1}$s$^{-1}$) | $K_d$ (s$^{-1}$) | $K_D$ (nM) |
| WT | $1.75 \times 10^5$ | 0.0154 | 87.9 |
| Y731F | $2.04 \times 10^4$ | 0.0149 | 730 |
| M738L | $6.3 \times 10^4$ | 0.0132 | 210 |
| V712A/L713A/F714Y | 650 | 0.0142 | 21900 |
| V706A/L707A | $1.15 \times 10^5$ | 0.0102 | 88.6 |

Figure 4:
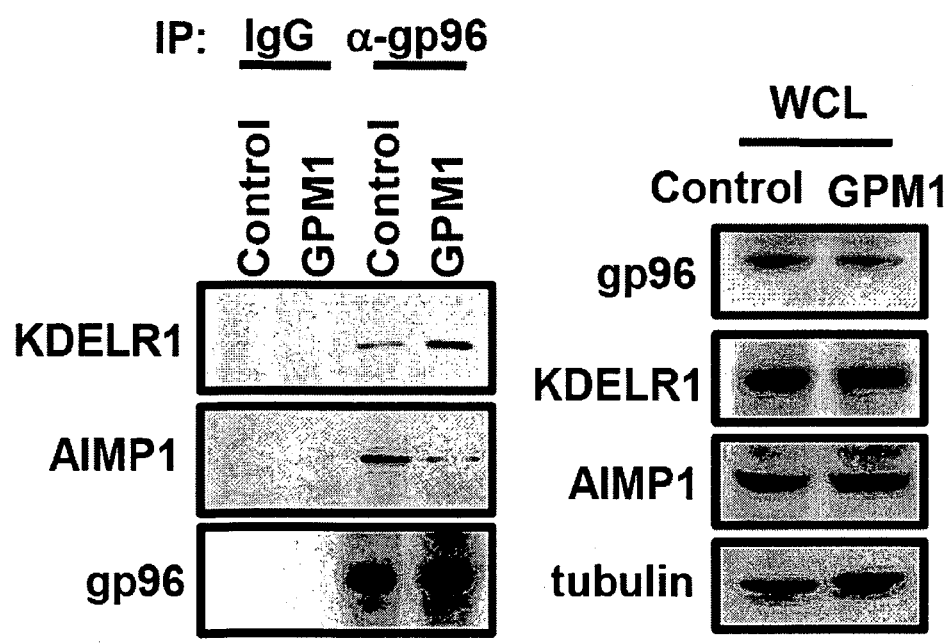
Figure 5:
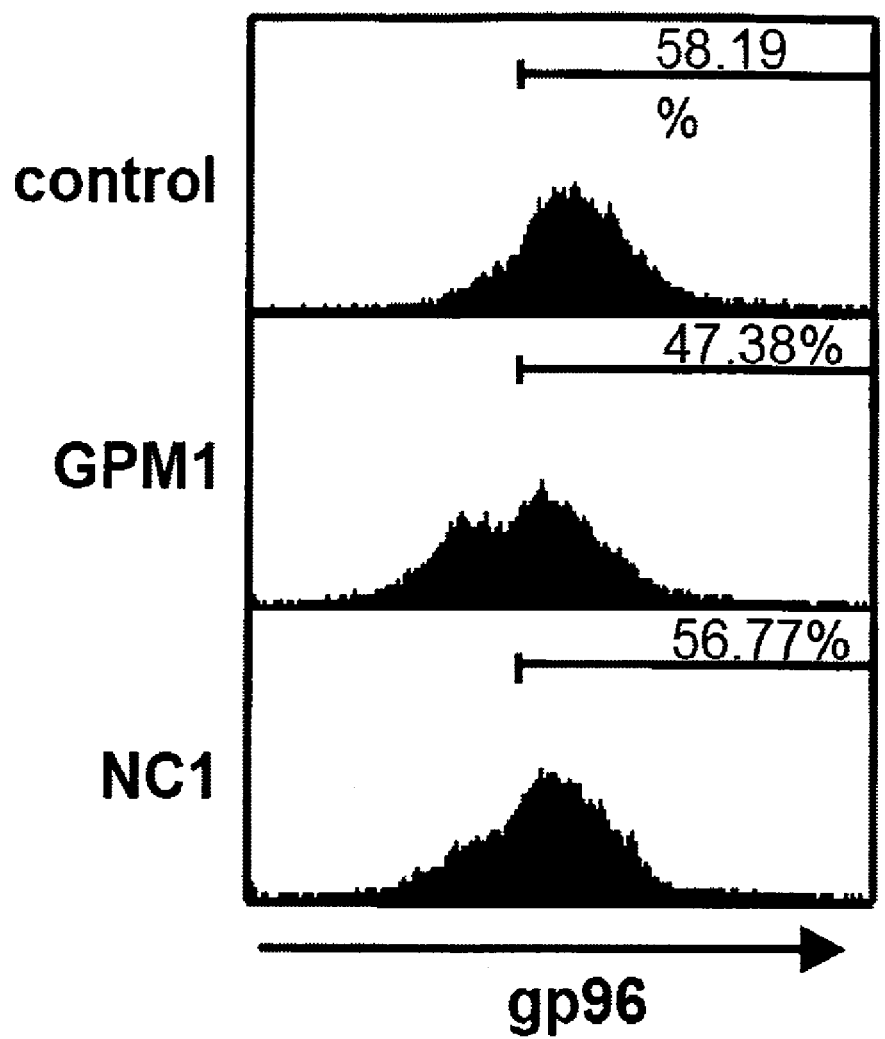
Figure 6:
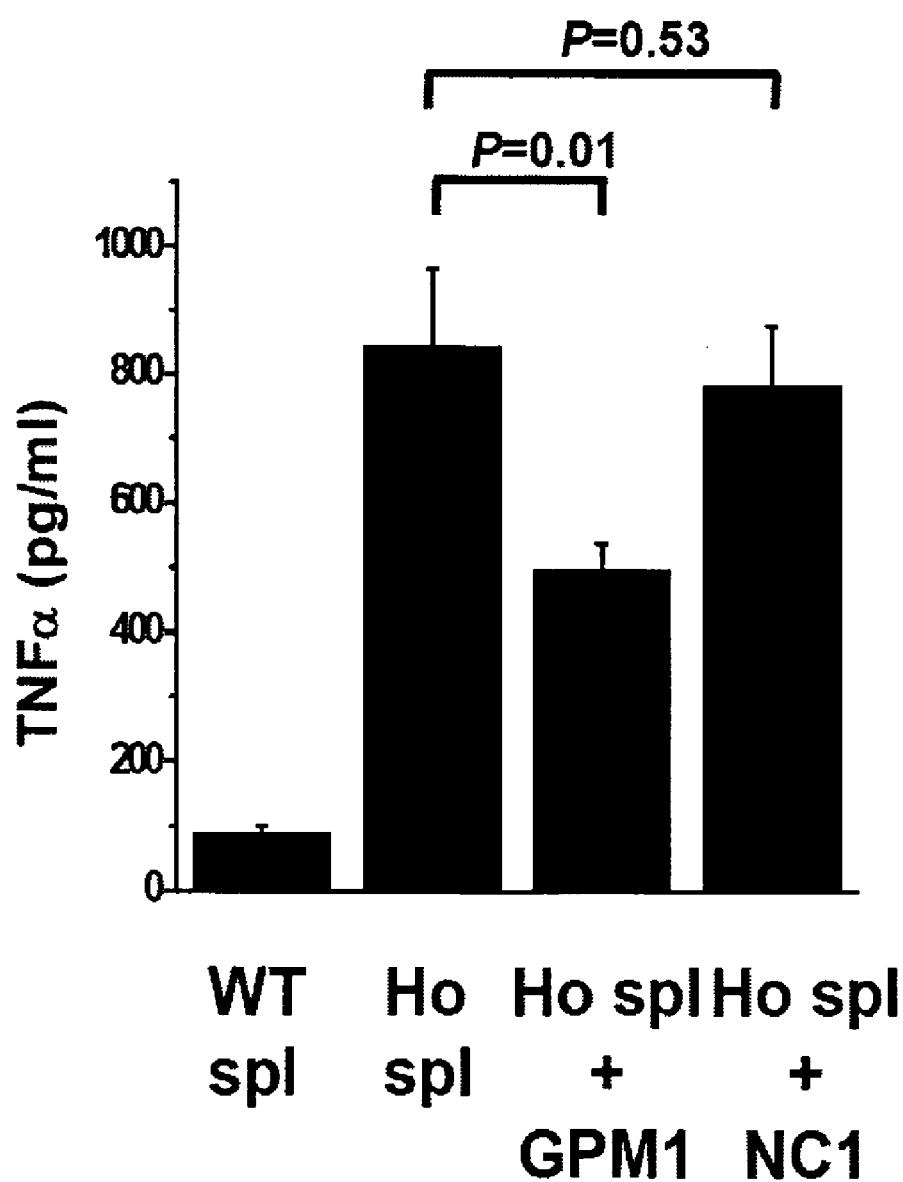
Figure 23:
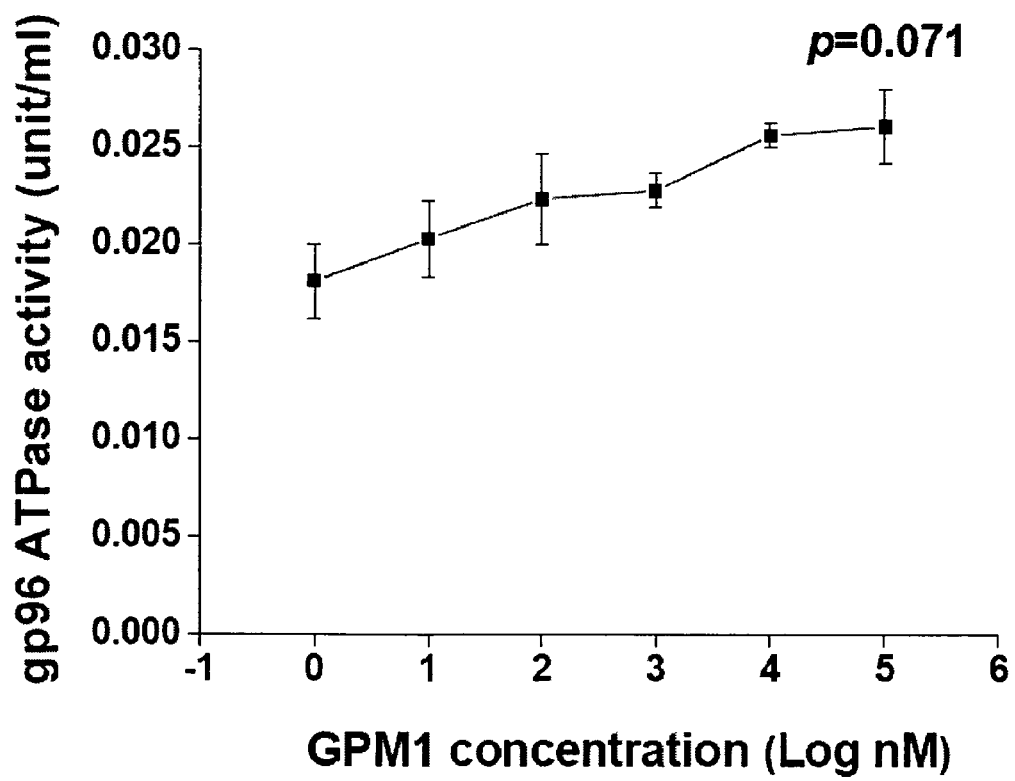
FIG. 23 shows an effect of GPM1 on ATPase activity of gp96.

AIMP1 suppresses surface translocation of gp96 by facilitating the interaction of gp96 with KDEL receptor-1 (KDELR1) that retrieves KDEL motif-containing proteins like gp96 from Golgi to ER21 (Semenza, J. C., Hardwick, K. G., Dean, N. & Pelham, H. R. Cell 61, 1349-57 (1990)). To see whether GPM1 can functionally mimic AIMP1 in this regard, the present inventors examined how GPM1 influences the interaction of gp96 with KDELR1 as well as with AIMP1 by co-immunoprecipitation of these proteins in the presence and absence of GPM1. The interaction of gp96 with KDELR1 was increased while its interaction with AIMP1 was decreased by the addition of GPM1 (FIG. 4 left). On the same condition, GPM1 did not affect the cellular levels of gp96, KDER1 and AIMP1 (FIG. 4 right) and the ATPase activity of gp96 (FIG. 23). GPM1, but not NC1, also decreased the surface gp96 of mouse splenocytes (FIG. 5). The increased surface expression of gp96 is also reflected by the stimulatory effect on the maturation of DCs (Han, J. M., Park, S. G., Liu, B., Park, B. J., Kim, J. Y., Jin, C. H., Song, Y. W., Li, Z. & Kim, S. Am. J. Pathol. 170, 2042-2054 (2007)). the present inventors thus performed DC maturation assay in which DCs were cu-cultivated with AIMP1$^{-/-}$ splenocytes that were pretreated with GPM1 or NC1 and the maturation of DCs were monitored by the secreted TNF-α. In this assay, GPM1 significantly reduced the amount of secreted TNF-α compared to NC1 (FIG. 6). Based on these results, GPM1 appears to behave as functional mimicry of AIMP1 in the suppression of surface translocation of gp96 by enhancing the interaction of gp96 with KDELR1 with blocking the interaction of gp96 with AIMP1.

Figure 7:
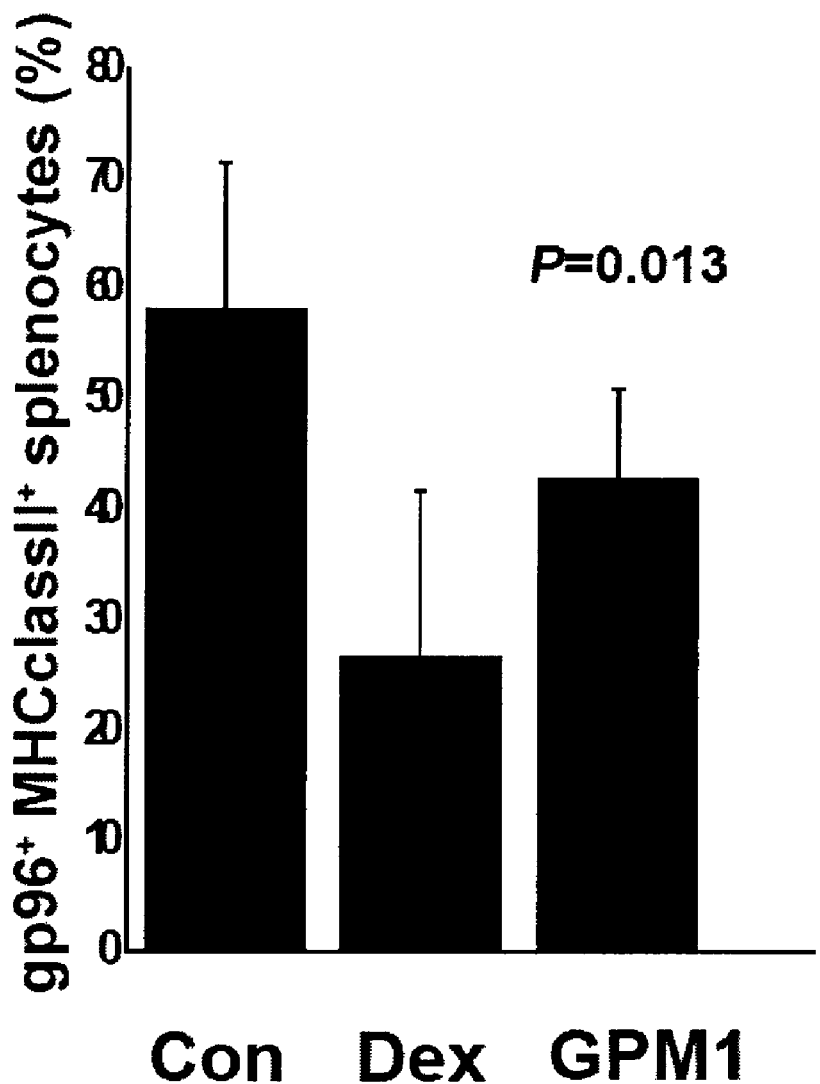
Figure 24:
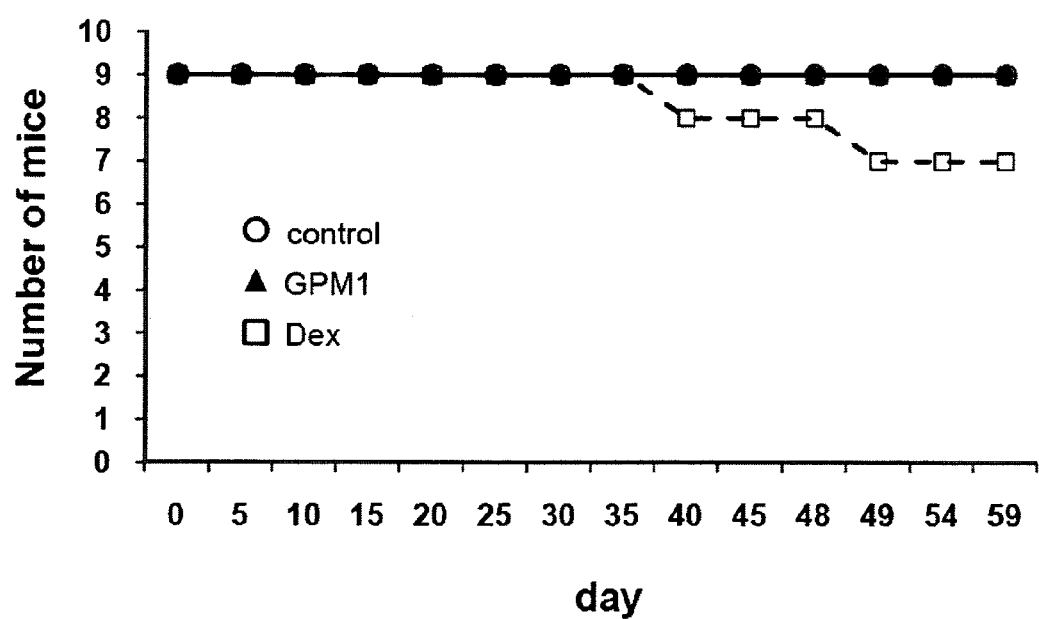
FIG. 24 shows a survival rate of gp96tm transgenic female mice treated with excipient (n=9), GPM1 (n=9) and dexamethasone (n=9) in a dose of 30 mg/kg/day.

The present inventors tested whether GPM1 can also reduce the surface level of gp96 isolated from splenocytes in which the surface levels of gp96 are chronically enhanced in gp96tm transgenic mice. The present inventors compared the effect of GPM1 with phosphate-buffered saline containing 5% DMSO and dexamethasone (Dex), an immunosuppressant of glucocorticoid family as negative and positive control, respectively. Each group consisted of age-matched nine female mice. During the period of 2-month intraperitoneal administration at the dose of 30 mg/kg, GPM1-treated mice did not give apparent adverse effects whereas the two of nine Dex-treated mice died (FIG. 24). After 2 month, the present inventors isolated MHC class II$^+$ splenocytes and lymph nodes from vehicle-, Dex-, and GPM1-treated mice and determined the portion of gp96$^+$ cells by flow cytometry. The percentages of gp96$^+$ MHC class II$^+$ cells in the control, Dex- and GPM1-treated groups were about 57, 25 and 41%, respectively, suggesting the suppressive effect of GPM1 on the surface translocation of gp96 (FIG. 7 and data not shown). GPM1 did not affect the numbers of splenocytes whereas Dex gave significantly negative effect on cell viability (Table 4).

TABLE 4

|  | control | GPM1 | dexamethasone |
|---|---|---|---|
| total cell count (spleen) | $4.18 \pm 2.02 \times 10^6$ | $4.56 \pm 1.44 \times 10^6$ | $4.80 \pm 2.38 \times 10^5$ |

Figure 8:
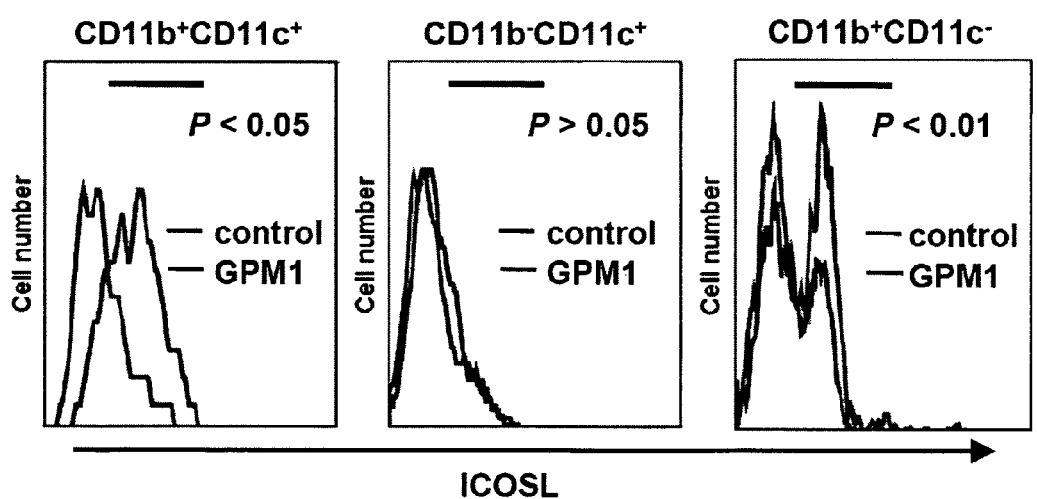
Figure 9:
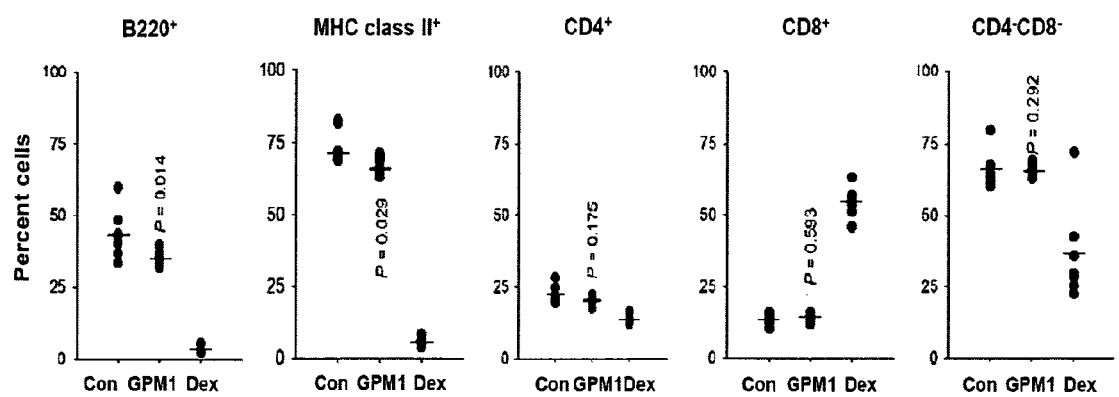
Figure 25:
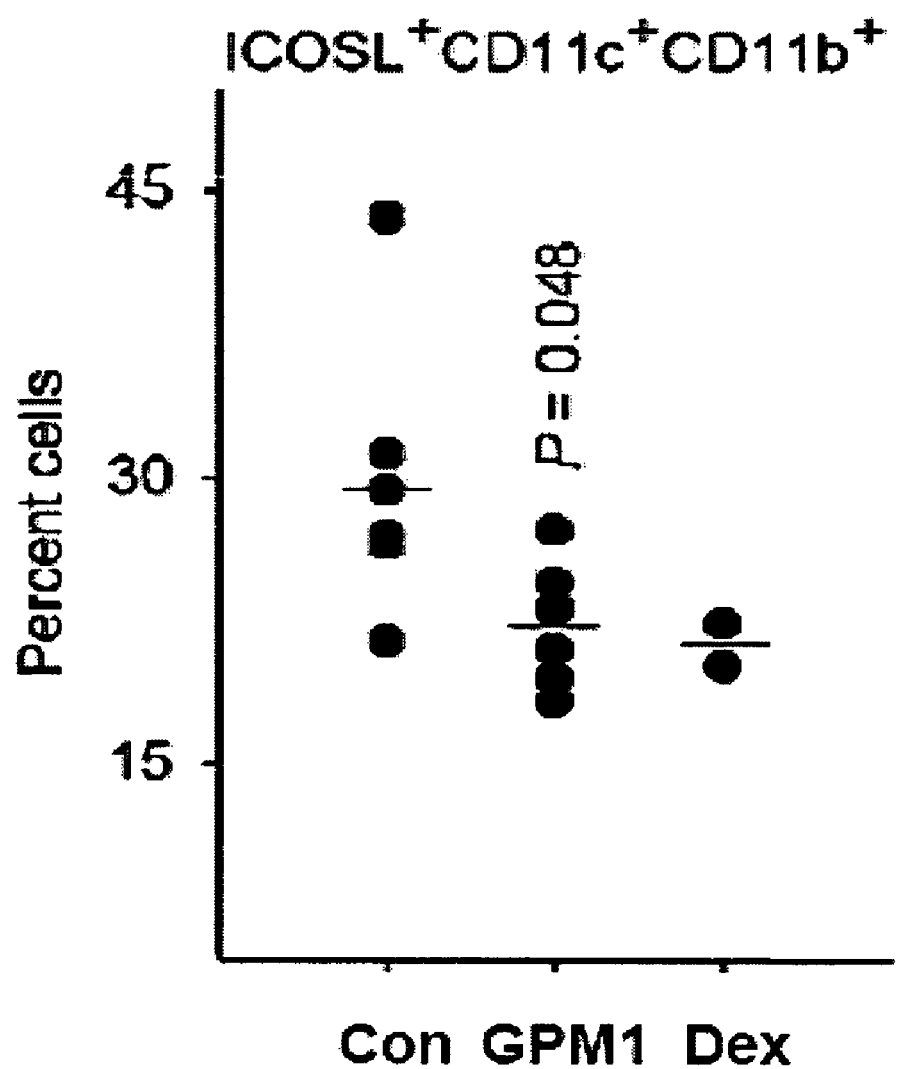
FIGS. 25 to 30 show that inhibition of gp96 on cell surface by GPM1 causes a reduction in maturing of lymph node dendritic cells (DC), and B220$^+$ and MHC class II$^+$ cells, memory T cells and active T cells in gp96tm transgenic mice. P values of student t-test are shown, by which GPM1-treated mice are compared to control mice.
Figure 26:
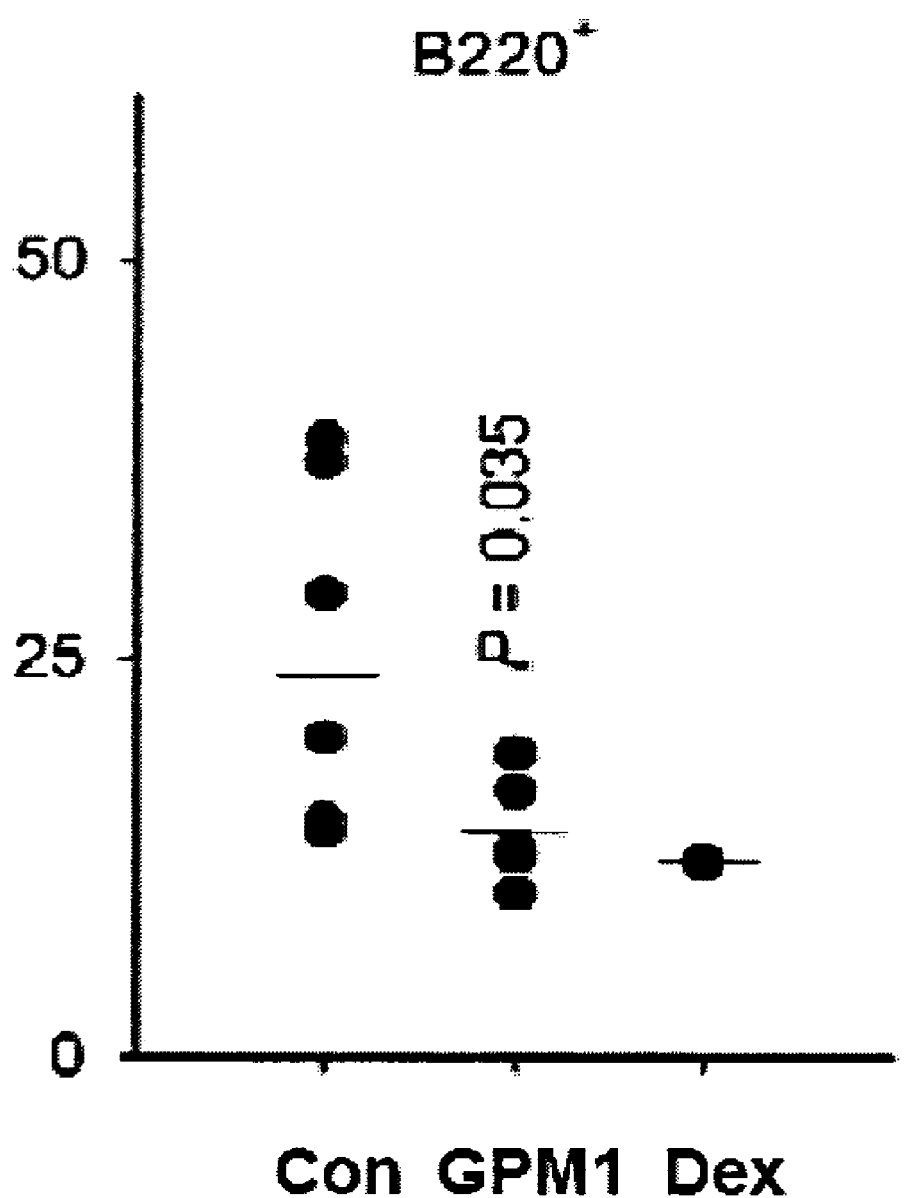
Figure 27:
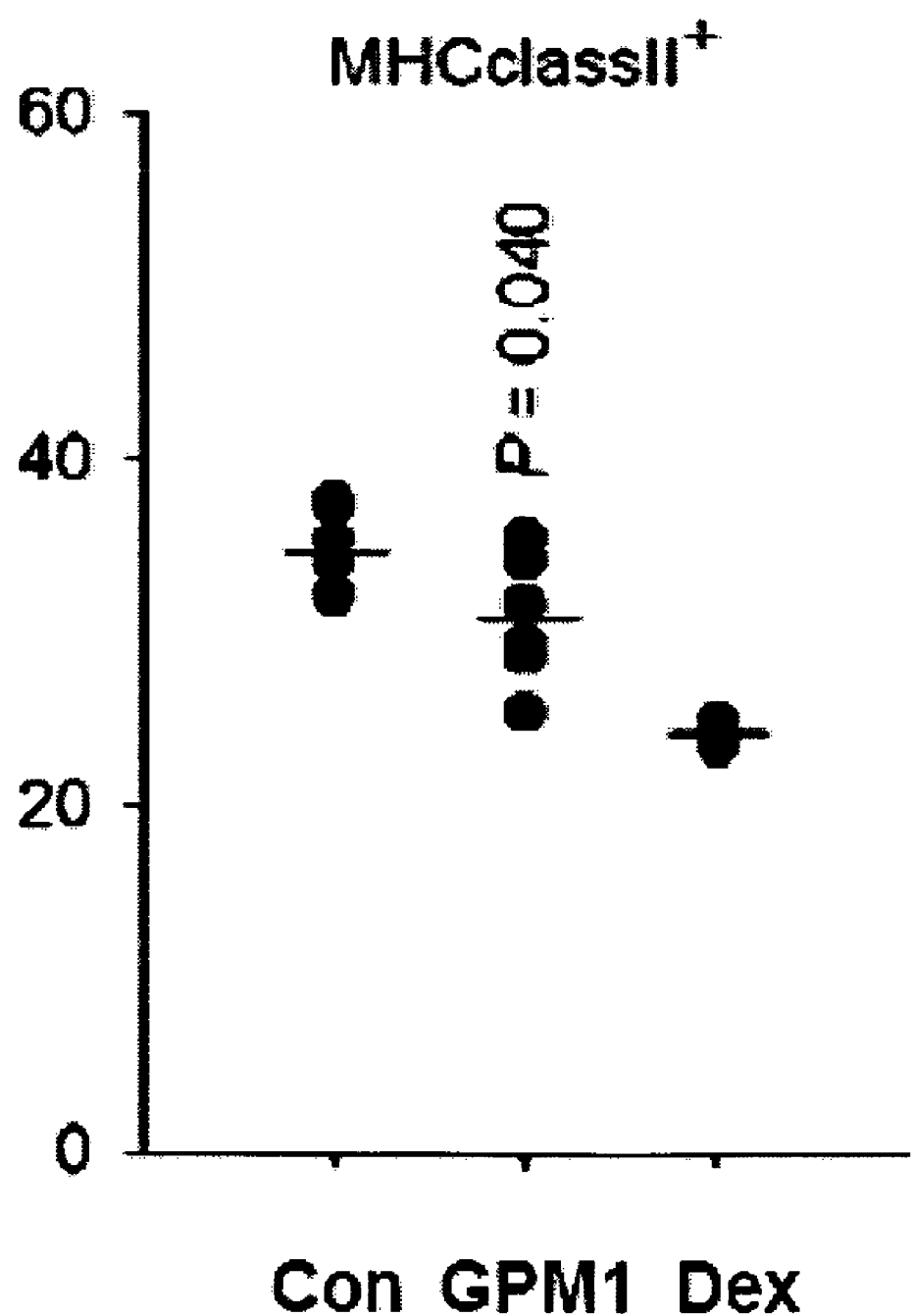
Figure 28:
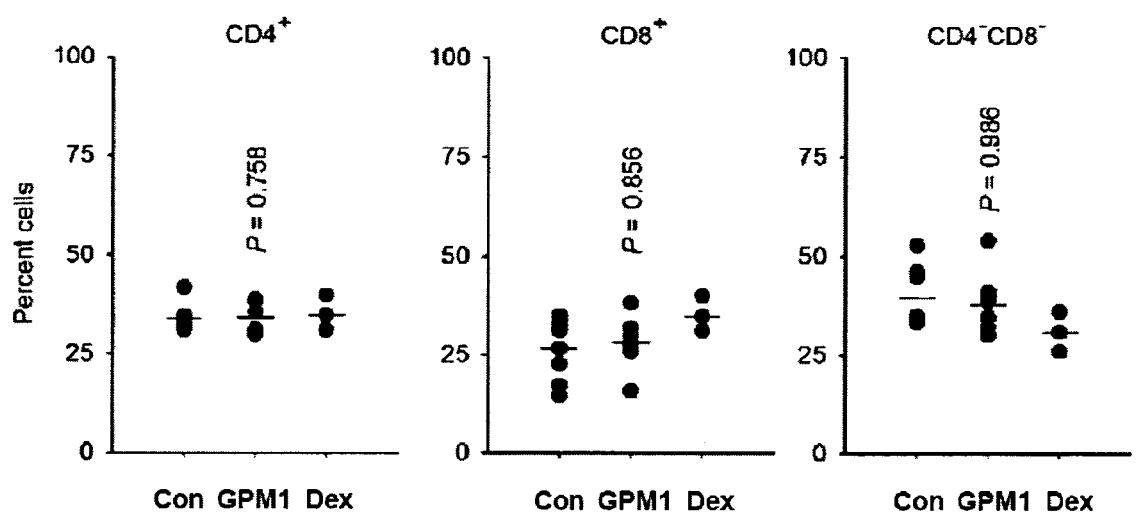

The present inventors then monitored the maturity of DCs by measuring the surface levels of ICOSL, one of the known DC maturation markers using flow cytometry and found that ICOSL levels were significantly reduced in $CD11b^+CD11c^+$ myeloid DC (FIG. 8 left). The present inventors also observed consistent results in lymph nodes (FIG. 25). GMP1-treated mice showed little difference in ICOSL levels in $CD11b^-CD11c^+$ lymphoid DCs (FIG. 8 middle), perhaps because enhanced level of surface gp96 did not affect ICOSL levels in these cells. However, GPM1 also suppressed ICOSL levels in $CD11b^+CD11c''$ macrophages (FIG. 8 right), not affecting the population of these cells (data not shown). GPM1 reduced the $B220^+$ population and MHC class $II^+$ population in the spleen (FIG. 9) and in the lymph nodes (FIGS. 26 and 27).

Figure 35:
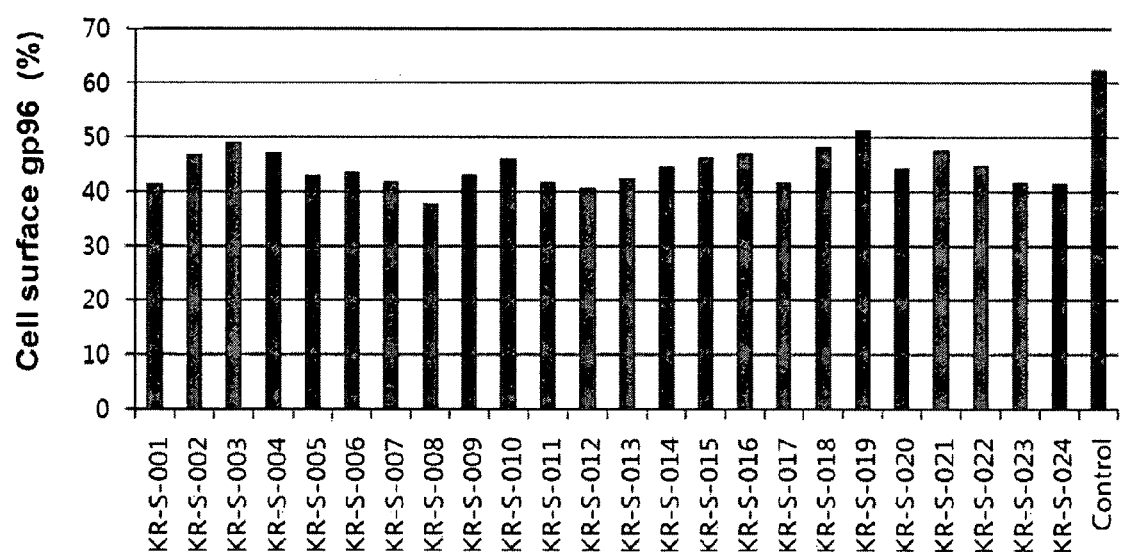
FIG. 35 is a graph showing an FACS analysis result using gp96 antibody, on the amount of gp96 protein existing on a cell surface, when HL-60 cell lines were treated with a 2,4-pyrimidine derivative at a concentration of 1 mM for 24 hours.

Also, HL-60 cell lines were treated with a 2,4-pyrimidine derivative at a concentration of 1 mM for 24 hours, and the amount of gp96 protein existing on a cell surface was analyzed through flow cytometry (FACS) using gp96 antibody. A compound of KR-S-015 is (S)-methyl 2-(4,6-dimethoxypyrimidin-2-yloxy)-3-methylbutanoate, and there are 15 kinds of compounds showing better effects than KR-S-015 (KR-S-008, KR-S-012, KR-S-001, KR-S-024, KR-S-023, KR-S-017, KR-S-011, KR-S-007, KR-S-013, KR-S-005, KR-S-009, KR-S-006, KR-S-020, KR-S-014, KR-S-022). It was analyzed that amide-type compounds (KR-S-001, KR-S-005, KR-S-006, KR-S-007, KR-S-008) are better than ester (KR-S-010) or acid (KR-S-009). Meanwhile, it was analyzed that in ester-type compounds, as an intermediate substitute, methyl (KR-S-011, KR-S-012, KR-S-023, KR-S-024) is better than isopropyl (KR-S-009, KR-S-010) (FIG. 35).

Figure 10:
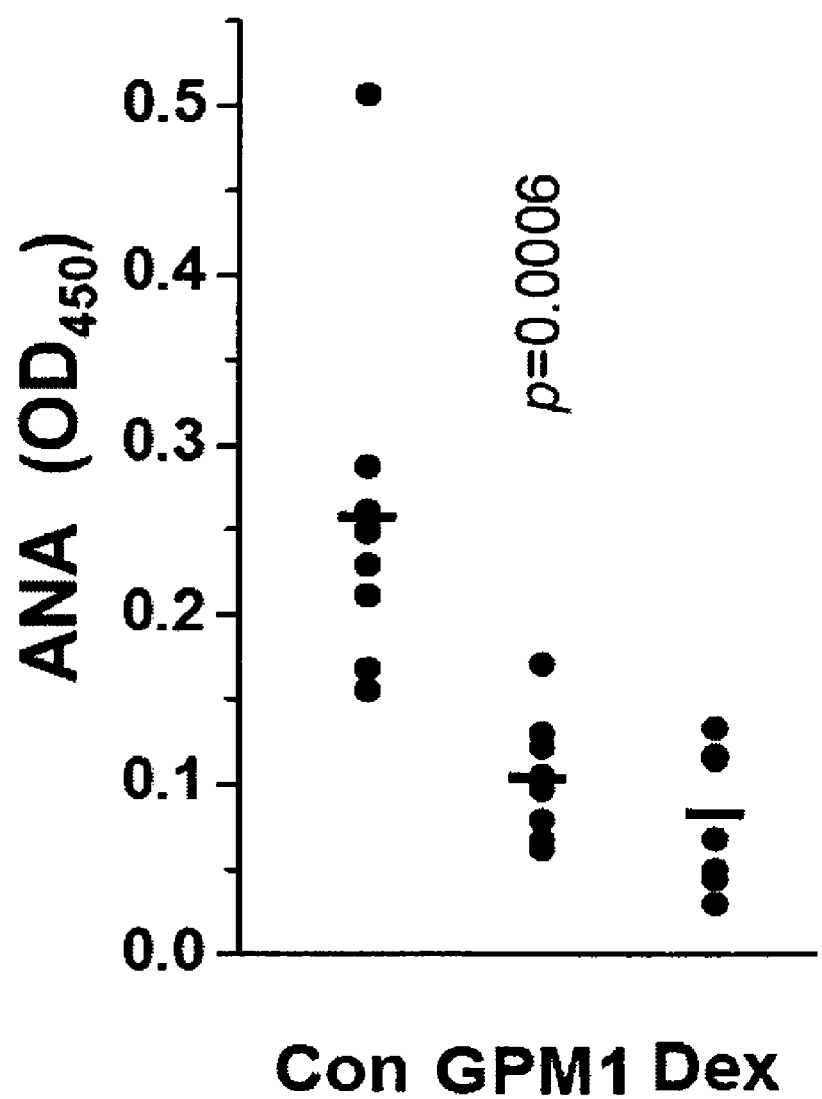
FIGS. 10 to 18 show that inhibition of gp96 on cell surface by GPM1 causes a reduction in a kidney disease, mature B cells, memory T cells and activated T cells in gp96tm transgenic mice. P values of student t-test are shown, by which GPM1-treated mice are compared to control mice.
Figure 11:
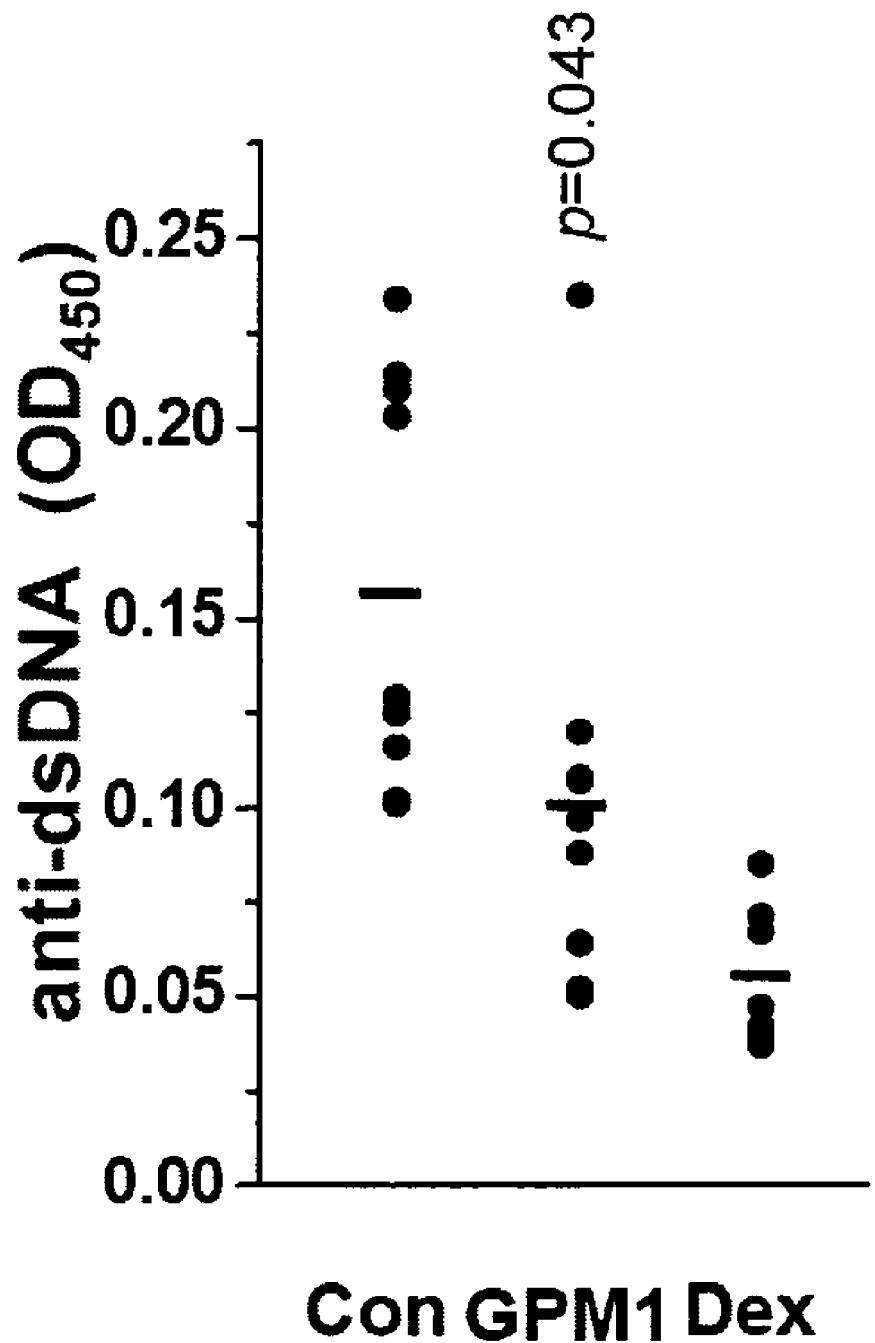
Figure 12:
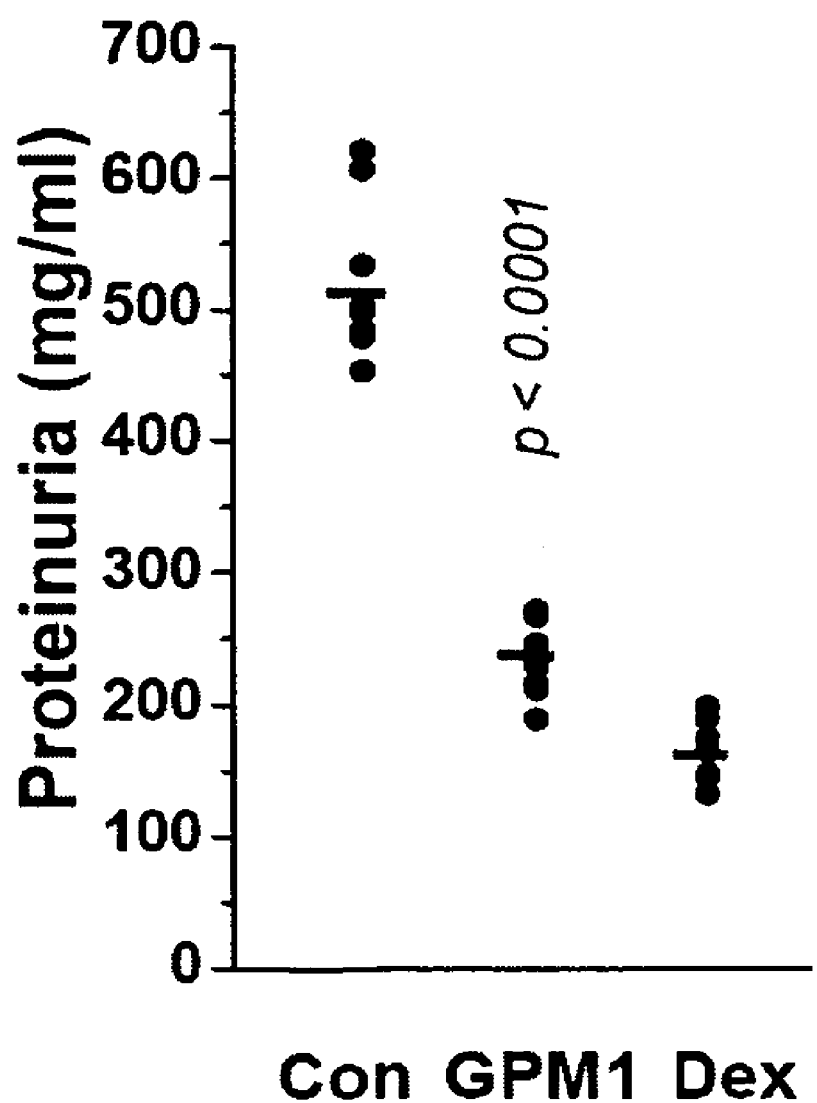
Figure 13:
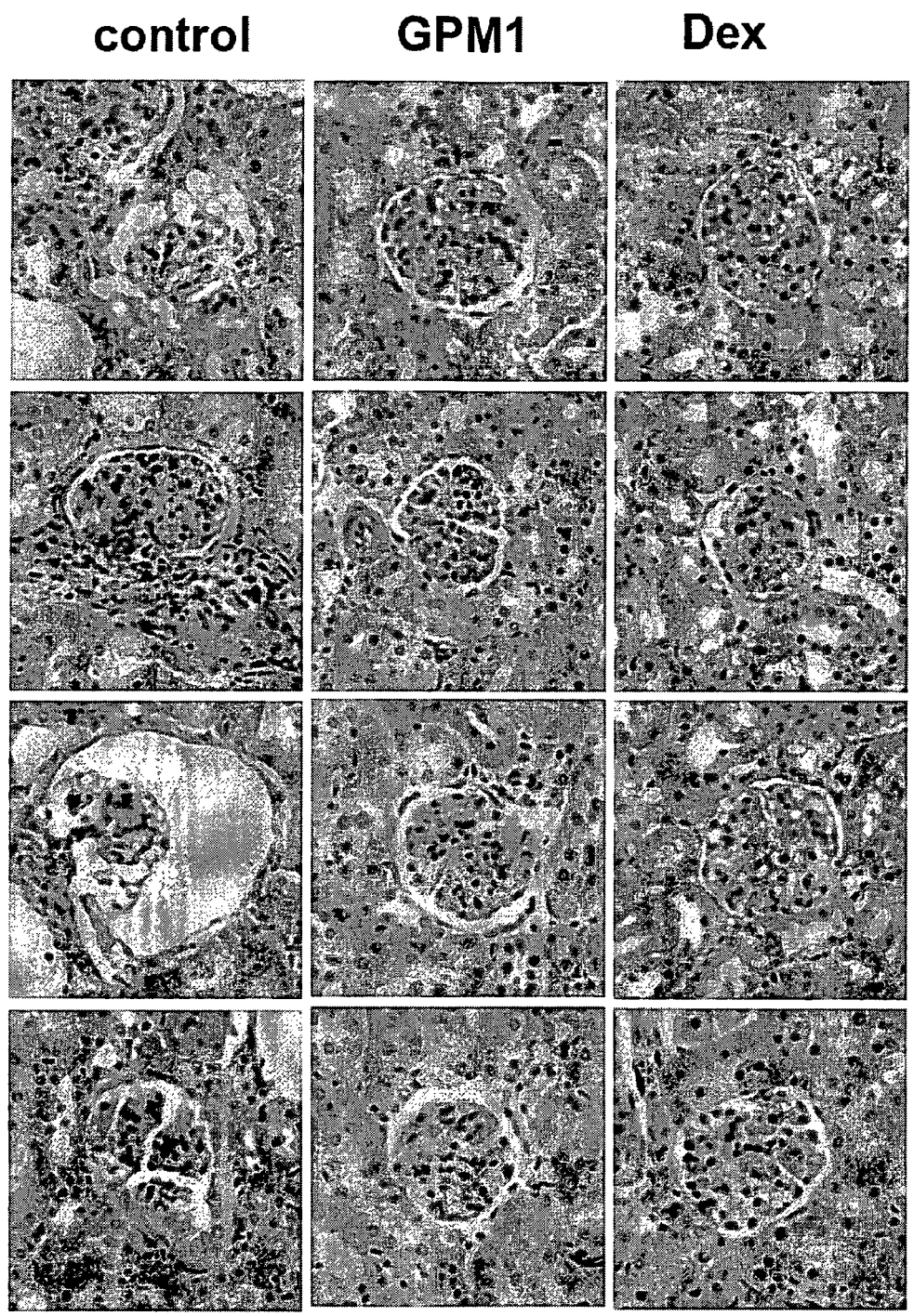
Figure 14:
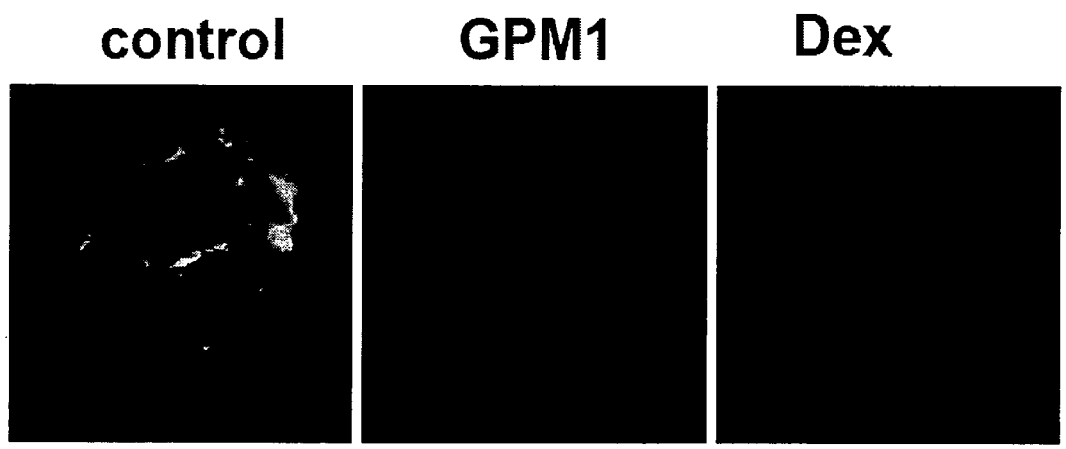

The present inventors then monitored whether lupus-like phenotypes are compromised by systemic administration of GPM1. Nuclear antigen-specific and DNA-specific autoantibody levels were reduced in GPM1-treated mice (FIGS. 10 and 11). Proteinuria, the sign of kidney dysfunction, was also reduced after GPM1 treatment (FIG. 12). Although vehicle-treated mice suffered from glomerulonephritis phenotypes such as basement membrane thickening, severe mesengial proliferation, and abnormal glomerular architecture (FIG. 13 left column) and glomerular immunoglobulin deposition (FIG. 14 left), GPM1 as well as Dex treatment lessened such phenotypes (FIGS. 13 and 14, middle).

Figure 15:
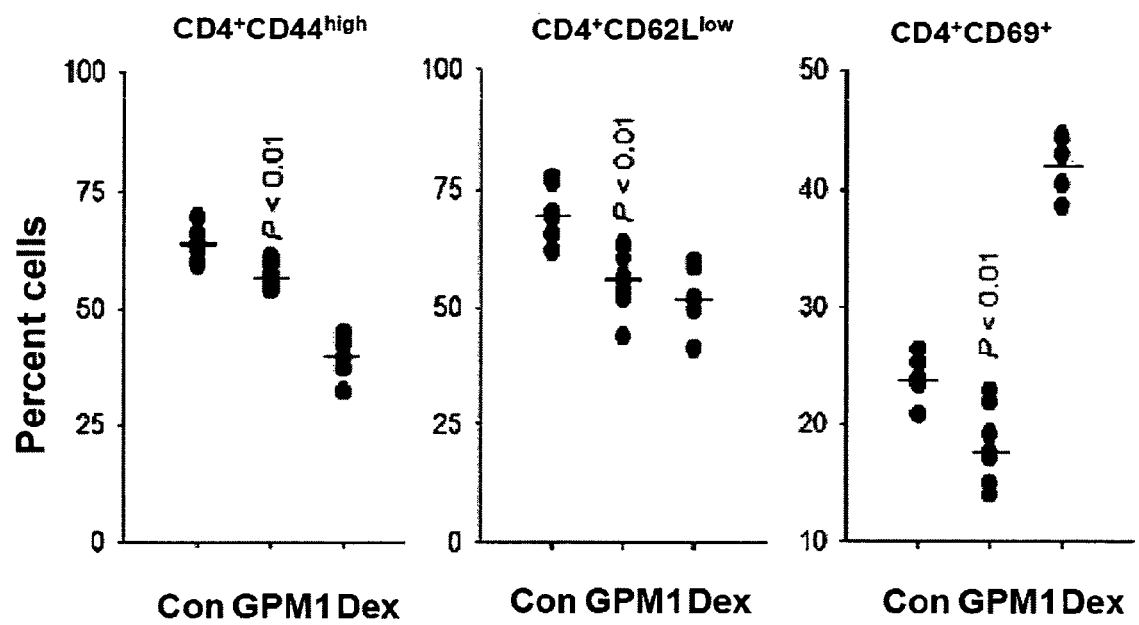
Figure 16:
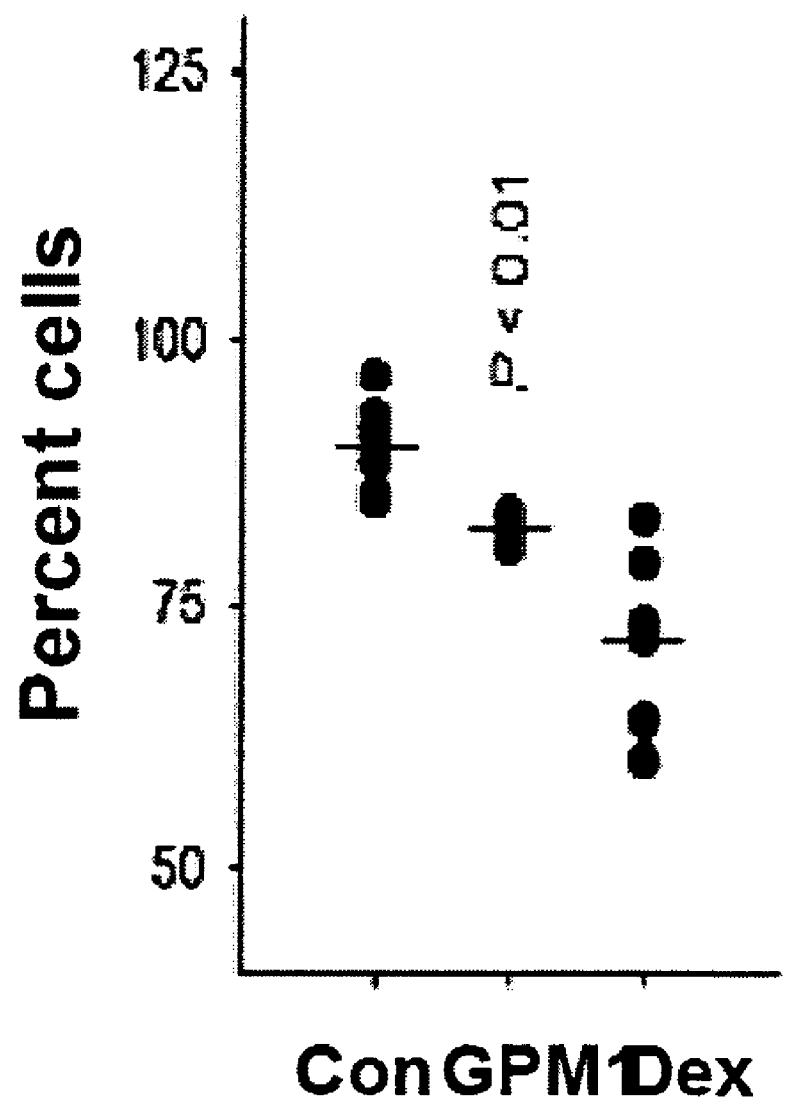
Figure 17:
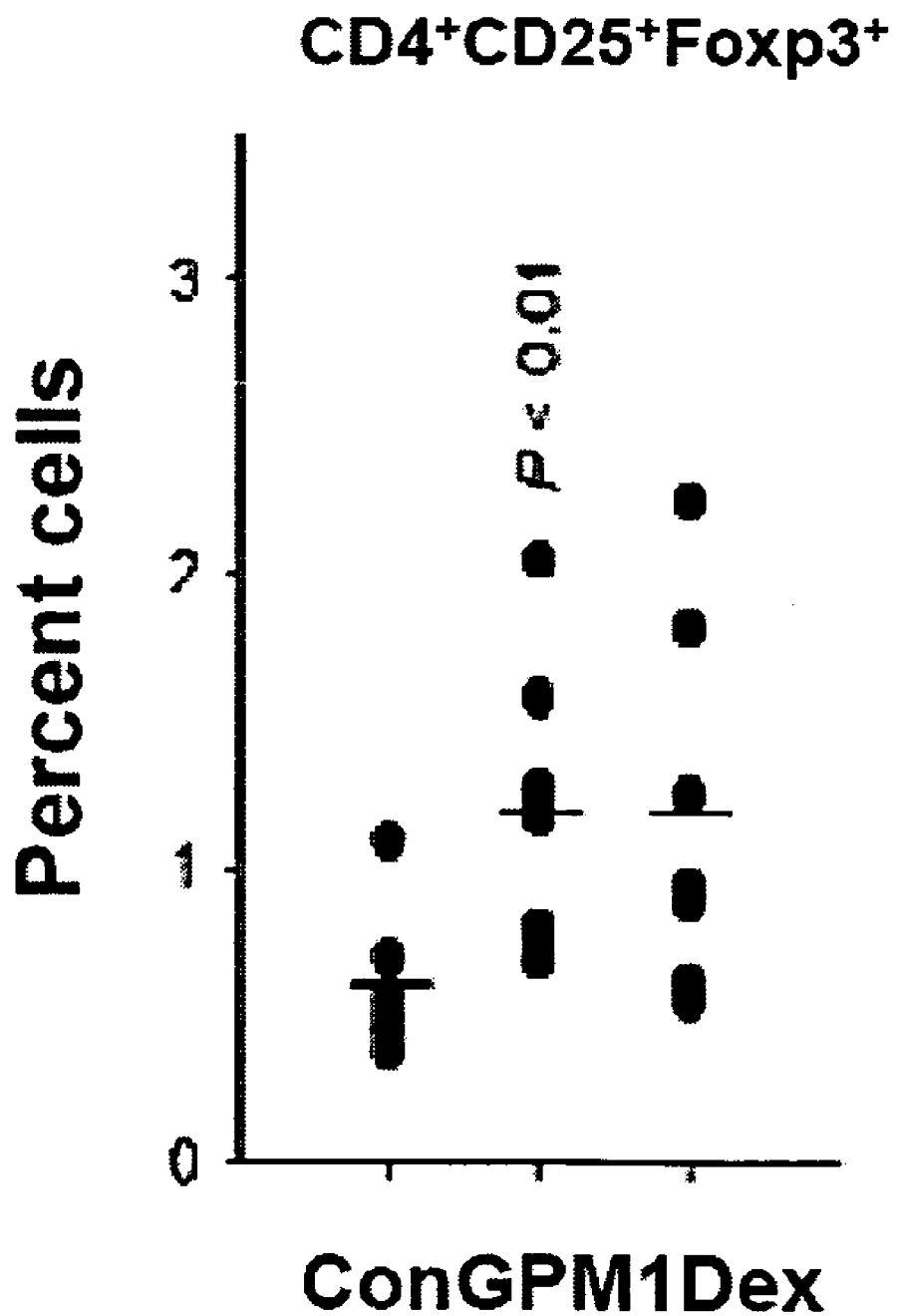
Figure 18:
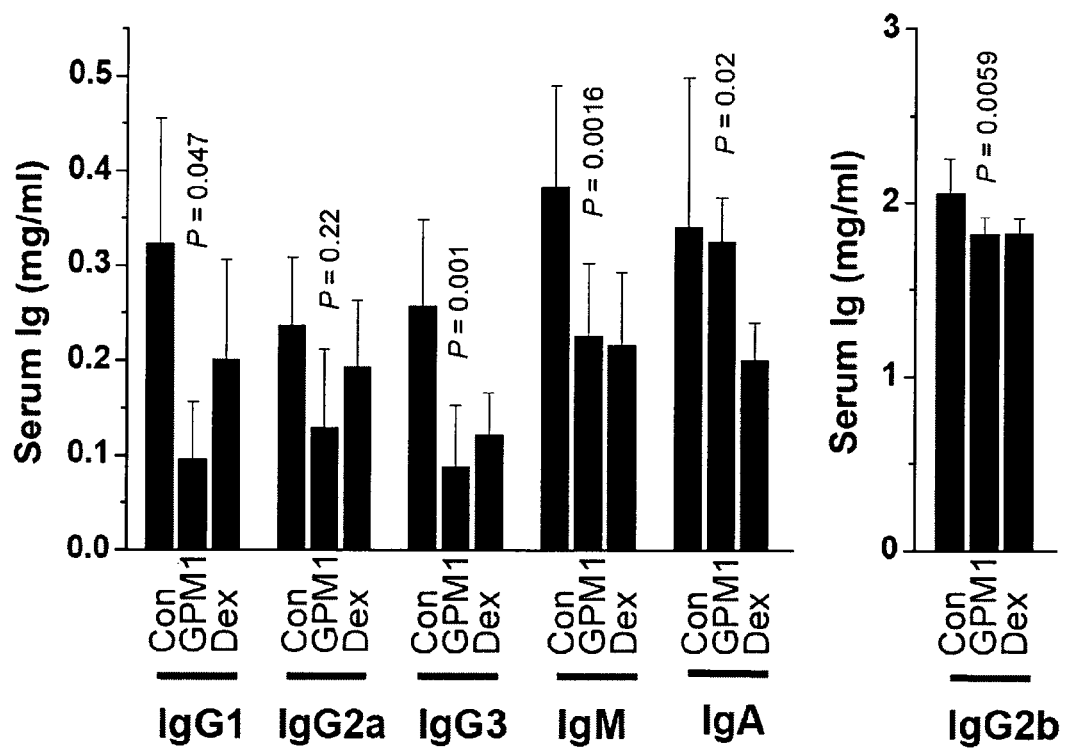
Figure 29:
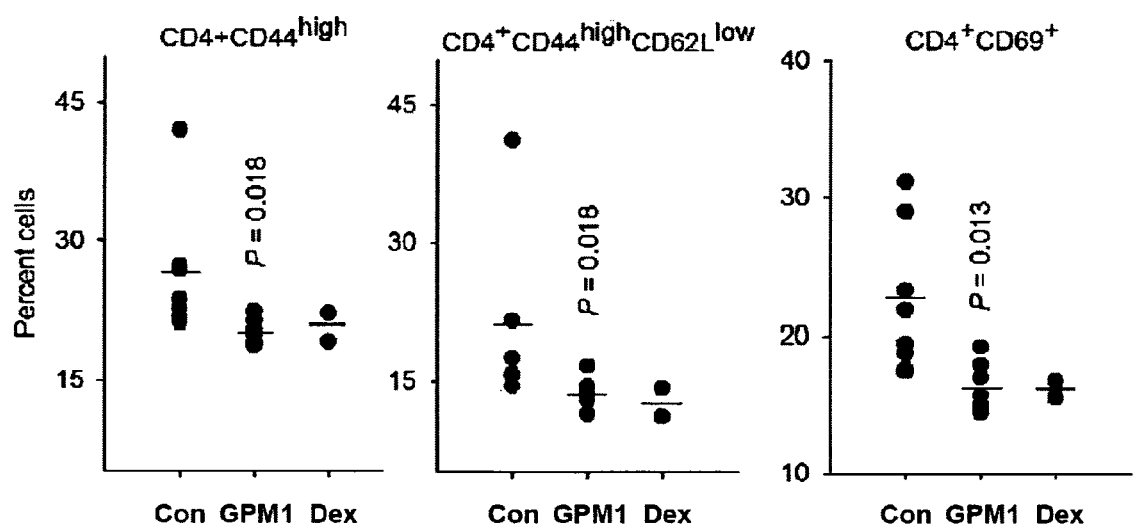
Figure 30:
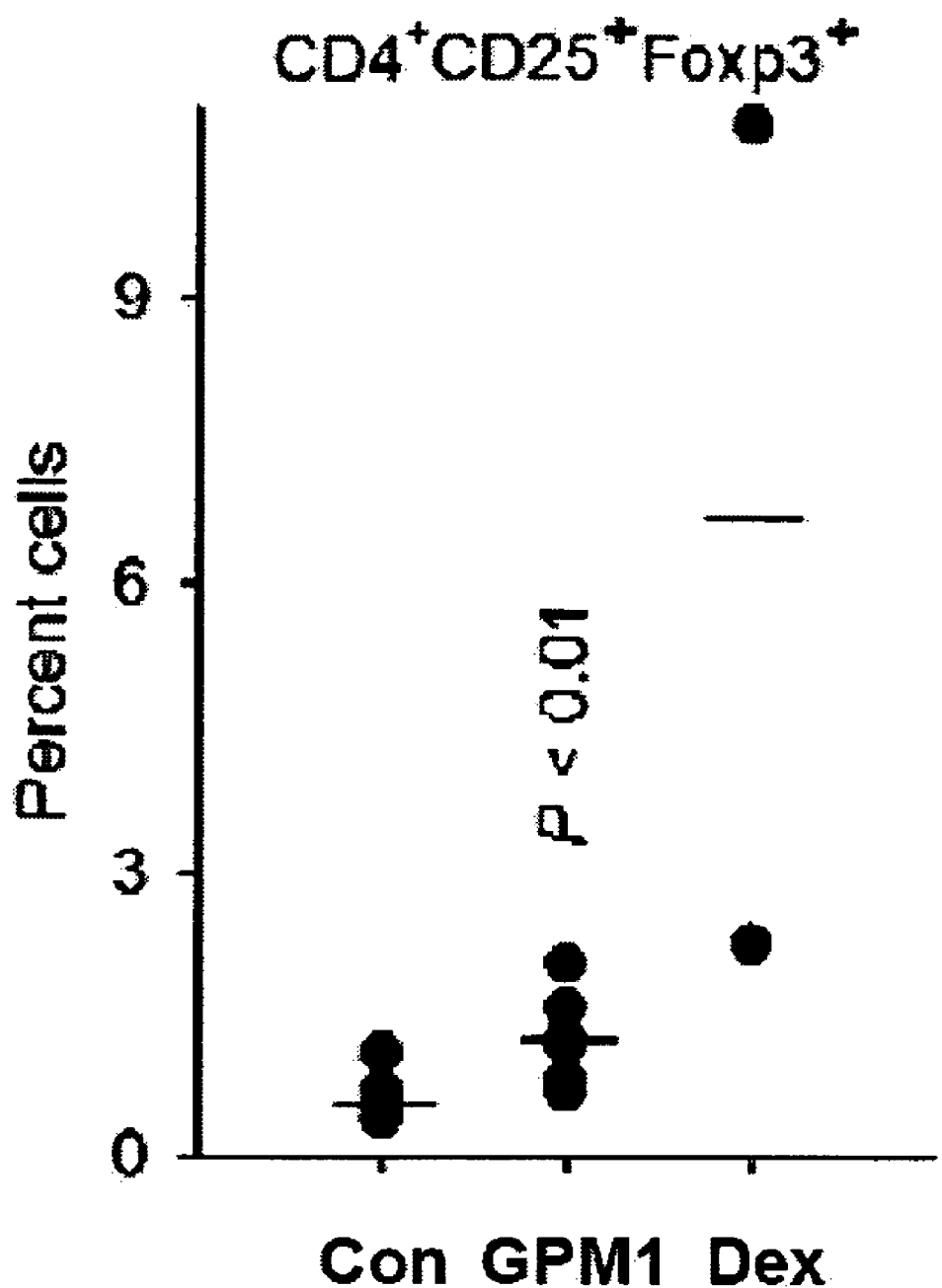

SLE involves abnormal activation of $CD4^+$ T cells that accumulate as activated memory cells and contributes to B cell activation and expansion, and hypergammaglobulinemia (Singer, G. G., Carrera, A. C., Marshak-Rothstein, A., Martinez, C. & Abbas, A. K. Curr. Opin. Immunol. 6, 913-920 (1994); Wakeland, E. K., Wandstrat, A. E., Liu, K. & Morel, L. Curr. Opin. Immunol. 11, 701-707 (1999); Chatham, W. W. & Kimberly, R. P. Lupus 10, 140-147 (2001); Jevnikar, A. M., Grusby, M. J. & Glimcher, L. H. J. Exp. Med. 179, 1137-1143 (1994); Lang, T. J., Nguyen, P., Papadimitriou, J. C. & Via, C. S. J. Immunol. 171, 5795-5801 (2003)). The present inventors found a reduction in the population of $CD4^+$ memory cells and activated $CD4^+$ T cells in the spleen and lymph nodes of GPM1-treated mice ($CD4^+CD44^{high}$, $CD4^+CD62L^{low}$, and $CD4^+CD69^+$ cells; FIGS. 15 and 29). GPM1 treatment also decreased mature B cell population ($B220^+IgM^+IgD^+$; FIG. 2g). The frequency of regulatory T cells, which are instrumental in the maintenance of peripheral immune tolerance and the control of adaptive immune responses, is lower in PBMCs of SLE patients and negatively correlated with SLE-associated phenotypes (Barreto, M., Ferreira, R. C., Lourenco, L., Moraes-Fontes, M. F., Santos, E., Alves, M., Carvalho, C., Martins, B., Andreia, R., Viana, Vasconcelos, C., Mota-Vieira, L., Ferreira, C., Demengeot, J. & Vicente, A. M. BMC Immunol. 10, 5 (2009); La Cava, A. Lupus 17, 421-425 (2008)). The present inventors found an increase of $CD4^+CD25^+$ $Foxp3^+$ regulatory T cell population in the spleen (FIG. 17) and lymph nodes (FIG. 30) of GPM1-treated mice. Gp96tm transgenic mice showed hypergammaglobulinemia. GPM1 treatment reduced total serum levels of IgG1, IgG2b, IgG3, IgM, and IgA (FIG. 18). All of these results consistently suggest that the effect of GPM1 on the molecular interactions and surface translocation of gp96 is also reflected at cellular and in vivo levels.

Figure 31:
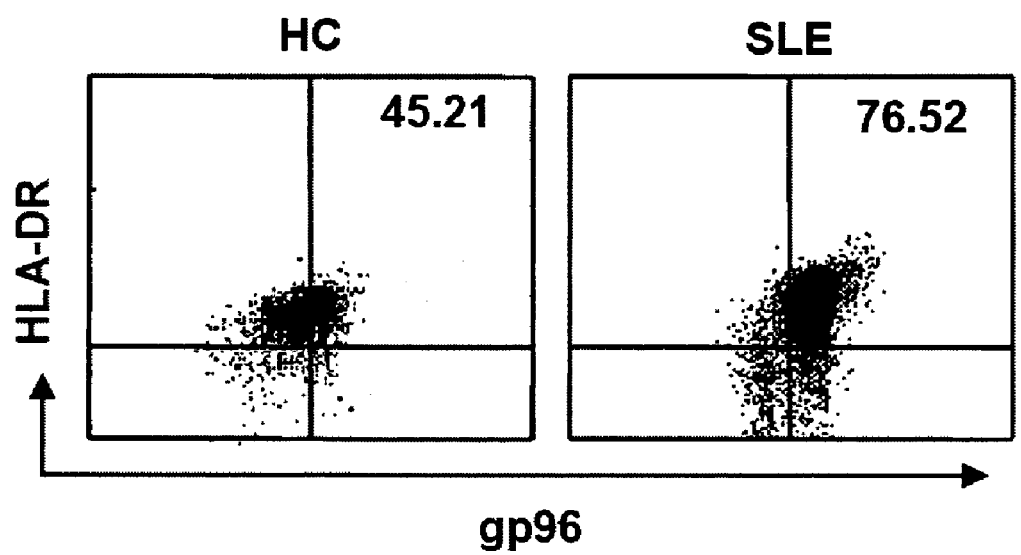
FIGS. 31 to 33 show an increase in cell surface expression of gp96, and a serum level of gp96 antibody, in human SLE patients. P values of student t-test are shown, by which SLE patient group are compared to healthy control group.
Figure 32:
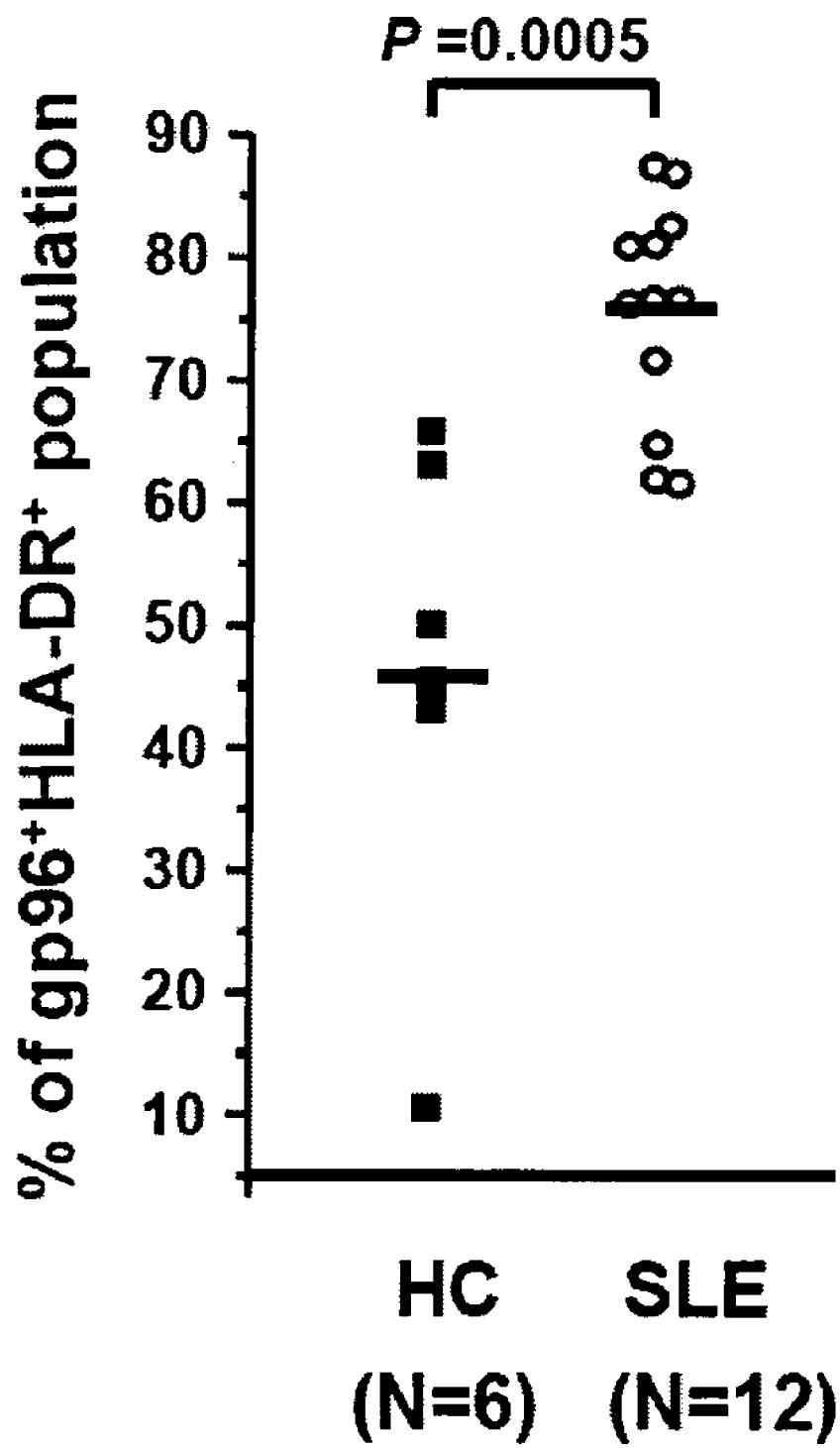
Figure 33:
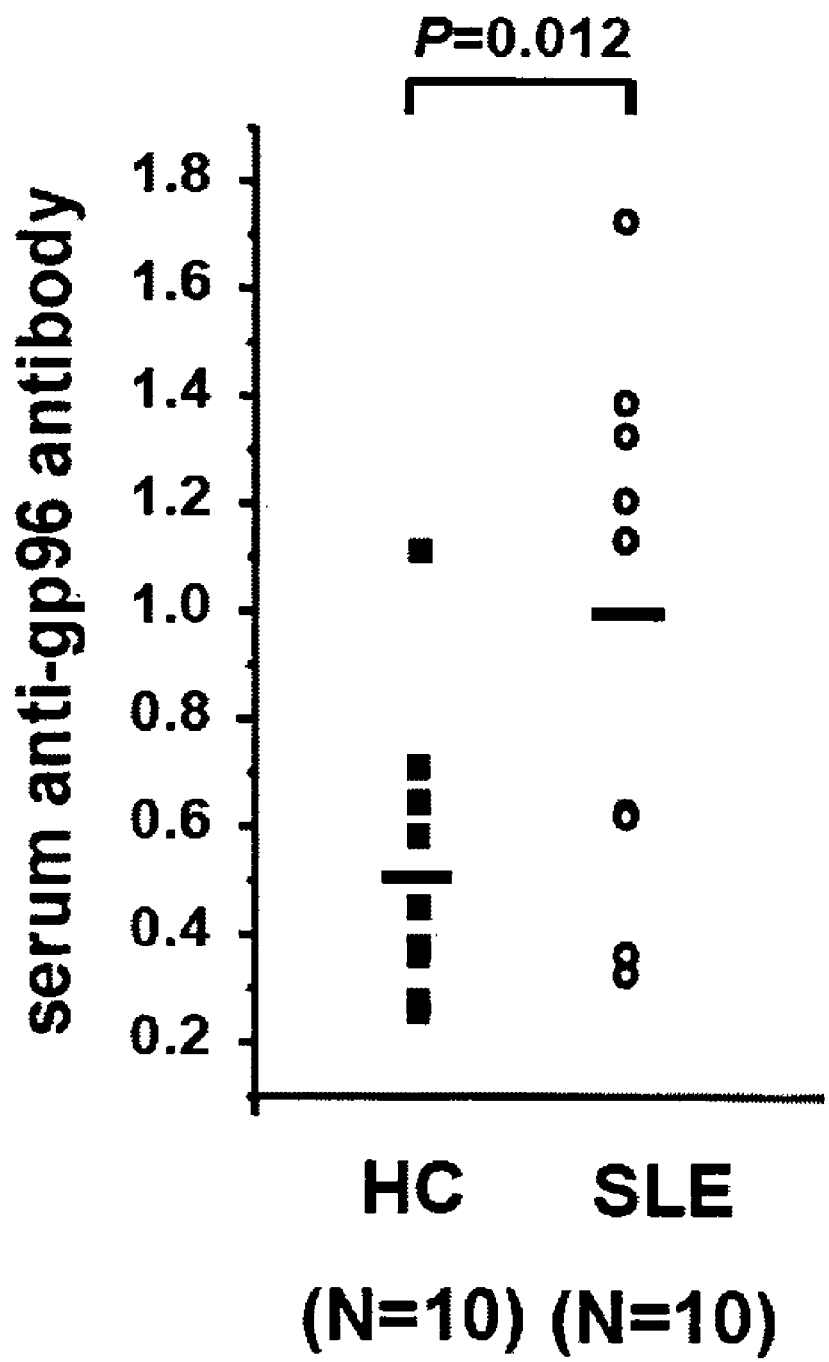

The present inventors also examined whether the association of the increased surface expression of gp96 with SLE phenotypes in mice is also observed in human cases. The present inventors thus isolated Peripheral Blood Mononuclear Cell (PBMC) of blood from healthy control (n=7) and SLE patients (n=12) and analyzed the surface levels of gp96. The cell surface gp96 on blood PBMCs and $gp96^+HLA-DR^+$ population were increased in SLE patients (FIGS. 31 and 32). The present inventors also compared the serum anti-gp96 antibody levels between healthy control (n=10) and SLE patients (n=10). The anti-gp96 antibody level was also increased in the sera of SLE patients (FIG. 33). These results suggest the possibility that the increase of cell surface gp96 may also have clinical implication for human SLE. Combined together, these results demonstrated that cell surface level of gp96 can be chemically controlled and suggest gp96 as a potential target to compromise SLE-like autoimmune phenotypes.

The present inventors also tested the effect of 2,4-pyrimidine derivatives through a lupus animal model. An NZB/W F1 mouse is a lupus animal model showing a voluntary lupus symptom. On the animal model, the effect of the 2,4-pyrimidine derivative was tested.

Figure 34:
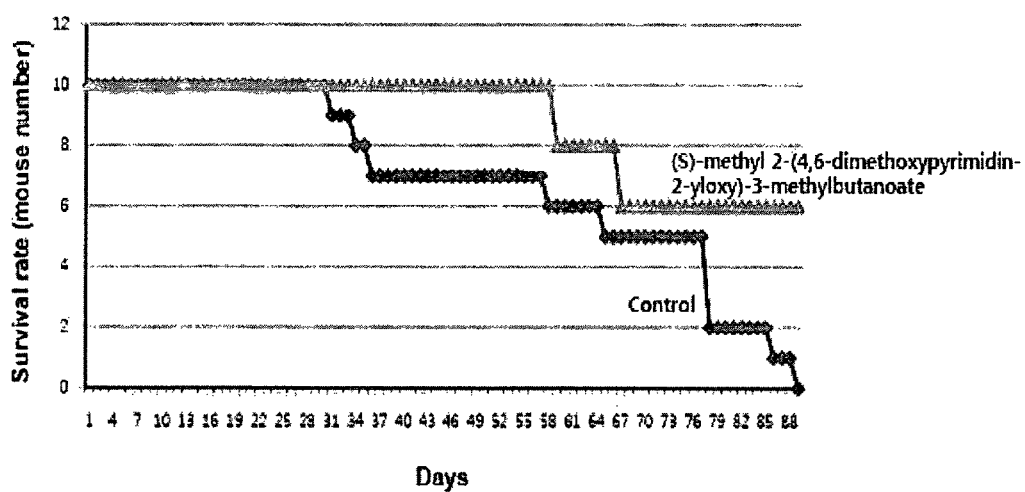
FIG. 34 is a graph showing a test result on a lupus symptom relieving effects of the inventive 2,4-pyrimidine derivatives in a lupus animal model.

Each group included 10 of 25-week aged male NZB/W F1 mouse. Each group was intraperiotneally administered with a control (5% DMSO solution) or a testing agent (2,4-pyrimidine derivative in a dose of 30 mg/kg) once a day. Except for mice which died by worsening of lupus symptoms, the ratio of surviving mice was analyzed. As a result, in a group administered with (S)-methyl 2-(4,6-dimethoxypyrimidin-2-yloxy)-3-methylbutanoate, the ratio of mice which died by lupus was significantly reduced (FIG. 34).

Accordingly, it was verified that in a generally used animal model, the 2,4-pyrimidine derivatives have an effect on relieving the symptoms of lupus.

INDUSTRIAL APPLICABILITY

As described above, the present inventors found novel materials that inhibit surface translocation of gp96 by mimicking a function of AIMP1 that is a molecular anchor for an intracellular residence of gp96, and then identified that the materials in vitro and in vivo relieve an SLE character, and have an effect on preventing or treating SLE. Accordingly, the present invention provides a novel method of screening a therapeutic agent for SLE, and for preventing or treating SLE, by using the mechanism.

The invention claimed is:
1. A method for treating systemic lupus erythematosus in a subject comprising:
administering to a subject in need thereof an effective dose of a compound represented by Formula 1 or its pharmaceutically acceptable salt:

<Formula 1>

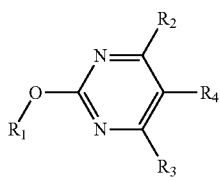

wherein,
$R_1$ represents hydrogen, benzyl, halobenzyl, pyridine, aminopyridine, tert-butyl, or

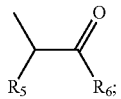

wherein $R_5$ represents straight or branched ($C_1$-$C_7$) alkyl, unsubstituted or halogen-substituted ($C_6$) aryl or thiophene, and $R_6$ represents hydroxy, ($C_1$-$C_7$) alkoxy, straight or branched ($C_1$-$C_7$) alkylamino, ($C_2$-$C_7$) dialkylamino, morpholine, or piperidine;
$R_2$ and $R_3$ each independently represent hydrogen, ($C_1$-$C_7$) alkyl, ($C_1$-$C_7$) alkoxy, or halogen-substituted trihalomethylphenoxy; and
$R_4$ represents hydrogen, halogen, carboxyamide or pyridine.

2. The method according to claim 1, wherein the compound is a compound represented by Formula 1 or its pharmaceutically acceptable salt:

<Formula 1>

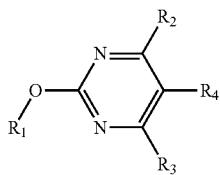

wherein,
$R_1$ represents hydrogen, benzyl, halobenzyl, pyridine, aminopyridine, tert-butyl or

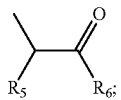

wherein $R_5$ represents methyl, unsubstituted or halogen-substituted ($C_6$) aryl or thiophene, and $R_6$ represents hydroxyl, methoxy, butylamino, isopropylamino, diethylamino, morpholine, or piperidine;
$R_2$ and $R_3$ each independently represent hydrogen, methyl, methoxy, tert-butoxy or fluoro-substituted trifluoromethylphenoxy; and
$R_4$ represents hydrogen, chloro, carboxyamide or pyridine.

3. A method for treating systemic lupus erythematosus in a subject comprising:
administering to a subject in need thereof an effective dose of a compound,
wherein the compound is selected from the group consisting of
(S)-methyl 2-(4,6-dimethoxypyrimidin-2-yloxy)-3-methylbutanoate,
methyl 2-(5-chloro-4-methoxy-6-methylpyrimidin-2-yloxy)propanoate,
methyl 2-(4-bromophenyl)-2-(4,6-dimethoxypyrimidin-2-yloxy)acetate,
methyl 2-(4,6-dimethoxypyrimidin-2-yloxy)-3-methylbutanoate,
methyl 2-(4,6-dimethoxypyrimidin-2-yloxy)-2-(thiophen-2-yl)acetate,
2-(4,6-dimethoxypyrimidin-2-yloxy)-2-phenylacetic acid,
(R)-2-(4,6-dimethoxypyrimidin-2-yloxy)-2-phenylacetic acid,
2-(benzyloxy)-4,6-dimethoxypyrimidine-5-carboxamide,
2-(2-chlorobenzyloxy)-4,6-dimethoxypyrimidine,
4,6-dimethoxy-2-(pyridin-4-yloxy)pyrimidine,
4,6-di-tert-butoxy-2-(pyridin-3-yloxy)pyrimidine,
2,4-di-tert-butoxy-5-(pyridin-2-yl)pyrimidine,
4,6-bis(4-fluoro-3-(trifluoromethyl)phenoxy)pyrimidin-2-ol,
3-(4,6-dimethoxypyrimidin-2-yloxy)pyridin-2-amine,
2-(4,6-Dimethoxy-pyrimidin-2-yloxy)-N,N-diethyl-3-methyl-butyl amide,
N-Butyl-2-(4,6-dimethoxy-pyrimidin-2-yloxy)-3-methyl-butyl amide,
2-(4,6-Dimethoxy-pyrimidin-2-yloxy)-3-methyl-N-phenyl-butyl amide,
N-Benzyl-2-(4,6-dimethoxy-pyrimidin-2-yloxy)-3-methyl-butyl amide,
2-(4,6-dimethoxy-pyrimidin-2-yloxy)-N-isopropyl-3-methyl-butyl amide,
2-(4,6-dimethoxy-pyrimidin-2-yloxy)-N-methoxy-3,N-dimethyl-butyl amide,
2-(4,6-dimethoxy-pyrimidin-2-yloxy)-3-methyl-1-piperidin-1-yl-butan-1-one,
2-(4,6-dimethoxy-pyrimidin-2-yloxy)-3-methyl-1-morpholin-4-yl-butan-1-one,
2-(4,6-dimethoxy-pyrimidin-2-yloxy)-3-methyl-butyric acid,
2-(4,6-Dimethoxy-pyrimidin-2-yloxy)-3-methyl-butyric acid methyl ester,
L-2-(4,6-Dimethoxy-pyrimidin-2-yloxy)-propionic acid methyl ester,
D-2-(4,6-Dimethoxy-pyrimidin-2-yloxy)-propionic acid methyl ester,
2-(4,6-Dimethoxy-pyrimidin-2-yloxy)-2-methyl-propionic acid methyl ester,
D-3-(4,6-Dimethoxy-pyrimidin-2-yloxy)-butyric acid methyl ester,
L-2-(4,6-Dimethoxy-pyrimidin-2-yloxy)-3-methyl-butyric acid methyl ester,
(4,6-Dimethoxy-pyrimidin-2-yloxy)-phenyl-acetic acid methyl ester, (4,6-Dimethoxy-pyrimidin-2-yloxy)-phenyl-acetic acid,
2-(4,6-Dimethoxy-pyrimidin-2-yloxy)-N-isopropyl-2-phenyl-acetamide,
N-Benzyl-2-(4,6-dimethoxy-pyrimidin-2-yloxy)-2-phenyl-acetamide,
N-Butyl-2-(4,6-dimethoxy-pyrimidin-2-yloxy)-2-phenyl-acetamide,
2-(4,6-Dimethoxy-pyrimidin-2-yloxy)-N,N-diethyl-2-phenyl-acetamide,
L-2-(4,6-Dimethoxy-pyrimidin-2-yloxy)-3-methyl-butyric acid,
D-2-(4,6-Dimethoxy-pyrimidin-2-yloxy)-propionic acid, and
L-2-(4,6-Dimethoxy-pyrimidin-2-yloxy)-propionic acid.

* * * * *